(12) United States Patent
Weiss et al.

(10) Patent No.: US 12,370,359 B2
(45) Date of Patent: Jul. 29, 2025

(54) PULSE DEFINITION CIRCUITRY FOR CREATING STIMULATION WAVEFORMS IN AN IMPLANTABLE PULSE GENERATOR

(71) Applicant: Boston Scientific Neuromodulation Corporation, Valencia, CA (US)

(72) Inventors: Philip Leonard Weiss, Sherman Oaks, CA (US); Goran N. Marnfeldt, Valencia, CA (US); David Michael Wagenbach, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 108 days.

(21) Appl. No.: 18/464,914

(22) Filed: Sep. 11, 2023

(65) Prior Publication Data

US 2023/0414927 A1  Dec. 28, 2023

Related U.S. Application Data

(63) Continuation of application No. 16/717,767, filed on Dec. 17, 2019, now Pat. No. 11,793,999, which is a
(Continued)

(51) Int. Cl.
*A61N 1/02* (2006.01)
*A61N 1/05* (2006.01)
(Continued)

(52) U.S. Cl.
CPC .............. *A61N 1/025* (2013.01); *A61N 1/05* (2013.01); *A61N 1/36* (2013.01); *A61N 1/36125* (2013.01); *A61N 1/3925* (2013.01)

(58) Field of Classification Search
CPC . A61N 1/025; A61N 1/05; A61N 1/36; A61N 1/36125; A61N 1/3925
See application file for complete search history.

(56) References Cited

U.S. PATENT DOCUMENTS 6,181,969 B1  1/2001  Gord
6,516,227 B1  2/2003  Meadows et al.
(Continued)

FOREIGN PATENT DOCUMENTS

WO  2015/175803  11/2015

OTHER PUBLICATIONS

International Search Report and Written Opinion regarding corresponding PCT Application No. PCT/US2017/050305, mailed Dec. 6, 2017.
(Continued)

*Primary Examiner* — Amanda K Hulbert
(74) *Attorney, Agent, or Firm* — Lewis & Reese, PLLC

(57) ABSTRACT

Improved stimulation circuitry for controlling the stimulation delivered by an implantable stimulator is disclosed. The stimulation circuitry includes memory circuitry that stores pulse programs that define pulse shapes, steering programs that define electrode configurations, and aggregate programs that link a selected pulse program with a selected steering program. Each steering program defines the stimulation polarity and the allocation of current of the specified stimulation polarity for each of the pulse generator's electrodes. Each pulse program includes one or more pulse instructions, where each instruction defines the parameters of a single phase of the pulse program. Pulse definition circuits in the stimulation circuitry execute aggregate programs to generate stimulation waveforms, which stimulation waveforms can be generated simultaneously by the different pulse definition circuits.

20 Claims, 37 Drawing Sheets

Related U.S. Application Data continuation of application No. 15/696,031, filed on Sep. 5, 2017, now Pat. No. 10,576,265.

(60) Provisional application No. 62/386,000, filed on Sep. 10, 2016.

(51) Int. Cl.
*A61N 1/36* (2006.01)
*A61N 1/39* (2006.01)

(56) References Cited

U.S. PATENT DOCUMENTS

| | | |
|---|---|---|
| 6,553,263 B1 | 4/2003 | Meadows et al. |
| 7,127,298 B1 | 10/2006 | He et al. |
| 7,177,698 B2 | 2/2007 | Klosterman et al. |
| 7,444,181 B2 | 10/2008 | Shi et al. |
| 7,539,538 B2 | 5/2009 | Parramon et al. |
| 7,623,916 B2 | 11/2009 | Julian |
| 7,801,600 B1 | 9/2010 | Carbunaru et al. |
| 7,801,602 B2 | 9/2010 | McClure et al. |
| 7,872,884 B2 | 1/2011 | Parramon et al. |
| 7,881,803 B2 | 2/2011 | Parramon et al. |
| 7,890,182 B2 | 2/2011 | Parramon et al. |
| 8,340,775 B1 | 12/2012 | Cullen et al. |
| 8,606,362 B2 | 12/2013 | He et al. |
| 8,620,436 B2 | 12/2013 | Parramon et al. |
| 8,649,858 B2 | 2/2014 | Griffith et al. |
| 8,768,453 B2 | 7/2014 | Parramon et al. |
| 9,002,465 B2 | 4/2015 | Ranu |
| 9,008,790 B2 | 4/2015 | Griffith et al. |
| 9,037,241 B2 | 5/2015 | Lamont et al. |
| 9,061,140 B2 | 6/2015 | Shi et al. |
| 9,155,891 B2 | 10/2015 | Archer |
| 9,174,051 B2 | 11/2015 | Marnfeldt et al. |
| 9,220,901 B2 | 12/2015 | Gururaj et al. |
| 9,233,254 B2 | 1/2016 | Nimmagadda et al. |
| 9,259,574 B2 | 2/2016 | Aghassian et al. |
| 9,308,373 B2 | 4/2016 | Lee |
| 9,314,632 B2 | 4/2016 | Marnfeldt et al. |
| 9,327,135 B2 | 5/2016 | Vansickle et al. |
| 9,352,162 B2 | 5/2016 | Lamont et al. |
| 9,397,639 B2 | 7/2016 | Feldman et al. |
| 2004/0116978 A1 | 6/2004 | Bradley |
| 2006/0173493 A1 | 8/2006 | Armstrong et al. |
| 2008/0004675 A1 | 1/2008 | King et al. |
| 2008/0154340 A1 | 6/2008 | Goetz et al. |
| 2010/0137938 A1 | 6/2010 | Kishawi et al. |
| 2010/0268309 A1 | 10/2010 | Parramon et al. |
| 2010/0331921 A1 | 12/2010 | Bornzin et al. |
| 2011/0184496 A1 | 7/2011 | Kallmyer |
| 2011/0270348 A1 | 11/2011 | Goetz |
| 2012/0095529 A1 | 4/2012 | Parramon et al. |
| 2012/0277621 A1 | 11/2012 | Gerber et al. |
| 2013/0006332 A1 | 1/2013 | Sommer et al. |
| 2013/0066400 A1 | 3/2013 | Perryman et al. |
| 2013/0172956 A1 | 7/2013 | Goddard et al. |
| 2013/0184794 A1 | 7/2013 | Feldman et al. |
| 2014/0094871 A1 | 4/2014 | Trier et al. |
| 2015/0134029 A1 | 5/2015 | Ozawa et al. |
| 2015/0144183 A1 | 5/2015 | Yang et al. |
| 2015/0157861 A1 | 6/2015 | Aghassian |
| 2016/0051816 A1 | 2/2016 | Yonce |
| 2016/0051825 A1 | 2/2016 | Ter-Petrosyan et al. |
| 2016/0121126 A1 | 5/2016 | Marnfeldt |
| 2016/0206883 A1 | 7/2016 | Bornzin et al. |
| 2018/0071516 A1 | 3/2018 | Weiss |

OTHER PUBLICATIONS

Extended Search Report regarding corresponding European Patent Application No. 20203842.8, mailed Feb. 18, 2021.

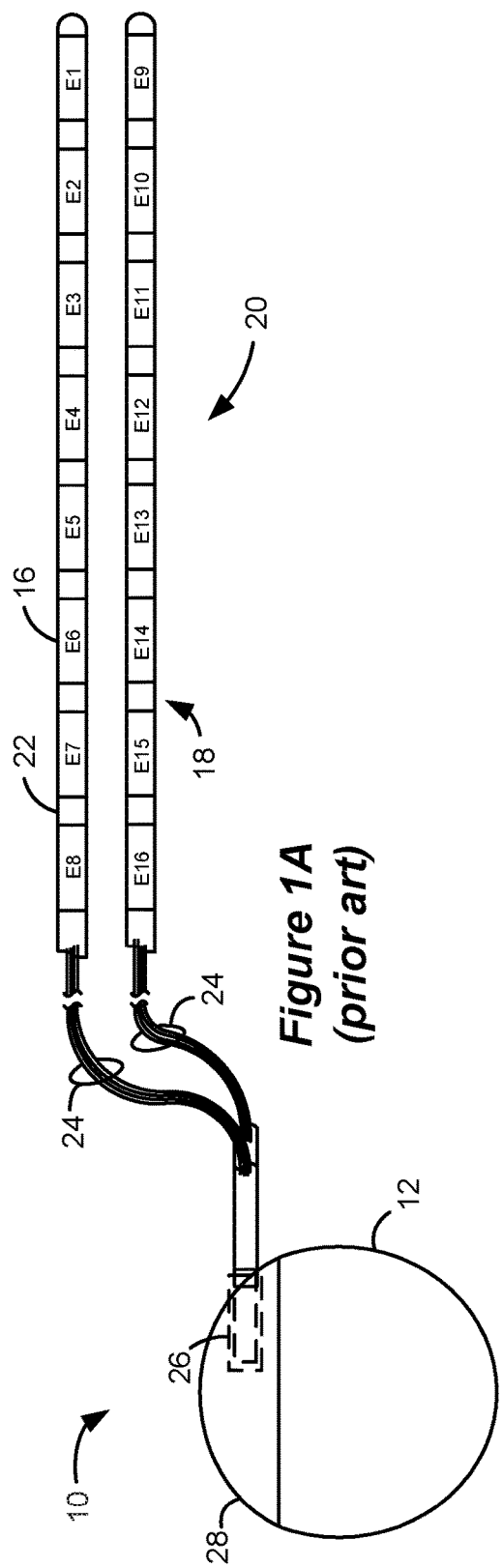
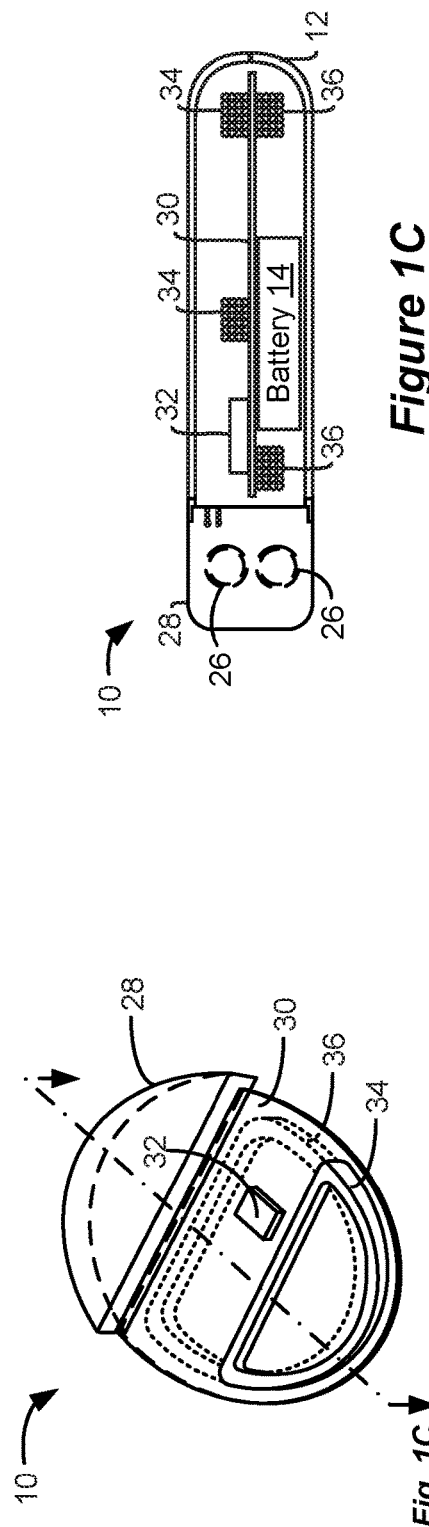
*Figure 1A (prior art)*
*Figure 1B (prior art)*
*Figure 1C (prior art)*

AGGREGATE INSTRUCTION

| 31 | 30 | 29 | 28 | 27 | 26 | 25 | 24 | 23 | 22 | 21 | 20 | 19 | 18 | 17 | 16 | 15 | 14 | 13 | 12 | 11 | 10 | 9 | 8 | 7 | 6 | 5 | 4 | 3 | 2 | 1 | 0 |

INTERRUPT — NUMBER OF REPEATS — STEERING PROGRAM — PULSE REGISTER BLOCK ADDRESS

*Figure 10*

AGGREGATE MEMORY 506

|   |   |    |   |      |
|---|---|----|---|------|
| Y   | N | 2  | A | X    |
| Y+1 | N | 5  | B | X    |
| Y+2 | N | 13 | C | X+6  |
| Y+3 | N | 5  | C | X    |
| Y+4 | N | 5  | D | X+64 |
| Y+5 | N | 7  | D | X+6  |

*Figure 11*

| STEERING PROGRAM | CATHODE | ANODE |
|---|---|---|
| A | E2-100% | E1-100% |
| B | E3-100% | E1-40%; E2-60% |
| C | E5-100% | E4-100% |
| D | E5-80%; E6-20% | E4-100% |

*Figure 12*

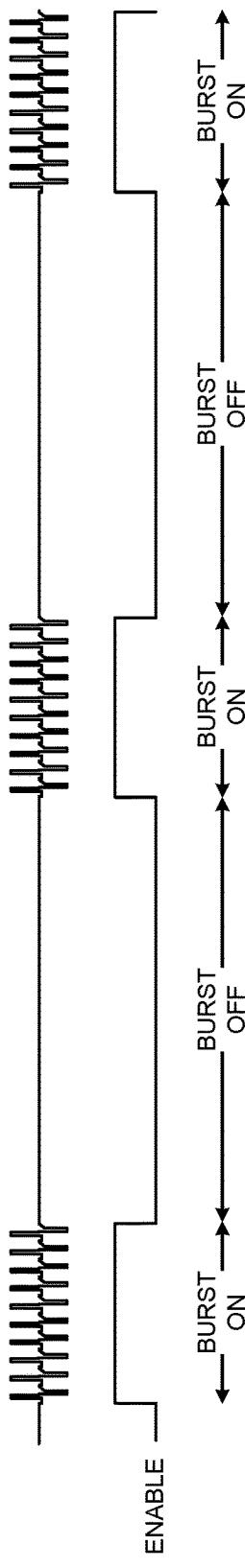

*Figure 19*

| | STANDARD | | | HIGH RESOLUTION | | |
|---|---|---|---|---|---|---|
| | DELAY | STIMULATION | ACTIVE RECOVERY | DELAY | STIMULATION | ACTIVE RECOVERY |
| <Cp> | ALL OPEN | UPPER 5 BITS OF SP ANODE | UPPER 5 BITS OF SP CATHODE | ALL OPEN | ALL 7 BITS OF SP ANODE | ALL 7 BITS OF SP CATHODE |
| <Cn> | ALL OPEN | UPPER 5 BITS OF SP CATHODE | UPPER 5 BITS OF SP ANODE | ALL OPEN | ALL 7 BITS OF SP CATHODE | ALL 7 BITS OF SP ANODE |
| <Jp> | 0 (PASSIVE) A*AS*RS (ACTIVE) | A*AS*RS | A*AS*RS | 0 (PASSIVE) A*AS*RS (ACTIVE) | A*AS*RS | A*AS*RS |
| <Jn> | 0 (PASSIVE) A*AS*RS (ACTIVE) | A*AS*RS | A*AS*RS | 0 (PASSIVE) A*AS*RS (ACTIVE) | A*AS*RS | A*AS*RS |

*Figure 20*

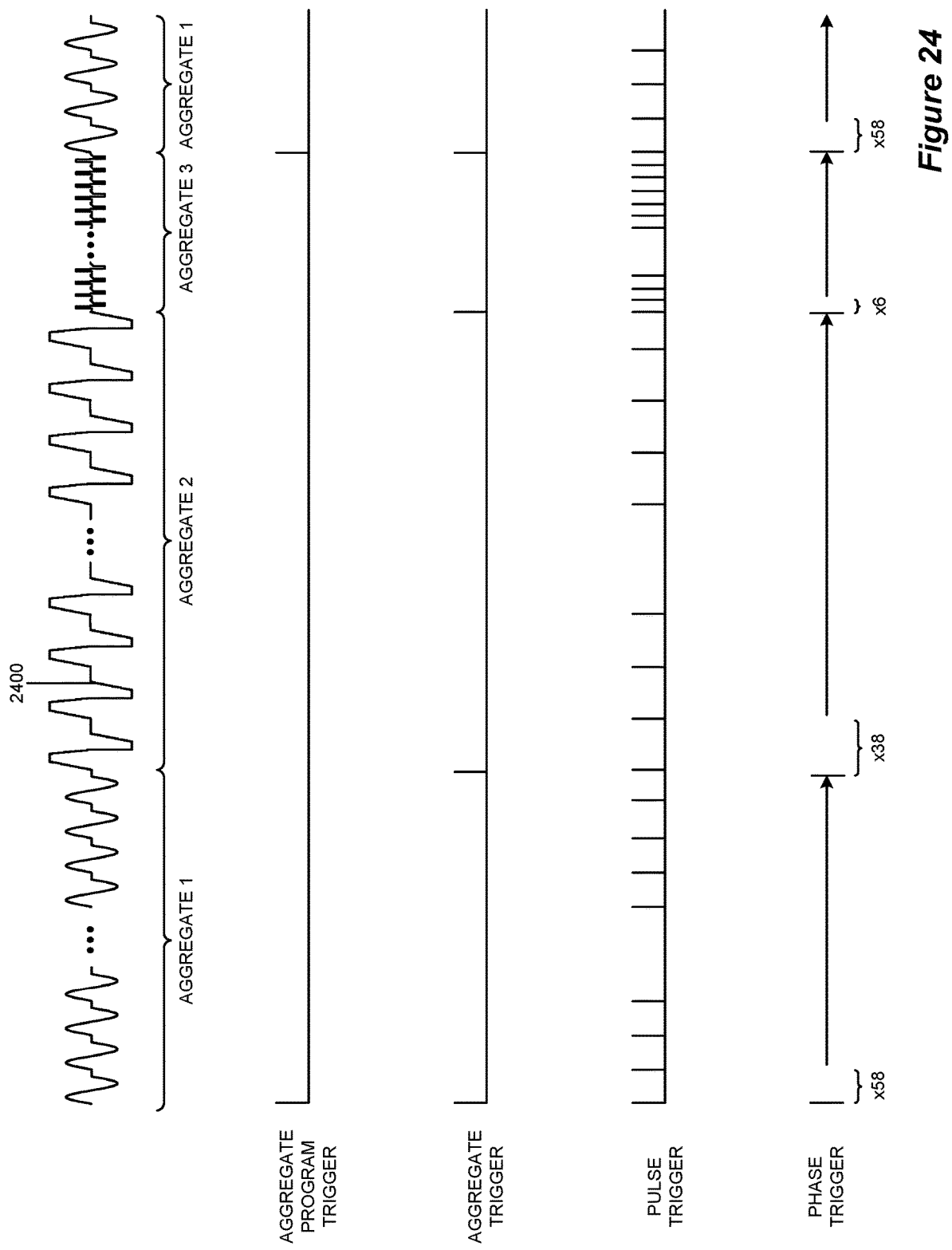

| WT1 | WAIT TRIGGER (0,00,00,2000) |
| --- | --- |
| SC1 | STEER CONFIG (0,0,1,0,0,0,0) |
| SC2 | STEER CONFIG (0,0,0,1,33,0,01100100) |
| SC3 | STEER CONFIG (1,1,0,1,34,0,11100100) |
| V1 | VARIABLE (0,WRITE,13,E1) |
| V2 | VARIABLE (0,WRITE,14,E2) |
| WT2 | WAIT TRIGGER (0,00,01,1) |
| SS1 | SET SWITCHES (1,GND,GND,11111) |
| WT3 | WAIT TRIGGER (0,00,11,1) |
| W1 | WAIT (0,0,2) |
| SS2 | SET SWITCHES (1,127,126,01001) |
| W2 | WAIT (0,0,3) |
| SS3 | SET SWITCHES (1,0,0,00000) |
| WT4 | WAIT TRIGGER (0,00,11,1) |
| W3 | WAIT (0,0,2) |
| SS4 | SET SWITCHES (1,126,127,00110) |
| W4 | WAIT (0,0,3) |
| SS5 | SET SWITCHES (1,0,0,00000) |
| W5 | WAIT (0,0,4) |
| SS6 | SET SWITCHES (1,CM,CM,11010) |
| W6 | WAIT (0,0,4) |
| SS7 | SET SWITCHES (1,0,0,10000) |
| M1 | MEASURE (0,0,0,1) |
| V3 | VARIABLE (0,ADD,14,1) |
| WT5 | WAIT TRIGGER (0,00,10,2) |
| J1 | JUMP (1,14,A≤B,SS1) |

PULSE DEFINITION CIRCUITRY FOR CREATING STIMULATION WAVEFORMS IN AN IMPLANTABLE PULSE GENERATOR

CROSS REFERENCE TO RELATED APPLICATIONS

This application is a continuation of U.S. Non-Provisional application Ser. No. 16/717,767, filed Dec. 17, 2019, which is a continuation of U.S. Non-Provisional application Ser. No. 15/696,031, filed Sep. 5, 2017, which is a non-provisional application based on U.S. Provisional Patent Application Ser. No. 62/386,000, filed Sep. 10, 2016. These applications are incorporated herein by reference in their entirety, and priority is claimed to them.

FIELD OF THE INVENTION

The present invention relates generally to implantable medical devices, and more particularly to improved stimulation circuitry for creating pulses and improved measurement circuitry for measuring values in an implantable medical device.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system, including a Deep Brain Stimulation (DBS) system.

As shown in FIGS. 1A-1C, an SCS system typically includes an Implantable Pulse Generator (IPG) 10 (Implantable Medical Device (IMD) 10 more generally), which includes a biocompatible device case 12 formed of a conductive material such as titanium for example. The case 12 typically holds the circuitry and power source (e.g., battery) 14 (FIG. 1C) necessary for the IPG 10 to function, although IPGs can also be powered via external RF energy and without a battery. The IPG 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ex) on two leads 18 for a total of sixteen electrodes 16, although the number of leads and electrodes is application specific and therefore can vary. The leads 18 couple to the IPG 10 using lead connectors 26, which are fixed in a non-conductive header material 28, which can comprise an epoxy for example.

As shown in the cross-section of FIG. 1C, the IPG 10 typically includes a printed circuit board (PCB) 30, along with various electronic components 32 mounted to the PCB 30, some of which are discussed subsequently. Two coils (more generally, antennas) are shown in the IPG 10: a telemetry coil 34 used to transmit/receive data to/from an external controller (not shown); and a charging coil 36 for charging or recharging the IPG's battery 14 using an external charger (not shown), although the IPG 10's battery may also be non-rechargeable, in which case the charging coil 36 would not be necessary. FIG. 1B shows these aspects in perspective with the case 12 removed for easier viewing. Telemetry coil 34 may alternatively comprise a short range RF antenna for wirelessly communicating in accordance with a short-range RF standard such as Bluetooth, WiFi, MICS, Zigbee, etc., as described in U.S. Patent Application Publication 2016/0051825.

FIG. 2A shows a prior art architecture 40 for the circuitry in IPG 10, which is disclosed in U.S. Patent Application Publications 2012/0095529, 2012/0092031 and 2012/0095519 ("ASIC Publications"), which are incorporated by reference in their entireties. Architecture 40 includes a microcontroller integrated circuit 50 and an Application Specific Integrated Circuit (ASIC) 60 in communication with each other by a bus 90. Stated simply, the microcontroller 50 provides master control for the architecture 40, while ASIC 60 takes commands from and provides data to the microcontroller. ASIC 60 provides specific IPG functionality. For example, and as explained in further detail below, ASIC 60 sends stimulation current to and reads measurements from the sixteen electrodes 16. ASIC 60 comprises a mixed mode IC carrying and processing both analog and digital signals, whereas microcontroller 50 comprises a digital IC carrying and processing only digital signals.

Microcontroller 50 and ASIC 60 comprise monolithic integrated circuits each formed on their own semiconductive substrates ("chips"), and each may be contained in its own package and mounted to the IPG 10's PCB 30. Architecture 40 may also include additional memory (not shown) for storage of programs or data beyond that provided internally in the microcontroller 50. Additional memory may be connected to the microcontroller 50 by a serial interface (SI) as shown, but could also communicate with the microcontroller 50 via bus 90. Bus 90 may comprise a parallel address/data bus, and may include a clock signal and various control signals to dictate reading and writing to various memory locations, as explained in the '529 Publication. Bus 90 and the signals it carries may also take different forms; for example, bus 90 may include separate address and data lines, may be serial in nature, etc.

As explained in the above-referenced ASIC Publications, architecture 40 is expandable to support use of a greater number of electrodes 16 in the IPG 10. For example, and as shown in dotted lines in FIG. 2A, architecture 40 may include another ASIC 60' identical in construction to ASIC 60, thus expanding the number of electrodes supported by the IPG 10 from sixteen to thirty two. Various off-bus connections 54 (i.e., connections not comprising part of bus 90) can facilitate such expansion, and may further (e.g., by bond programming; see inputs M/S) designate ASIC 60 as a master and ASIC 60' as a slave. Such differentiation between the ASICs 60 and 60' can be useful, as certain redundant functionality in the slave ASIC 60' can be disabled in favor of the master ASIC 60. Off-bus communications 54 can allow the voltage at the electrode nodes 61a (E1'-EN') of one of the ASICs (60'; OUT1, OUT2) to be sent to the other ASIC (60; IN1, IN2) to be measured. Off-bus connections 54 are further useful in generation and distribution of a clock signal governing communications on the bus 90 as well as in the ASIC(s) 60. As these concepts are discussed in detail in the above-referenced ASIC Publications, they are not elaborated upon here.

FIG. 2B shows various functional circuit blocks within ASIC 60, which are briefly described. ASIC 60 includes an internal bus 92 which can couple to external bus 90 and which may duplicate bus 90's signals. Note that each of the functional blocks includes interface circuitry 88 enabling communication on the internal bus 92 and ultimately external bus 90, as the above-referenced ASIC Publications explain. Interface circuitry 88 includes circuitry to help each block recognize when bus 92 is communicating data with addresses belonging to that block. ASIC 60 contains several terminals 61 (e.g., pins, bond pads, solder bumps, etc.), such as those necessary to connect to the bus 90, the battery 14, the coils 34, 36, external memory (not shown). Terminals 61 include electrode node terminals 61a (E1'-EN') which connect to the electrodes 16 (E1-EN) on the lead(s) 18 by way of DC-blocking capacitors 55. As is known, DC-blocking capacitors 55 are useful to ensure that DC current isn't inadvertently (e.g., in the event of failure of the ASIC 60's circuitry) injected into the patient's tissue, and hence provide safety to the IPG 10. Such DC-blocking capacitors 55 can be located on or in the IPG 10's PCB 30 (FIG. 1C) inside of the IPG's case 12. See U.S. Patent Application Publication 2015/0157861.

Each of the circuit blocks in ASIC 60 performs various functions in IPG 10. Telemetry block 64 couples to the IPG telemetry coil 34, and includes transceiver circuitry for wirelessly communicating with an external device according to a telemetry protocol. Such protocol may comprise Frequency Shift Keying (FSK), Amplitude Shift Keying (ASK), or various short-range RF standards such as those mentioned above. Charging/protection block 62 couples to the IPG charging coil 36, and contains circuitry for rectifying power wirelessly received from an external charger (not shown), and for charging the battery 14 in a controlled fashion.

Analog-to-Digital (A/D) block 66 digitizes various analog signals for interpretation by the IPG 10, such as the battery voltage Vbat or voltages appearing at the electrodes, and is coupled to an analog bus 67 containing such voltages. A/D block 66 may further receive signals from sample and hold block 68, which as the ASIC Publications explain can be used to measure such voltages, or differences between two voltages. For example, sample and hold circuitry 68 may receive voltages from two electrodes and provide a difference between them (see, e.g., VE1-VE2 in FIG. 3A, discussed subsequently), which difference in voltage may then be digitized at A/D block 66. Knowing the difference in voltage between two electrodes when they pass a constant current allows for a determination of the (tissue) resistance between them, which is useful for a variety of reasons.

Sample and hold block 68 may also be used to determine one or more voltage drops across the DAC circuitry 72 used to create the stimulation pulses (see, e.g., Vp and Vn in FIG. 3A, explained subsequently). This is useful to setting the compliance voltage V+ to be output by a compliance voltage generator block 76. Compliance voltage VH powers the DAC circuitry 72, and the measured voltage drops ensure that the compliance voltage VH produced is optimal for the stimulation current to be provided—i.e., VH is not too low as to be unable to produce the current required for the stimulation, nor too high so as to waste power in the IPG 10. Compliance voltage generator block 76 includes circuitry for boosting a power supply voltage such as the battery voltage, Vbat, to a proper level for VH. Such circuitry (some of which may be located off chip) can include an inductor-based boost converter or a capacitor-based charge pump, which are described in detail in U.S. Patent Application Publication 2010/0211132.

Clock generation block 74 can be used to generate a clock for the ASIC 60 and communication on the bus. Clock generation block 74 may receive an oscillating signal from an off-chip crystal oscillator 56, or may comprise other forms of clock circuitry located completely on chip, such as a ring oscillator. U.S. Patent Application Publication 2014/0266375 discloses another on-chip circuit that can be used to generate a clock signal on the ASIC 60.

Master/slave control block 86 can be used to inform the ASIC 60 whether it is to be used as a master ASIC or as a slave ASIC (e.g., 60'), which may be bond programmed at M/S terminal 61. For example, M/S terminal may be connected to a power supply voltage (e.g., Vbat) to inform ASIC 60 that it will operate as a master ASIC, or to ground to inform that it will operate as a slave, in which case certain function blocks will be disabled, as the ASIC Publications explain.

Interrupt controller block 80 receives various interrupts (e.g., INT1-INT4) from other circuit blocks, which because of their immediate importance are received independent of the bus 92 and its communication protocol. Interrupts may also be sent to the microcontroller 50 via the bus 90. Internal controller 82 in the ASIC 60 may receive indication of such interrupts, and act as a controller for all other circuit blocks, to the extent microcontroller 50 (FIG. 2A) does not handle such interrupt through the external bus 90. Further, each of the functional circuit blocks contain set-up and status registers (not shown) written to by the controller 82 upon initialization to configure and enable each block. Each functional block can then write pertinent data at its status registers, which can in turn be read by the controller 82 via internal bus 92 as necessary, or by the microcontroller 50 via external bus 90. The functional circuit blocks can function as simple state machines to manage their operation, which state machines are enabled and modified via each block's set-up and status registers.

Nonvolatile memory (NOVO) block 78 caches any relevant data in the system (such as log data). Additional memory (not shown) can also be provided off-chip via a serial interface block 84.

ASIC 60 further includes a stimulation circuit block 70, which includes circuitry for receiving and storing stimulation parameters from the microcontroller 50 via buses 90 and 92. Stimulation parameters define the shape and timing of stimulation pulses to be formed at the electrodes, and can include parameters such as which electrodes E1-EN will be active; whether those active electrodes are to act as anodes that source current to a patient's tissue, or cathodes that sink current from the tissue; and the amplitude (A), duration (d), and frequency (f) of the pulses. Amplitude may comprise a voltage or current amplitude. Such stimulation parameters may be stored in registers in the stimulation circuitry block 70. See, e.g., U.S. Patent Application Publications 2013/0289661; 2013/0184794.

Block 70 also includes a Digital-to-Analog Converter (DAC) 72 for receiving the stimulation parameters from the registers and for forming the prescribed pulses at the selected electrodes. FIG. 3A shows a simple example of DAC circuitry 72 as used to provide a current pulse between selected electrodes E1 and E2 and through a patient's tissue, R. DAC circuitry 72 as shown comprises two portions, denoted as PDAC 72p and NDAC 72n. These portions of DAC circuitry 72 are so named because of the polarity of the transistors used to build them and the polarity of the current they provide. Thus, PDAC 72p is formed from P-channel transistors and is used to source a current +I to the patient's tissue R via a selected electrode E1 operating as an anode.

NDAC 72n is formed of N-channel transistors and is used to sink current −I from the patient's tissue via a selected electrode E2 operating as a cathode. It is important that current sourced to the tissue at any given time equal that sunk from the tissue to prevent charge from building in the tissue, although more than one anode electrode and more than one cathode electrode may be operable at a given time.

PDAC 72p and NDAC 72n receive digital control signals from the registers in the stimulation circuitry block 70, denoted <Pstim> and <Nstim> respectively, to generate the prescribed pulses with the prescribed timing. In the example shown, PDAC 72p and NDAC 72n comprise current sources, and in particular include current-mirrored transistors for mirroring (amplifying) a reference current Iref to produce pulses with an amplitude (A). PDAC 72p and NDAC 72n could however also comprise constant voltage sources. Control signals <Pstim> and <Nstim> also prescribe the timing of the pulses, including their duration (D) and frequency (f), as shown in the example waveform in FIG. 3B. The PDAC 72p and NDAC 72n along with the intervening tissue R complete a circuit between a power supply VH—the compliance voltage as already introduced—and ground. As noted earlier, the compliance voltage VH is adjustable to an optimal level at compliance voltage generator block 76 (FIG. 2B) to ensure that current pulses of a prescribed amplitude can be produced without unnecessarily wasting IPG power.

The DAC circuitry 72 (PDAC 72p and NDAC 72n) may be dedicated at each of the electrodes, and thus may be activated only when its associated electrode is to be selected as an anode or cathode. See, e.g., U.S. Pat. No. 6,181,969. Alternatively, one or more DACs (or one or more current sources within a DAC) may be distributed to a selected electrode by a switch matrix (not shown), in which case optional control signals <Psel> and <Nsel> would be used to control the switch matrix and establish the connection between the selected electrode and the PDAC 72p or NDAC 72n. See, e.g., U.S. Pat. No. 8,606,362. DAC circuitry 72 may also use a combination of these dedicated and distributed approaches. See, e.g., U.S. Pat. No. 8,620,436.

In the example waveform shown in FIG. 3B, the pulses provided at electrodes E1 and E2 are biphasic, meaning that each pulse includes a stimulation phase of a first polarity and an active recovery phase of an opposite polarity (along with additional phases that are not therapeutically meaningful that are described below). This is useful as a means of active recovery of charge that may build up on the DC-blocking capacitors 55. Thus, while charge will build up on the capacitors 55 during the stimulation phase, the active recovery phase will recover that charge, particularly if the total amount of charge is equal in each phase (i.e., if the area under the stimulation and active recovery pulse phases are equal). Recovery of excess charge on the DC-blocking capacitors 55 is important to ensure that the DAC circuit 72 will operate as intended: if the charge/voltage across the DC-blocking capacitors 55 is not zero at the end of each pulse, remaining charge/voltage will skew formation of subsequent pulses, which may therefore not provide the prescribed amplitude.

During the stimulation phase, electrode E1 acts as the anode or source for the current pulse, while electrode E2 acts of the cathode or sink for the current pulse. Thus, sourced current of the desired amplitude is issued from the PDAC 72p to E1 while sunk current of that same amplitude is drawn into the NDAC 72n from E2. This causes the current to flow from E1 to E2 through the patient's tissue (R). Notice that the pulses at E1 and E2 during the stimulation phase have the same amplitude (although of opposite polarities) and the same pulse width (pw), so that an excess of charge does not build up in the patient's tissue, R. The stimulation phase is eventually followed by the active recovery phase during which E1 acts as the cathode (sunk current is drawn into the NDAC 72n from E1) and E2 as the anode (source current is issued from PDAC 72p to E2), such that current flows through the tissue R in the opposite direction.

To ensure complete recovery of any stored charge, the active recovery phase is followed by a passive recovery phase. In this passive recovery phase, the decoupling capacitors C1-C2 connected to previously-active electrodes E1 and E2 are shorted to a common potential via passive recovery switches 96 (FIG. 3A). In the example illustrated, this common potential, Vbat, comprises the voltage of the battery within the IPG 100, although other reference potentials could be used as well. Shorting the capacitors to Vbat effectively shorts them through the patient's tissue, and thus equilibrates any stored charge to assist in charge recovery. Some architectures may short only the previously-active electrodes by closing only the passive recovery switches 86 coupled to those electrodes, while other architectures will short all of the electrodes by closing all of the passive recovery switches 96.

Other pulse phases in each period are shown in FIG. 3B. Preceding the stimulation phase is a pre-pulse phase, which is of low amplitude and long duration, and of opposite polarity to the stimulation phase that follows it. Experimentation suggests that the use of such a pre-pulse can help to assist in recruiting deeper nerves in an SCS application, although use of such a pre-pulse is not strictly necessary. An interpulse period between the stimulation and active recovery phases of short duration allows the nerves to stabilize after being stimulated. A quiet phase follows the passive recovery phase, and essentially acts as a waiting phase before the next period issues. The duration of the quiet phase will depend on the durations of the phases that precede it in the period, as well as the frequency (f) at which the pulse issues.

The various phases of each pulse are controlled by the stimulation circuitry 70, which provides digital control signals to the DAC circuitry 72. The stimulation circuitry 70 receives and stores the data necessary to define the various phases in each pulse. Such information is provided to the stimulation circuitry 70 from microcontroller 50 via buses 90 and 92. The microcontroller in turn typically receives information about the structure of the pulses wirelessly from an external device, such as an external controller through which the patient or clinician could select the various pulse parameters (amplitude, pulse width, frequency), the electrodes, and whether they are to act as anodes or cathodes.

As illustrated in FIG. 3C, the stimulation circuitry includes a timer 94 and a register bank 98. The timer 94 stores the durations (pulse widths) of the phases in the pulse, while the register bank 98 stores control, amplitude, active electrode, and electrode polarity information for the phases. Thus, a first register in the timer 94 stores the pulse width of the first pulse phase in the period, the pre-pulse ($pw_{pp}$) in the example of FIG. 3B, and the corresponding first register in the register bank 98 stores its amplitude (amp pp), active electrode, and electrode polarities. A second register in the timer 94 stores the pulse width of the next pulse phase, the stimulation phase ($pw_s$), and the corresponding second register in the register bank 98 stores the amplitude ($amp_s$), active electrode, and electrode polarity for the stimulation phase. Data for subsequent pulse phases (interphase (ip), active recovery (ar), passive recovery (pr), and quiet (q)) are similarly stored in the timer 94 and register bank 98. The timer 94 may comprise a state machine in one example.

The control data in the registers ($cntl_x$) contains information necessary for proper control of the DAC circuitry 72 for each phase. For example, during the passive recovery phase, the control data ($cntl_{pr}$) would instruct certain passive recovery switches 96 to close, and would disable the PDAC 72p and the NDAC 72n. By contrast, during active phases, the control data would instruct the passive recovery switches 96 to open, and would enable the PDAC 72p and the NDAC 72n.

Each register in the register bank 98 is, in one example, 96 bits in length, with the control data for the phase in the first 16 bits, the amplitude of the phase specified in the next 16 bits, followed by eight bits for each electrode. Each of the eight electrode bits in turn specifies the polarity (P) of the electrode in a single bit, with the remaining 7 bits specifying the percentage (%) of the amplitude that that electrode will receive. Thus, for the pre-pulse phase, the polarity bit P for E1 would be a '1', specifying that that electrode is to act as a cathode, and thus will sink current of the specified amplitude (amp pp) to NDAC 72n. The remaining seven bits for E1 would digitally represent 100%, indicating that E1 is to receive the entirety of the cathodic current during the pre-pulse phase. In more complicated examples, the sourced or sunk currents could be shared between electrodes, and thus smaller percentages would be indicated in the trailing seven bits. The polarity bit P for E2 during the pre-pulse phase would be a '0', specifying that that electrode is to act as an anode, and thus will receive current as controlled by PDAC 72p. Again, the remaining seven bits for E2 would digitally represent 100%, indicating that E2 is to receive the entirety of the anodic current during the pre-pulse phase.

The other registers in register bank 98 are programmed similarly for each phase. For example, all of the bits for E3-E8 in all of the registers would be set to zero for the example pulses of FIG. 3B, because those electrodes are not implicated. The amplitudes for the interphase ($amp_{ip}$), passive recovery ($amp_{pr}$), and quiet ($amp_q$) phases would be set to zero as those phases do not require the PDAC 72p or NDAC 72n to actively issue any current.

The goal of the stimulation circuitry 70 is to send data from an appropriate register in the register bank 98 to the DAC circuitry 72 at an appropriate point in time, and this occurs by control of the timer 94. As noted earlier, the pulse widths of the various phases are stored in the timer 94. Also stored at the timer is the frequency, f, of the pulse, the inverse of which (1/f) comprises the duration of each period. Knowing this period, the timer 94 can cycle through the durations of each of the pulse widths, and send the data in the register bank 98 to the DAC circuitry 72 at the appropriate time. Thus, at the start of the period, the timer 94 enables the multiplexer 99 to pass the values stored in the first register for the pre-pulse data to the DAC circuitry 72 to establish the pre-pulse phase at electrodes E1 and E2. After time $pw_{pp}$ has passed, the timer 94 enables the multiplexer 99 to pass the values stored in the second register for the stimulation phase to the DAC circuitry 72 to establish the stimulation phase at the electrodes E1 and E2. The other registers are similarly controlled by the timer 94 to send their data at appropriate times. This process of cycling through the various pulse phases continues, and eventually at the end of quiet phase, i.e., at the end of $pw_q$, the timer 94 once again enables the pre-pulse data, and a new period of the pulse is established.

This approach for controlling the DAC circuitry 72 in accordance with each phase of the pulse period is adequate, but the inventors have found that this approach also suffers from certain shortcomings. A significant shortcoming is the lack of flexibility that the stimulation circuitry 70 provides to define more complex pulses. Because the parameters of each phase of a pulse are specified by dedicated registers in the register bank 98, pulses are limited to the number of phases that the register bank 98 is designed to accommodate (e.g., the six phases shown in FIGS. 3B and 3C) each of which specify a constant pulse amplitude. Therefore, more complex pulses having, for example, ramped portions cannot be created using the circuitry 70. The circuitry 70 could be modified to accommodate additional pulse phases to approximate ramped pulse portions using a stair-step approach, but this would require additional registers in the register bank 98. Assume, for example, that to form a suitably-smooth ramp it would be necessary to parse both of the stimulation and active recovery phases into ten smaller phases. The pulse would then comprise 24 different phases: the 20 phases needed in each of the stimulation and active recovery phases, the pre-pulse phase, the inter-pulse phase, the passive recovery phase, and the quiet phase. Because the register bank 98 must contain a register for each phase in the period, that bank 98 would then need 24 different registers. The 96 bits needed for each register in the bank 98 typically comprise flip flops, and so in this example 2304 (96*24) flip flops would be required, or more if the IPG 100 supports further numbers of electrodes.

Flip flops require significant layout area on the ASIC 60. Further, the flip flops consume power when they are clocked, which can lead to complexity in gating the clocks to save power. The problem of excessive layout space is compounded by the fact that the stimulation circuitry 70 may include multiple timer 94/register bank 98/multiplexer 99 units operating in parallel (although only a single example is shown). Based on the existing architecture, the ASIC 60 must either include an undue number of area-intensive registers in register bank 98 to potentially handle the design of complex pulses, or provide a limited number of such registers and forego the use of such complex pulses; neither option is desirable.

A better solution is therefore needed to address the aforementioned problems, and is provided by this disclosure.

BRIEF DESCRIPTION OF THE DRAWINGS

FIGS. 1A-1C show an implantable pulse generator (IPG), and the electrode arrays coupled to the IPG in accordance with the prior art.

FIG. 10 illustrates an example arrangement of microcode in an aggregate instruction that links a pulse program with a steering program in accordance with an embodiment of the disclosure.

FIG. 11 illustrates an example arrangement of aggregate instructions within a memory in accordance with an embodiment of the disclosure.

FIG. 12 illustrates the electrode configurations defined by example steering programs in accordance with an embodiment of the disclosure.

FIG. 19 illustrates the operation of a burst mode feature in accordance with an embodiment of the disclosure.

FIG. 20 illustrates the control signals generated by the stimulation circuitry in different scenarios in accordance with an embodiment of the disclosure.

FIG. 24 illustrates various types of triggers, issued upon the occurrence of different events by pulse definition circuits in the stimulation circuitry, which are utilized by the measure circuitry in accordance with an embodiment of the disclosure.

DETAILED DESCRIPTION

Figure 4A:
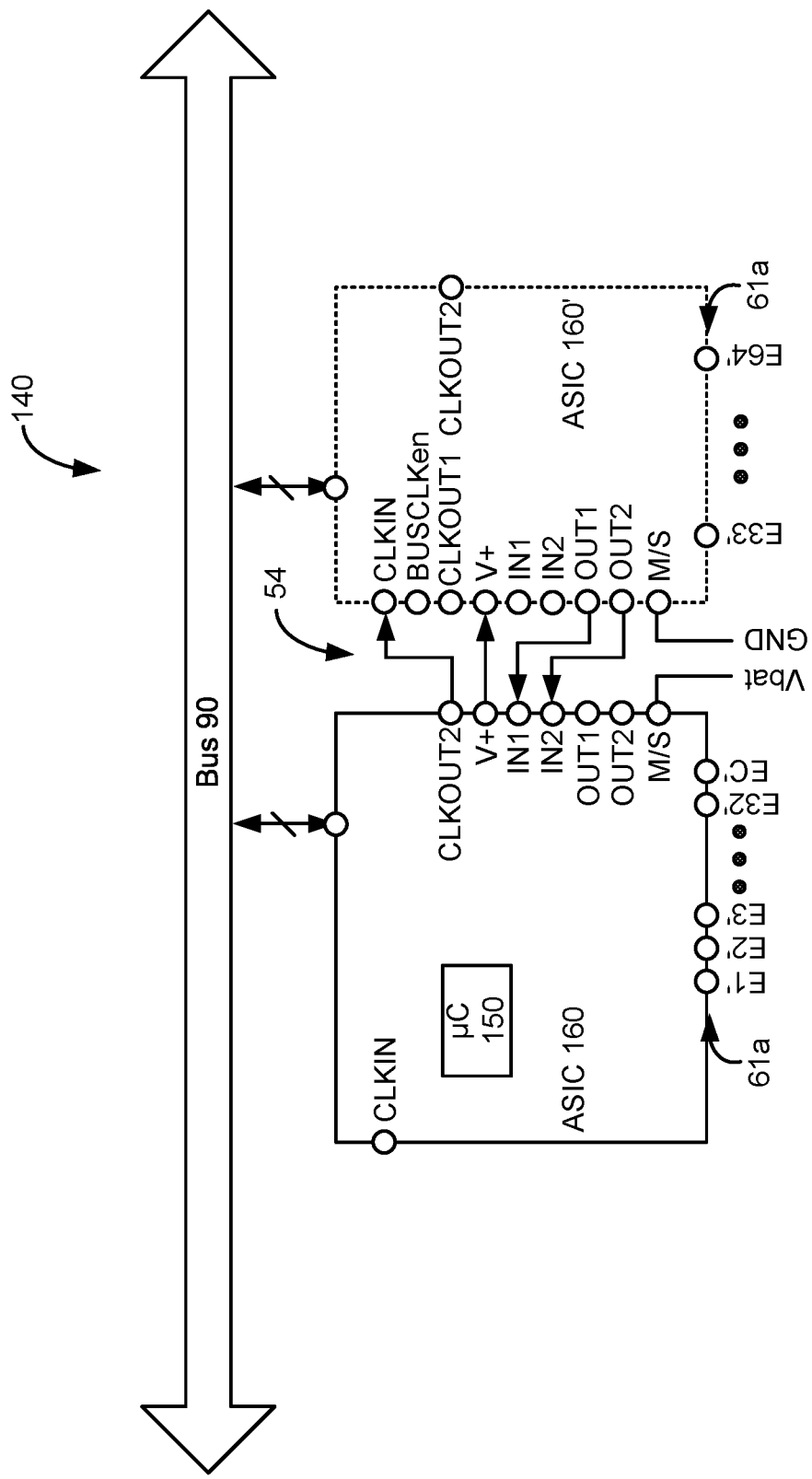
FIGS. 4A-4B show an improved architecture for the circuitry in an IPG in accordance with an embodiment of the disclosure.
Figure 4B:
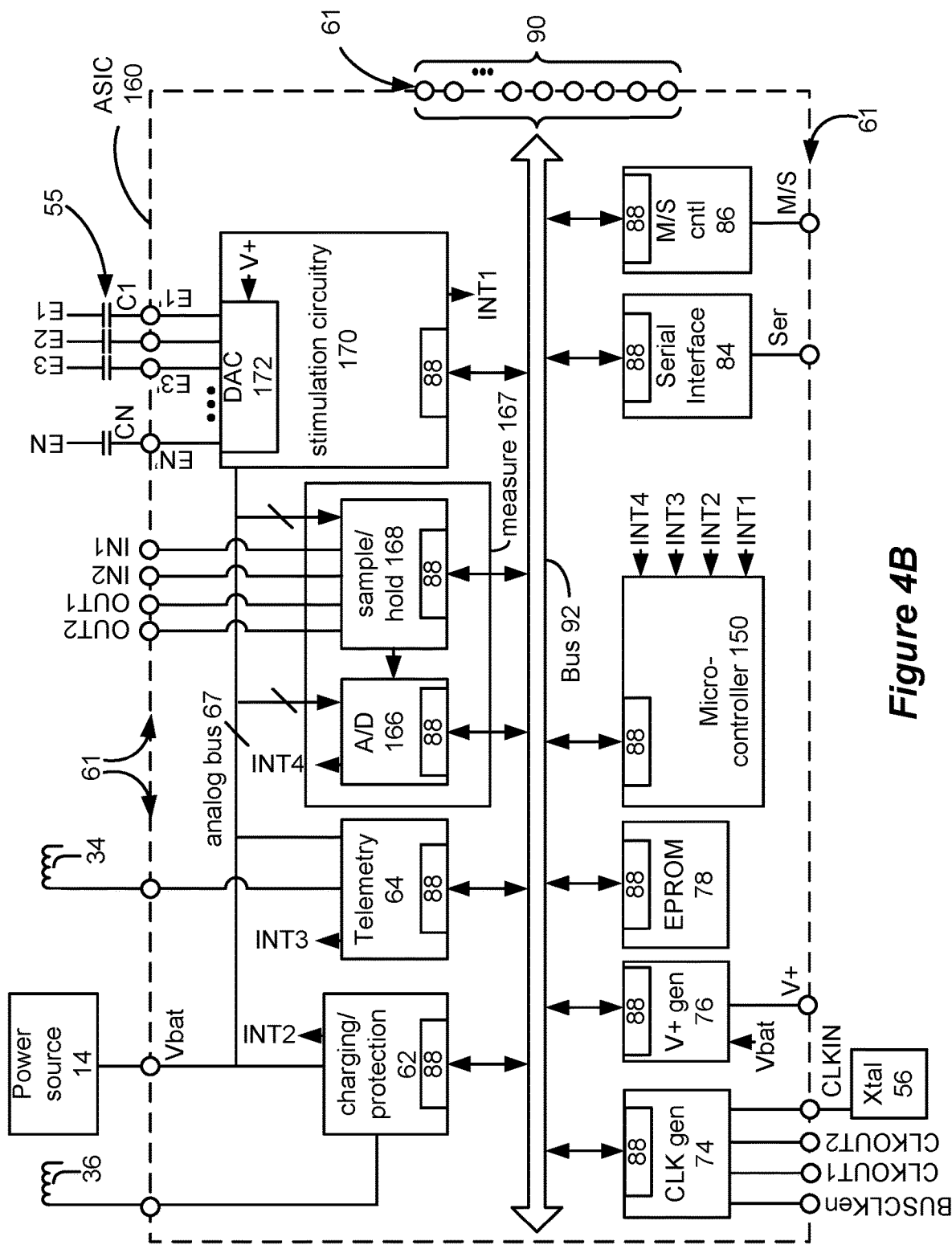

FIGS. 4A and 4B show an improved architecture 140 and ASIC 160 for an IPG. Elements in architecture 140 and ASIC 160 that can remain unchanged from the prior art architecture 40 and ASIC 60 described in the Background bear the same element numerals, and are not described again.

Improved ASIC 160 includes a microcontroller block 150, which as shown in FIG. 4B can communicate with other functional blocks in the ASIC 160 via internal bus 92. Microcontroller block 150 may receive interrupts independent of the bus 92 and its communication protocol, although interrupts may also be sent to the microcontroller 150 via the bus 92 as well. Even though ASIC 160 includes a microcontroller block 150, the ASIC 160 may still couple to an external bus 90, as shown in FIG. 4A. This can facilitate communications between the ASIC 160 and another device, such as a memory integrated circuit (not shown) that might be coupled to the bus 90. Bus 90 can also facilitate use of and communication with another identically-constructed ASIC 160', shown in dotted lines in FIG. 4A. As described in the Background, use of an additional (slave) ASIC 160' allows the number of electrodes 16 the IPG 10 supports to be doubled, and many of the same off-bus connections 54 can be used as described earlier, and as described in the above-referenced ASIC Publications. In one example, the microcontroller block 150 can comprise circuitry from an ARM Cortex-M0+ Processor, which may be incorporated into the monolithic integrated circuit of the ASIC 160 by licensing various necessary circuits from the library that comprises that processor.

Figure 5A:
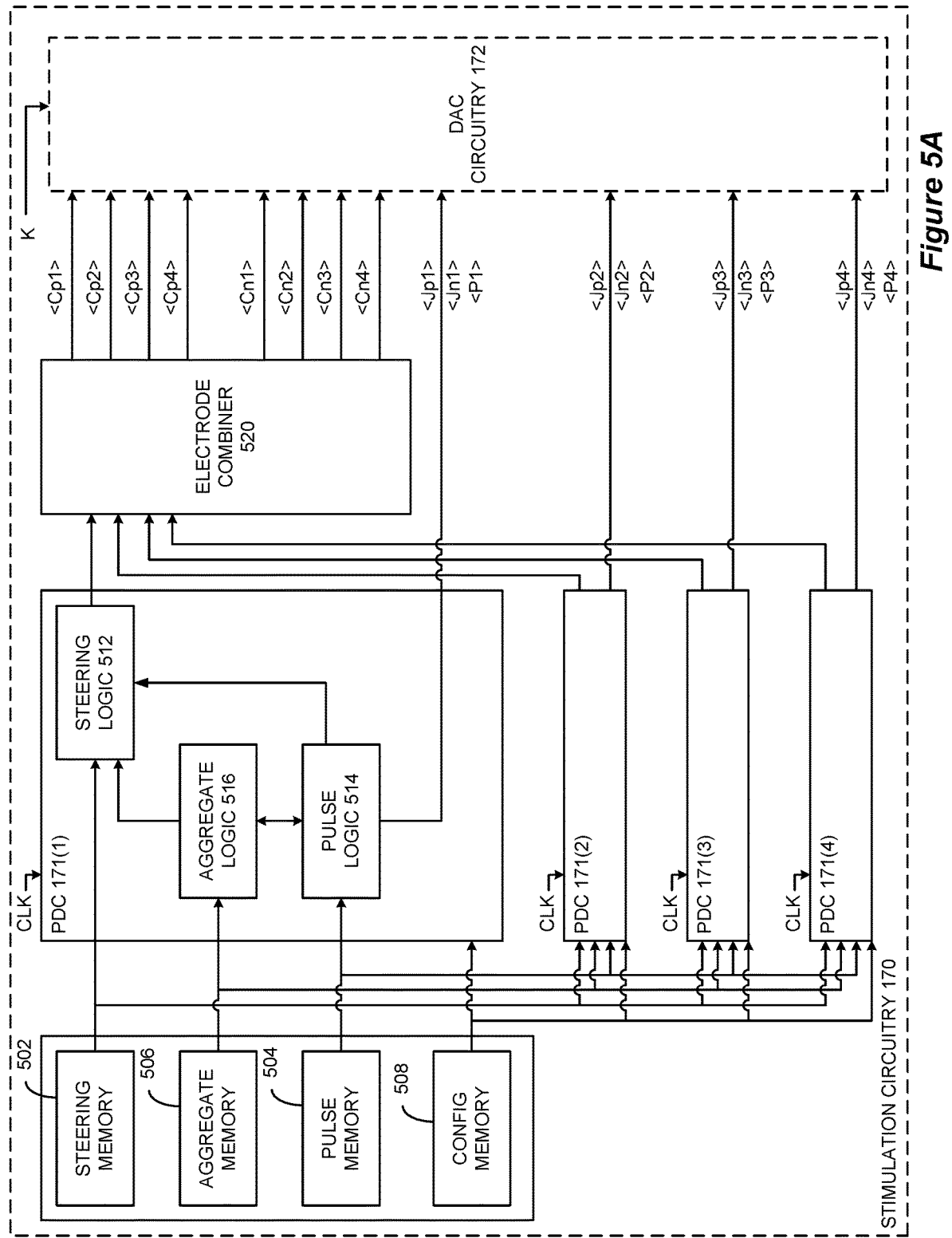
FIGS. 5A-5C illustrate components of the stimulation circuitry, including DAC circuitry, of the improved architecture in accordance with an embodiment of the disclosure.

Improved stimulation circuitry 170 is illustrated in block diagram form in FIG. 5A. In the improved stimulation circuitry 170, memory circuits store microcode that is processed by one or more pulse definition circuits (PDCs) 171, which operate as control circuits to generate the control signals that are sent to the DAC circuitry 172. The memory circuits include a steering memory 502 that contains steering microcode that defines electrode steering programs, a pulse memory 504 that contains pulse microcode that defines pulse programs, and an aggregate memory 506 that contains aggregate microcode that links pulse programs and steering programs to create a desired pulse therapy program. The stimulation circuitry 170 additionally includes a configuration memory 508 that stores configuration parameters some of which are global (apply across multiple PDCs 171) and some of which are specific to a particular PDC 171. The memories 502, 504, 506, and 508 can be read from and written to by the microcontroller 150, but, as described below, the microcode and configuration parameters in these memories can be processed by the PDCs 171 without intervention by the microcontroller 150. The microcontroller 150 is configured to operate in either a high-power state or a reduced-power state. The ability of the PDCs 171 to process the microcode and configuration parameters without intervention by the microcontroller 150 enables the microcontroller 150 to remain in the reduced-power state during the delivery of stimulation, which saves power in the IPG.

Each location (e.g., each 32-bit location) in the memories may be formed as a register of multiple flip-flops or as an addressable location in a more typical memory. Regardless of the structure, the microcode stored in the memories is generically described as being stored in memory circuitry, which memory circuitry may comprise separate memory circuits or a single memory circuit. The microcode and configuration parameters that are stored in the memory circuitry are processed by logic blocks in the PDCs 171 (four such PDCs are shown). These logic blocks include a steering logic block 512, a pulse logic block 514, and an aggregate logic block 516. Before returning to describe the control signals issued by the stimulation circuitry 170 to the DAC circuitry 172, the structure of the microcode and the configuration parameters and the processing of such microcode and configuration parameters by the logic blocks in PDCs 171 is described.

Figure 6:
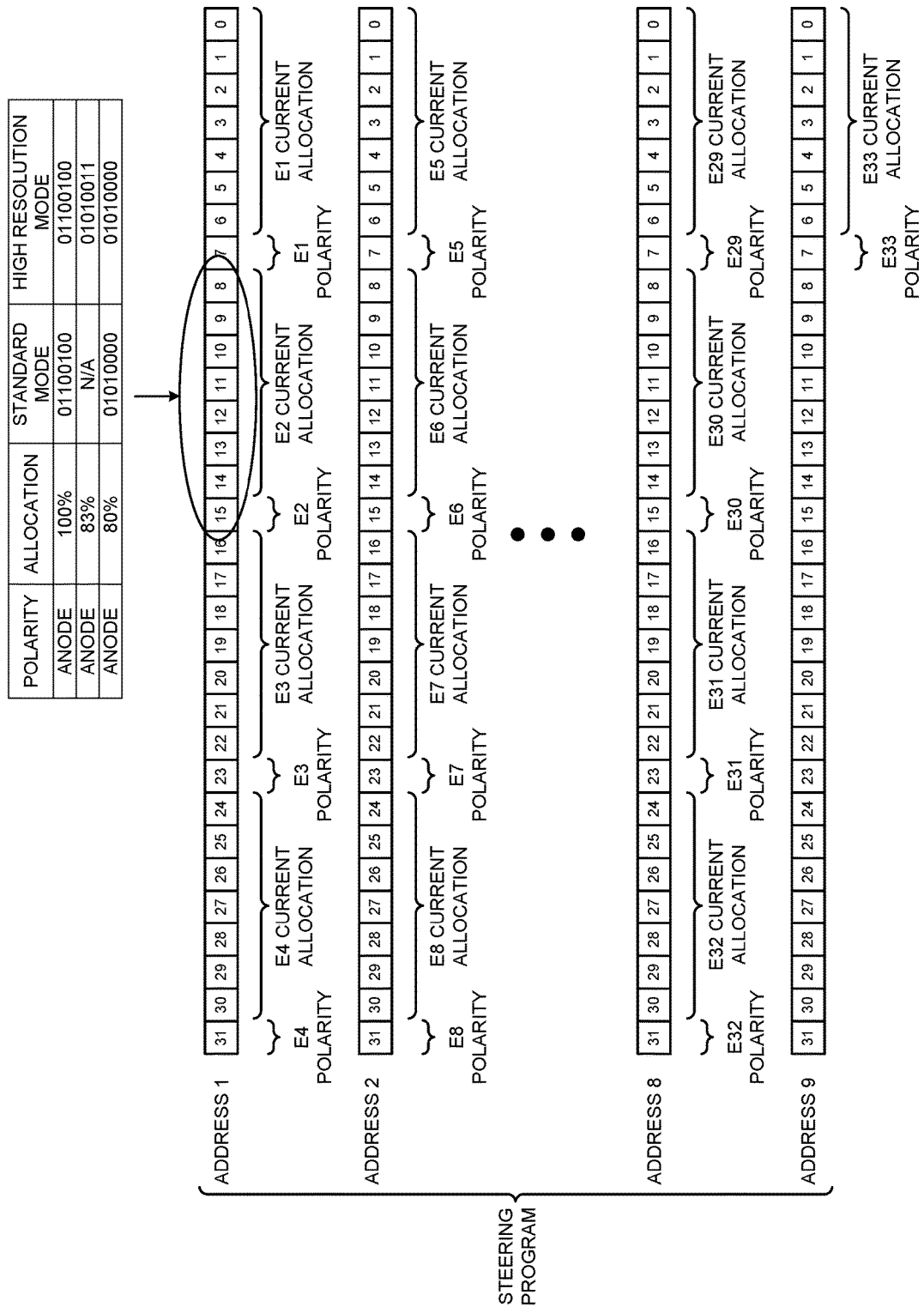
FIG. 6 illustrates an example arrangement of microcode to define a steering program in accordance with an embodiment of the disclosure.

FIG. 6 illustrates an example arrangement of microcode within memory locations within the steering memory to form a steering program that defines the polarity and current allocation for 33 electrodes (e.g., 32 lead electrodes and a case electrode). In the illustrated arrangement, each memory location includes 32 bits, and a steering program is defined by nine consecutive memory locations. For each electrode, the polarity and the allocation of current of the specified polarity is defined by one byte within one of the memory locations, and the bytes are arranged in consecutive order of the electrodes across the nine memory locations. In each byte, the most significant bit defines the electrode's stimulation polarity and the remaining bits (or some portion thereof) define the percentage of the total current of the specified polarity that is allocated to the electrode. An electrode's "stimulation polarity" as defined in the steering program refers to the polarity of the electrode during a stimulation pulse phase, which is opposite of the electrode's polarity during an active recovery pulse phase. For example, electrode E1 may be allocated 100% of the stimulation anodic current by setting bit 7 of address 1 to '0' and by providing a binary representation of 100% in bits 0-6 of address 1. Similarly, electrodes E2 and E5 may be allocated 25% and 75%, respectively, of the stimulation cathodic current by setting bit 15 of address 1 and bit 7 of address 2 to '1' and by providing a binary representation of 25% in bits 8-14 of address 1 and a binary representation of 75% in bits 0-6 of address 2. Note that while the example steering program defines each electrode's stimulation polarity, the steering program could alternatively define each electrode's active recovery polarity.

As will be described below, the resolution at which current can be allocated among the electrodes in the stimulation circuitry 170 can vary depending upon the mode of operation, and thus the number of bits within an electrode's seven-bit allocation range that are utilized can also vary based on the mode of operation. In a standard current mode, the stimulation circuitry 170 enables 4% resolution and only the five most significant bits in the seven-bit allocation range are used, but, in a high resolution current, the stimulation circuitry 170 enables 1% resolution and all seven bits in the seven-bit allocation range are used. As shown by the example allocations of anodic current to electrode E2, there is no difference in the bit patterns for these two modes of operation for the current allocations that are attainable in the first mode of operation (i.e., current allocations that are a multiple of 4%). While a single steering program is shown, multiple steering programs may be stored within the steering memory 502. For example, 16 different steering programs may be stored in 144 contiguous memory locations (e.g., a first steering program is defined by microcode in memory locations 1-9, a second steering program is defined by microcode in memory locations 10-18, and so on). The steering memory 502 thus stores a library of steering programs (each of which defines a particular electrode configuration) that can be used in conjunction with a pulse program as described below. It will be understood that the described steering program layout is merely illustrative and that the same features can be accomplished using different microcode arrangements.

Figure 7:
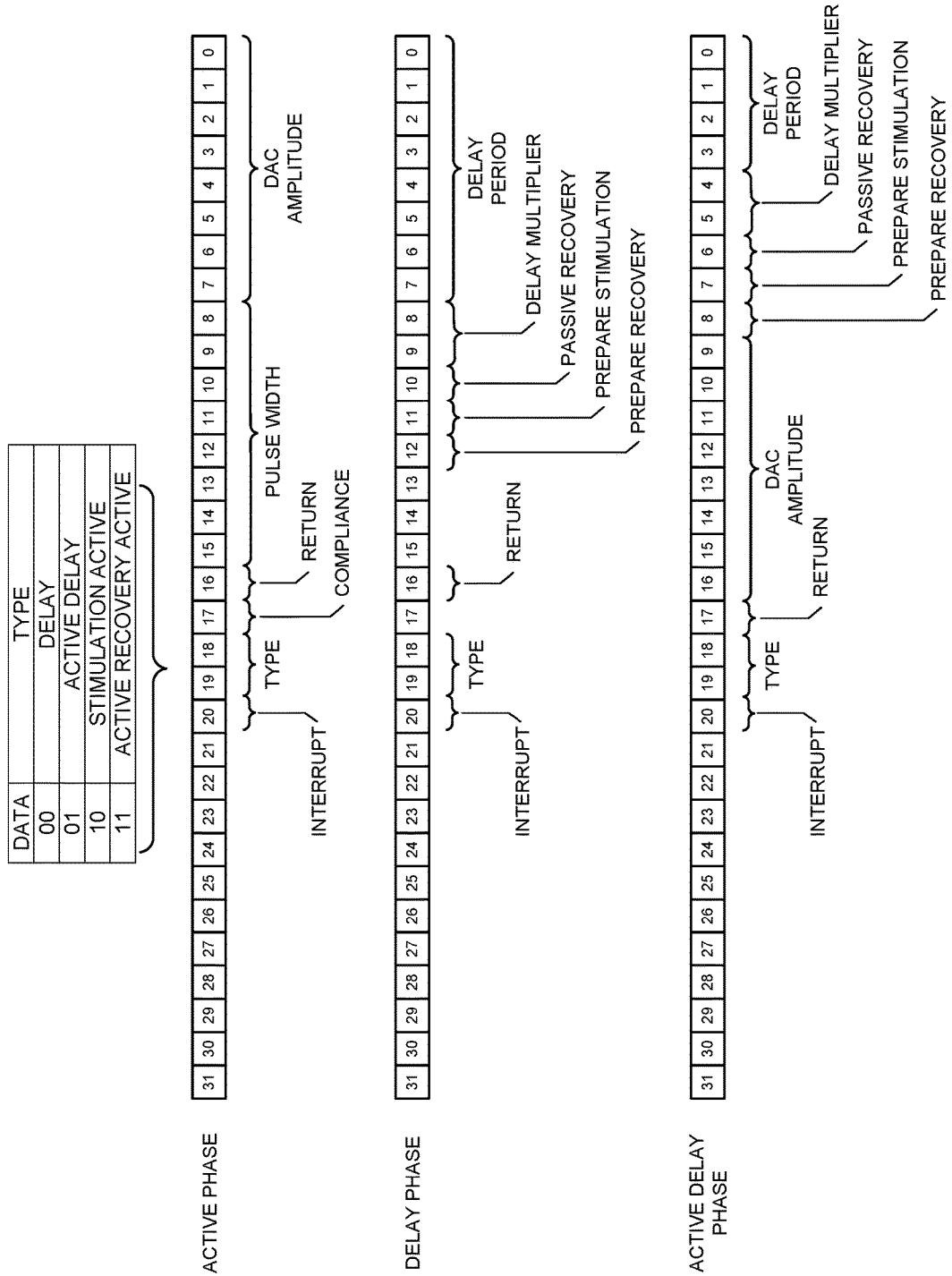
FIGS. 7-9 illustrate an example arrangement of microcode to define the parameters of individual phases of a pulse and the arrangement of instructions to define one or more pulse programs in accordance with an embodiment of the disclosure.

Having described an example arrangement of microcode within the steering memory 502 to define a steering program, we turn now to an example arrangement of microcode within the pulse memory 504 to define a pulse program, which example is illustrated with reference to FIGS. 7-9. In the example arrangement, each 32-bit memory location stores a pulse instruction that defines the properties of a single phase of the pulse. The arrangement of parameters for the different types of instructions (which define different types of phases) is illustrated in FIG. 7. The first type of instruction that is shown in FIG. 7 defines the parameters of an active phase. During an active phase, current is actively sourced from a PDAC 172*p* and sunk from an NDAC 172*n*. In the active phase instruction, bits 0-7 (i.e., the least significant byte) define an amplitude parameter of the active phase. The eight bits enable the assignment of 256 different amplitude values. In a preferred embodiment, the maximum current that can be delivered by the DAC circuitry 172 in conjunction with the execution of the pulse microcode is divided into 255 (i.e., the number of non-zero current values) units and the binary representation in the amplitude portion of the active phase instruction defines the quantity of those current units. For example, if the associated DAC circuitry 172 supports a maximum current of 25.5 mA, a binary representation of 100 units in the amplitude portion of the active phase instruction would specify a current amplitude of 10 mA.

The next byte (bits 8-15) in the active phase instruction defines the pulse width (i.e., the duration of the active phase). As with the amplitude portion of the active phase instruction, the eight bits in the pulse width range enable the assignment of 256 different pulse width values by providing a binary representation of the number of clock cycles over which the active phase extends. By way of example, for a 100 kHz clock, the value within the pulse width range can specify a pulse width from 0-2.55 milliseconds in 10 microsecond increments.

Bit 16 is a return bit that is set to '1' when the active phase is the last phase in a pulse program. Bit 17 is a compliance voltage bit that is set to '1' when it is desired to evaluate a status of the compliance voltage VH at the termination of the active phase. Bits 18 and 19 specify one of four different instruction types. The four types include a stimulation active phase instruction, an active recovery active phase instruction, a delay phase instruction, and an active delay phase instruction. A single active phase instruction arrangement is illustrated in FIG. 7 because the stimulation and active recovery active phase instructions differ only in the value in the type bit range. When the value in the type bit range corresponds to the stimulation active phase instruction, the active phase is applied in accordance with the steering program. However, when the value in the type bit range corresponds to the active recovery active phase instruction, the phase is applied with the opposite polarity of that specified in the steering program (i.e., the cathodic and anodic electrodes in the steering program are reversed). Bit 20 is an interrupt bit that is set to '1' when it is desired to provide an indication to the microcontroller 150 of the execution of the pulse phase. Such an interrupt may be communicated via the bus 92 or independent of the bus 92 via INT1, for example (FIG. 4B). The interrupt could be utilized to cause the microcontroller 150 to take a specified action (e.g., cause a measurement to be taken, update a steering program in the steering memory 502, etc.) at a time corresponding to the execution of the active phase.

The second type of instruction that is shown in FIG. 7 is a delay phase instruction. During a delay phase, no current is actively sourced or sunk by the DAC circuitry 172. In the delay phase instruction, bits 0-7 (i.e., the least significant byte) define the period of the delay. The eight bits in the delay range enable the assignment of 256 different delay period values by providing a binary representation of the number of time periods over which the delay phase extends. The time period can be the clock period, but bits 8 and 9 of the delay phase instruction are delay multiplier bits that enable the assignment of three additional time period values. For example, the four values that can be specified by the delay multiplier bits can represent the clock time period, the clock time period multiplied by 8, the clock time period multiplied by 16, and the clock time period multiplied by 256. Using these example multiplier values and a 100 kHz clock as an example, the period of the delay can be set from 0-2.55 milliseconds in 10 microsecond increments, from 0-20.4 milliseconds in 80 microsecond increments, from 0-40.8 milliseconds in 0.16 millisecond increments, or from 0-652.8 milliseconds in 2.56 millisecond increments. It will be understood that other delay multiplier values could be selected to achieve desired pulse characteristics.

Bit 10 of the delay phase instruction is a passive recovery bit that is set to '1' if passive recovery is to be performed during the delay phase. Bits 11 and 12 of the delay phase instruction are active stimulation and active recovery preparation bits, respectively. These bits can be used to signify that the next phase is either a first (prepare stimulation) or a second (prepare recovery) active phase type. This enables the PDC 171 to prepare the DAC circuitry 172 for the coming active phase. For example, if the prepare stimulation bit is set, the operational amplifiers 180 (FIG. 5C) corresponding to electrodes identified in the steering program as cathodic can be enabled in the NDAC 172n and the operational amplifiers 180 corresponding to electrodes identified in the steering program as anodic can be enabled in the PDAC 172p during the delay phase. The prepare recovery bit would obviously flip this behavior. Bits 16, 18-19, and 20 are return, type, and interrupt bits that function in the same manner as the corresponding bits of the active phase instruction.

The third type of instruction that is shown in FIG. 7 is an active delay phase instruction. An active delay phase is similar to a delay phase in that no current is actively sourced or sunk to the electrodes by the DAC circuitry 172. However, during an active delay phase, the current generation circuitry in the DAC circuitry 172 is maintained in an active state. As described below, this current generation circuitry includes the "master DAC" 185 (FIG. 5C), which mirrors a reference current to generate an amplified current in accordance with an issued amplitude control signal, and operation amplifiers 168. An active delay phase can be utilized, for example, during a short delay phase to set the amplitude value of the master DAC 185 to the value corresponding to the amplitude in a subsequent active phase and to enable the operational amplifier 168. Thus, while all electrode branch switches 178 (FIG. 5C) are open during an active delay phase such that no current is sourced to or sunk from any electrode, the current generation circuitry remains active so that the desired current in the subsequent pulse phase can be immediately delivered by closing the appropriate electrode branch switches 178. In the active delay instruction, bits 0-3 define the period of the delay and bits 4-5 define the delay multiplier. The delay period and the delay multiplier function in the same manner as the corresponding parameters of the delay phase instruction. However, the four-bit delay period of the active delay instruction enables 16 different delay period values by providing a binary representation of the number of time periods over which the delay phase extends. Using the same time period multipliers as described with respect to the delay phase instruction (i.e., 1, 8, 16, and 256) and a 100 kHz clock as an example, the period of the active delay can be set from 0-160 microseconds in 10 microsecond increments, from 0-1.28 milliseconds in 80 microsecond increments, from 0-2.56 milliseconds in 0.16 millisecond increments, or from 0-40.96 milliseconds in 2.56 millisecond increments. Bits 6, 7, and 8, are passive recovery, prepare stimulation, and prepare recovery bits, which function in the same manner as the corresponding bits in the delay phase instruction. Bits 9-16 define the amplitude value and function in the same manner as the corresponding data in the active phase instruction. As described above, this value would logically be set to the amplitude of the current to be delivered in the immediately succeeding active phase such that the DAC circuitry 172 is prepared to deliver the specified current even though the electrode branch switches 178 are open during the active delay phase. Bit 17 is a return bit, bits 18 and 19 are type bits, and bit 20 is an interrupt bit, each of which functions in the same manner as corresponding bits in the active phase and delay phase instructions.

Figure 8:
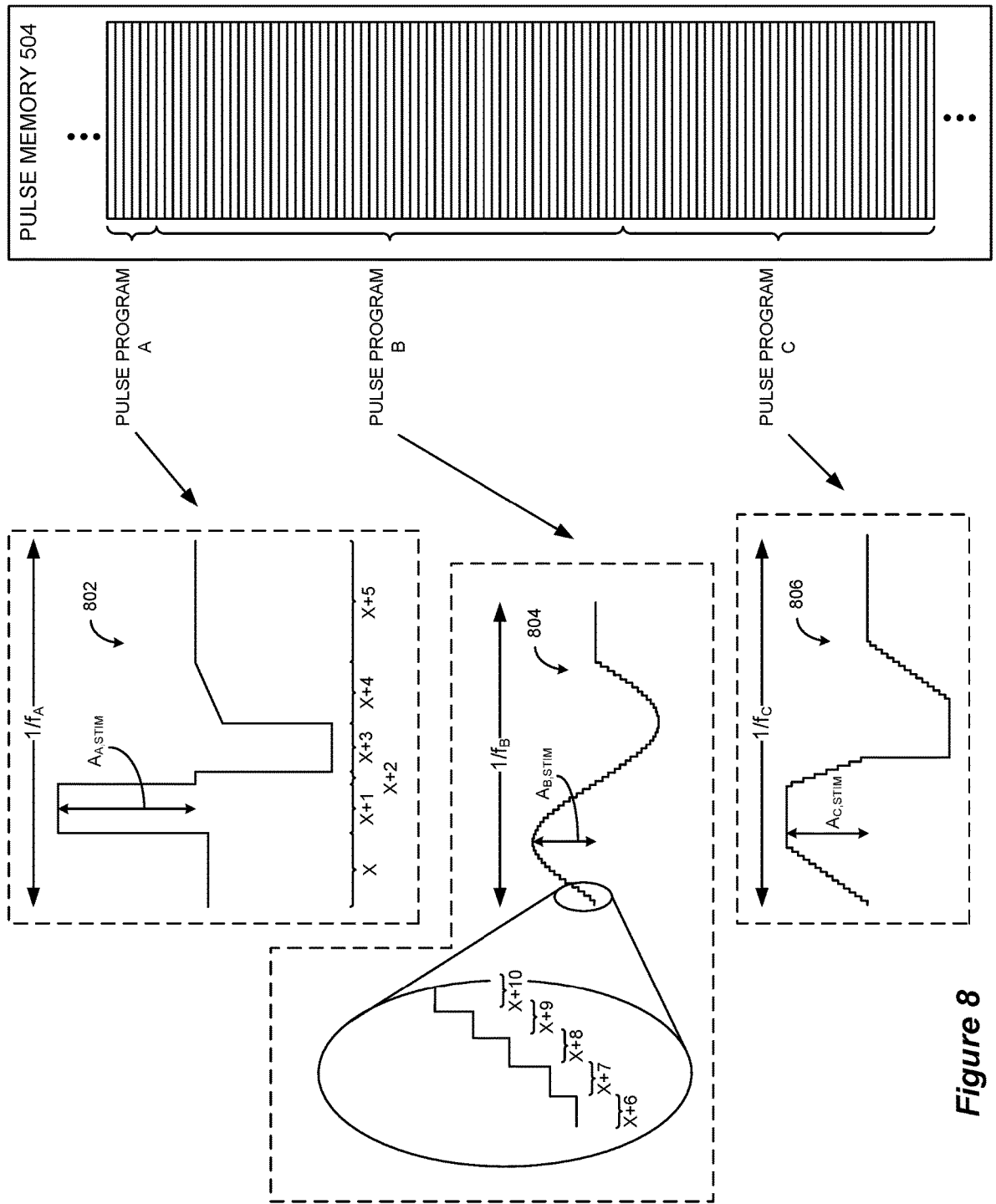

As illustrated in FIG. 8, the different types of instructions are arranged in contiguous memory locations in the pulse memory 504 to create pulse programs. Each pulse program consists of the instructions that define the phases in a single period of a pulse. For example, pulse program A defines the pulse 802, which was described in the background section. FIG. 9 illustrates the configuration of pulse program A's six instructions, each of which defines the parameters of one of the pulse 802's phases. In addition, FIG. 9 illustrates the linkage of pulse program A with a steering program A to apply the pulse 802 to electrodes E1 and E2 in the same manner as described in the background section. Steering program A specifies that electrode E1 is to receive 100% of the stimulation anodic current and that electrode E2 is to receive 100% of the stimulation cathodic current of the pulse defined by the pulse program.

The first phase in the pulse 802 is the pre-pulse phase, which is defined by the instruction at memory location X in pulse program A. Because the pre-pulse phase has a non-zero amplitude of A1, current is actively driven by the DAC circuitry 172 during this phase. Thus, the instruction at memory location X is configured as an active phase instruction. More specifically, the instruction is configured as an active recovery active phase instruction (bits 18-19), which reverses the polarity of the electrodes defined by steering program A such that electrode E1 operates as a cathode (current sink) and electrode E2 operates as an anode (current source) during the pre-pulse phase. The instruction at memory location X additionally specifies the amplitude A1 (bits 0-7) and the pulse width PW1 (bits 8-15) of the pre-pulse phase and specifies that the pre-pulse phase is not the last phase in pulse program A (bit 16) and that no compliance voltage measurement is to be taken (bit 17) and no interrupt is to be issued (bit 20) in association with the pre-pulse phase.

The stimulation phase of pulse 802 is defined by the instruction at memory location X+1. This instruction is also configured as an active phase instruction, but it is configured as a stimulation active phase instruction (bits 18-19), which utilizes the polarities defined by steering program A such that electrode E1 operates as an anode (current source) and electrode E2 operates as a cathode (current sink) during the stimulation phase. The instruction at memory location X+1 additionally defines the amplitude A2 (bits 0-7) and the pulse width PW2 (bits 8-15) of the stimulation phase and specifies that the stimulation phase is not the last phase in pulse program A (bit 16) and that no compliance voltage measurement is to be taken (bit 17) and no interrupt is to be issued (bit 20) in association with the stimulation phase.

The inter-pulse phase is defined by the instruction at memory location X+2. Because the amplitude during the inter-pulse phase is zero and the inter-pulse phase is of a short duration and followed by an active phase, the instruction at memory location X+2 is configured as an active delay phase instruction (bits 18-19), which, as described above, enables the current generation circuitry in the DAC circuitry 172 to be enabled and set to the amplitude of the subsequent phase. The instruction at memory location X+2 defines the pulse width PW3 of the inter-pulse phase (bits and the amplitude A4 of the succeeding active recovery phase (bits 9-16) and specifies that no passive recovery is to be performed during the inter-pulse phase (bit 6), that the inter-pulse phase is not the last phase in pulse program A (bit 17), and that no interrupt is to be issued (bit 20) in association with the inter-pulse phase. The instruction additionally specifies that the succeeding phase is an active recovery active phase (bits 7-8), which enables the operational amplifiers 180 to be enabled based on the opposite of the polarities defined by the steering program A. While the inter-pulse phase is illustrated as being configured using an active delay phase instruction, it could also be configured using a delay phase instruction.

The active recovery phase is defined by the instruction at memory location X+3. The instruction at memory location X+3 is configured as an active recovery active phase instruction (bits 18-19) and defines the amplitude A4 (bits 0-7) and the pulse width PW4 (bits 8-15) of the active recovery phase. Memory location X+3 additionally specifies that the active recovery phase is not the last phase in pulse program A (bit 16) and that no compliance voltage measurement is to be taken (bit 17) and no interrupt is to be issued (bit 20) in association with the active recovery phase.

The passive recovery and quiet phases are defined by the instructions at memory locations X+4 and X+5, respectively. The instructions at memory locations X+4 and X+5 are configured as delay phase instructions (bits 18-19) that define the pulse widths PW5 and PW6 (bits 0-9) of the passive recovery and quiet phases, respectively. These instructions additionally specify that there is no subsequent pulse phase (bits 11-12) and that no interrupt is to be issued (bit 20) in association with the passive recovery or quiet phases. The instructions in memory locations X+4 and X+5 differ only in that the former specifies that passive recovery is to be performed (bit 10) during the passive recovery phase and the latter specifies that the quiet phase is the final phase (bit 16) of the pulse program A.

Referring back to FIG. 8, in addition to the simple types of biphasic pulses (such as pulse 802) that can be configured using the prior art stimulation circuitry 70, the instructions in the pulse memory 504 can also be configured to create more complex pulse programs. For example, pulse program B defines pulse 804, which mimics a sine wave, and pulse program C defines pulse 806, which includes multiple ramp portions. Pulse program B is created by 58 contiguous instructions in the pulse memory 504, one instruction for each of the 58 phases in a single period of pulse 804, which instructions begin immediately following the final instruction associated with pulse program A. The first phase of pulse 804 is defined by the instruction at memory location X+6, and the final phase of pulse 804 is defined by the instruction at memory location X+63. The first phase of pulse 806 is defined by the instruction at memory location X+64, and the final phase of pulse 806 is defined by the instruction at memory location X+101. As will be understood, the "smoothness" of a curve that is approximated using constant-current phases (as in the pulse 804, for example) is improved by increasing the number of phases and decreasing the phase pulse width.

Note that the configurability of the pulse instructions and in their arrangement within the pulse memory 504 enables the creation of pulses having practically any imaginable properties. In addition to the different types of pulse shapes, the pulses 802, 804, and 806 have different durations ($1/f_A$, $1/f_B$, and $1/f_C$, respectively) and maximum stimulation amplitudes ($A_{A,STIM}$, $A_{B,STIM}$, and $A_{C,STIM}$, respectively), which properties may differ significantly (even though the pulses are shown at different scales that suggest the properties are closer in value). Moreover, any number of different pulse programs can be created within the space limitations of the pulse memory 504, which may include, for example, 256 memory locations or more. The pulse memory 504 thus stores a library of pulse programs (each of which defines a pulse shape) that can be used in combination with the steering programs by the PDCs 171 to generate desired stimulation waveforms. A stimulation waveform is the pattern of stimulation across a set of active electrodes.

Figure 9:
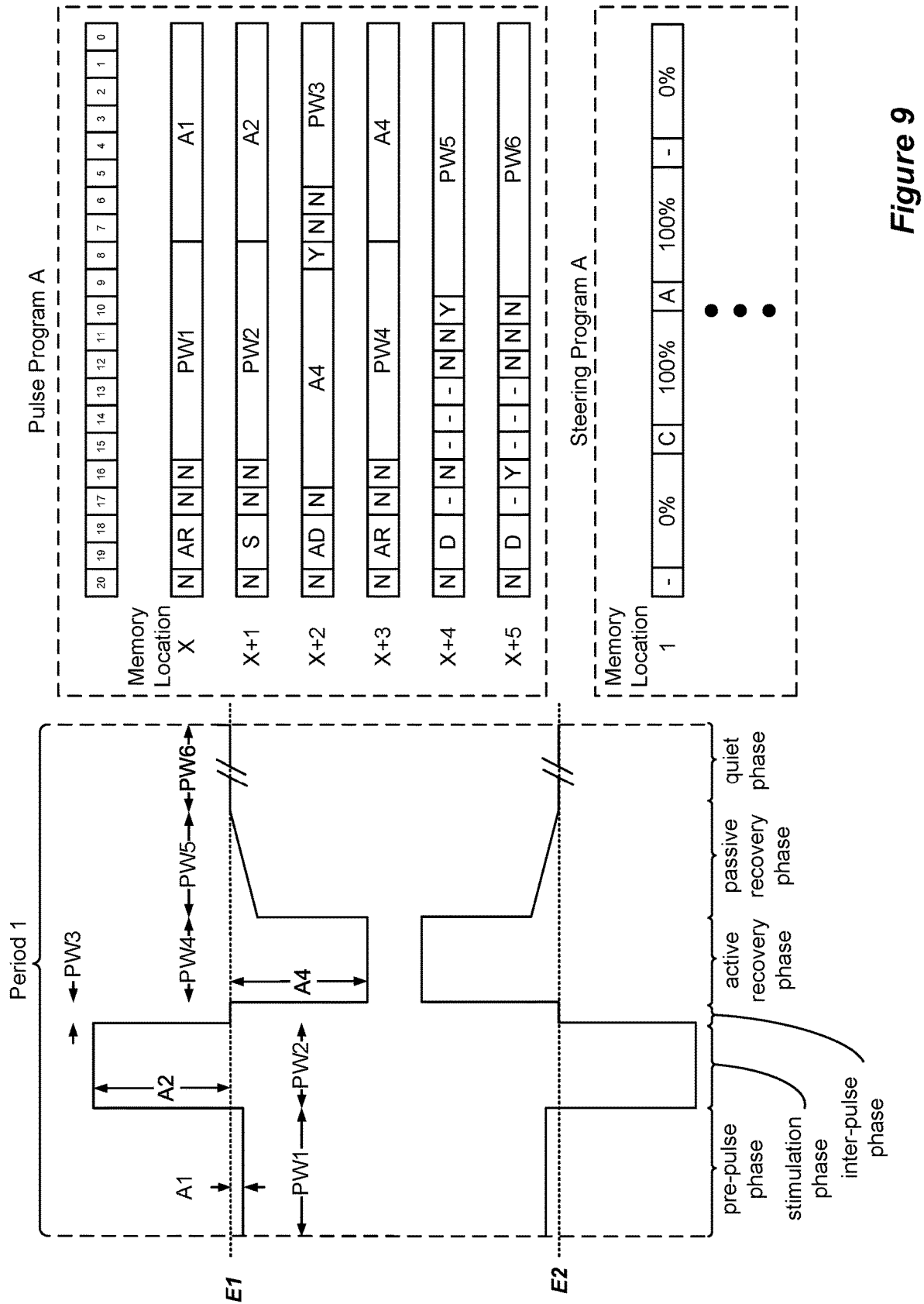

FIG. 9 described the linkage of a pulse program with a steering program. This linkage is accomplished through the configuration of aggregate instructions in the aggregate memory 506. FIG. 10 shows an example arrangement of an aggregate instruction. The first eight bits (bits 0-7) in an aggregate instruction specify the starting pulse memory address. To execute pulse program A, for example, the pulse address portion of the aggregate instruction would include a binary representation of the numeric address of X in the pulse memory 504. Bits 8-11 of the aggregate instruction specify the steering program to be linked with the pulse program. The four bits in the steering program portion of the aggregate instruction enable the selection of 16 different steering programs. This range of bits could obviously be extended to accommodate additional steering programs. Bits 12-19 enable specification of the number of times that the selected pulse is to be repeated. The eight bits in this repeat range enable the specification of up to 255 repeats. As described below, execution of the aggregate instruction results in the sequential execution of the instructions in a pulse program starting at the address specified in the aggregate instruction and ending at the subsequent "return" instruction in the pulse memory 504. This sequential execution is repeated the number of times specified in the repeat range of the aggregate instruction. While it may be typical for the specified pulse memory address to correspond to the first phase of a pulse program such that the executed pulse corresponds to a complete pulse program, this is not strictly necessary. Bit 20 specifies whether an interrupt is to be executed following execution of the aggregate instruction.

Any one or more aggregate instructions represent an aggregate program that defines a stimulation waveform. Note that while the starting and ending addresses in an aggregate program are specified as configuration parameters of an individual PDC 171, the aggregate instruction arrangement could also include a return bit such that the instruction itself identifies that it is the final instruction in a program similar to the return bit in a pulse program.

FIG. 11 illustrates the arrangement of aggregate instructions within the aggregate memory 506. In the example configuration illustrated, the instruction at memory location Y specifies the linkage of pulse program A (which begins at pulse memory address X) with steering program A for two repetitions with no interrupt, the instruction at memory location Y+1 specifies the linkage of pulse program A with steering program B for five repetitions with no interrupt, the instruction at memory location Y+2 specifies the linkage of pulse program B (which begins at pulse memory address X+6) with steering program C for 13 repetitions with no interrupt, the instruction at memory location Y+3 specifies the linkage of pulse program A with steering program C for five repetitions with no interrupt, the instruction at memory location Y+4 specifies the linkage of pulse program C (which begins at pulse memory address X+64) with steering program D for five repetitions with no interrupt, and the instruction at memory location Y+5 specifies the linkage of pulse program B with steering program D for seven repetitions with no interrupt. The aggregate memory 506 stores a library of aggregate instructions. One or more aggregate instructions define an aggregate program, which program's start and end addresses (i.e., start and end instructions) are defined by the configuration parameters of an individual PDC 171. An aggregate program, by way of its linkage of one or more pulse programs with one or more steering programs, is a program that, when executed, generates a stimulation waveform in accordance with its underlying pulse and steering programs.

FIG. 12 shows the parameters of the steering programs that are listed in conjunction with FIG. 11. Steering program A, as described above, specifies that electrode E1 is to receive 100% of the stimulation anodic current and electrode E2 is to receive 100% of the stimulation cathodic current. Steering program B specifies that electrodes E1 and E2 are to receive 40% and 60% of the stimulation anodic current, respectively, and electrode E3 is to receive 100% of the stimulation cathodic current. Steering program C specifies that electrode E4 is to receive 100% of the stimulation anodic current and electrode E5 is to receive 100% of the stimulation cathodic current. Steering program D specifies that electrode E4 is to receive 100% of the stimulation anodic current and electrodes E5 and E6 are to receive 80% and 20% of the stimulation cathodic current, respectively. The example aggregate instructions shown in FIG. 11 and the example steering programs shown in FIG. 12 are referenced in the description and figures that follow.

Figure 13:
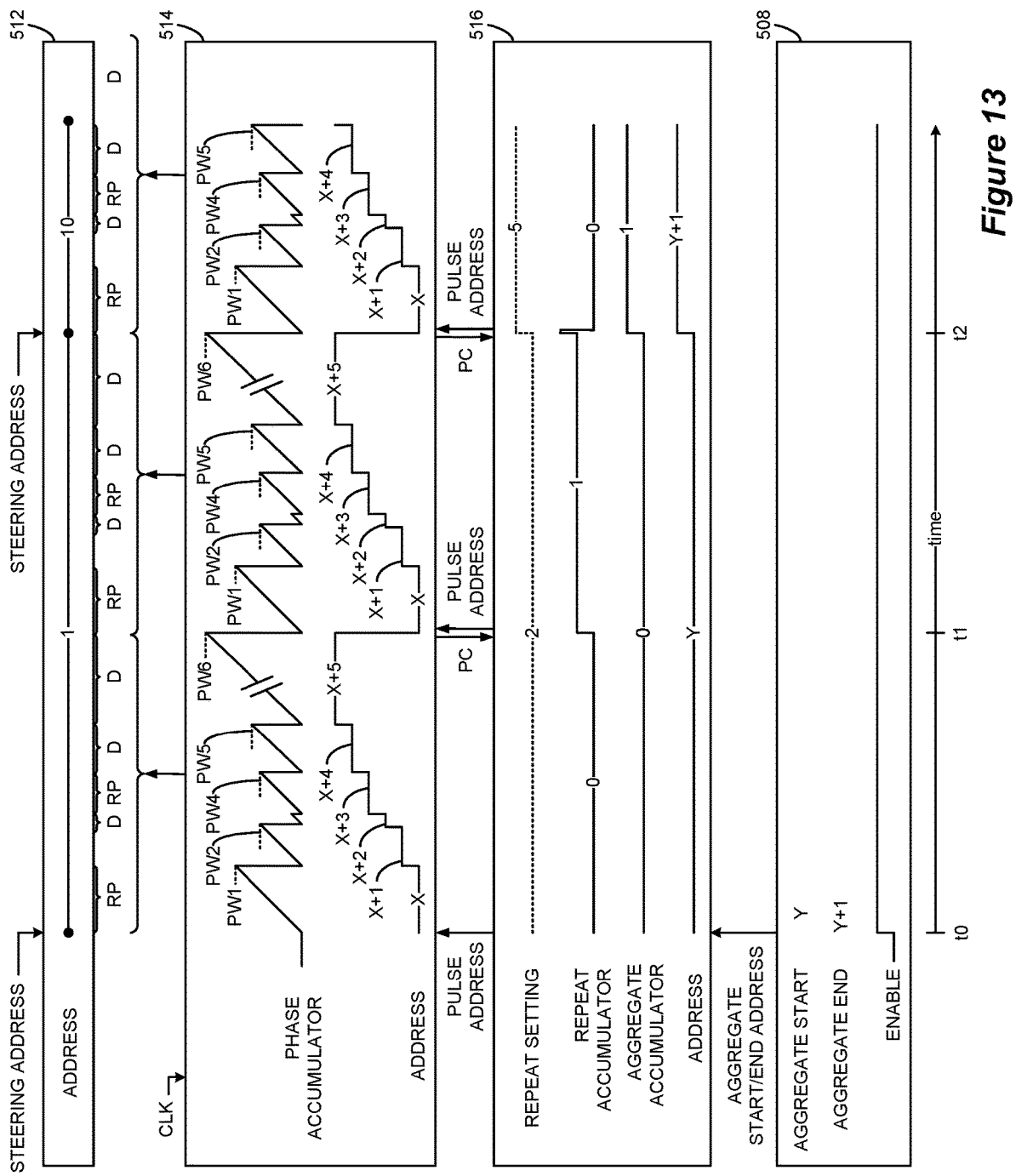
FIG. 13 is a timing diagram that illustrates the execution of instructions by various logic blocks in a pulse definition circuit in accordance with an embodiment of the disclosure.

Having described the arrangement of the steering, pulse, and aggregate microcode, we turn now to the operation of the aggregate logic block 516, pulse logic block 514, and steering logic block 512 in executing such microcode to deliver control signals to the DAC circuitry 172 at the appropriate times. FIG. 13 is a timing diagram that shows the values of various parameters of the aggregate logic block 516, pulse logic block 514, and steering logic during block 512 execution of an example portion of an aggregate program. As will be understood, execution of an aggregate program involves execution of the corresponding pulse and steering programs. At time t0, PDC 171(1) is enabled. The pulse definition enable bit is a parameter of configuration memory 508 and is specific to PDC 171(1). In response to the PDC being enabled, its aggregate logic block 516 retrieves the aggregate instruction start and end addresses, which addresses are also specific to PDC 171(1) and stored in memory 508. In the example shown, the aggregate start and stop addresses are Y and Y+1, respectively. Therefore, when enabled, the aggregate logic block 516 in PDC 171(1) executes the instructions stored between these addresses in the aggregate memory 506. The aggregate logic block 516 initially retrieves and decodes the instructions stored at the aggregate start address (Y) in the aggregate memory 506. As illustrated in FIG. 11, the instruction stored at aggregate address Y links pulse program A (which begins at pulse memory address X) and steering program A for 2 repetitions. The aggregate logic block 516 stores the repeat setting (2) and provides the pulse memory address (X) to the pulse logic block 514 and the steering memory address (steering program A corresponds to address 1) to the steering logic block 512, which logic blocks retrieve the microcode from the respective addresses.

The pulse logic block 514 manages the sequencing of the individual phases of the pulse program. This is accomplished by maintaining a phase accumulator that is incremented in accordance with the system clock (CLK) and any clock multiplier parameters in the pulse instruction that is being processed. As shown in the example in FIG. 13, upon retrieval of the pulse instruction at address X, the pulse logic block 514 begins incrementing the phase accumulator. As described above, the instruction at address X defines an active phase and does not include a clock multiplier parameter. Accordingly, the phase accumulator is incremented by one with each clock cycle until the accumulated value is equal to the pulse width value specified by the instruction (PW1). When the accumulated value is equal to the pulse width value and the instruction is not defined as the last phase in a pulse program (i.e., the instruction's return bit is not set), the pulse logic block 514 increments its address parameter and obtains the instruction stored at the new address value in the pulse memory 504, clears the phase accumulator value, and repeats the process for the retrieved instruction. This process continues as the pulse logic block 514 moves sequentially through the addresses associated with the pulse program.

In addition to managing the sequencing of the individual phases of the pulse program, the pulse logic block 514 additionally communicates signals to the steering logic block 512 when the instruction being executed by the pulse logic block 514 necessitates a modification to the steering program. For example, as described above, during an active recovery phase, the electrode polarities are reversed from the polarities indicated in the steering program. Thus, during execution of an active recovery active phase instruction, the pulse logic block 514 communicates a reverse polarity ("RP") signal to the steering logic block 512. Similarly, during any delay phase, no current is sourced to or sunk from an electrode, and this information must also be communicated to the steering logic block 512. During execution of a delay phase instruction, the pulse logic block 514 communicates a delay ("D") signal to the steering logic block 512.

When the pulse logic block 514 completes the processing of an instruction that defines the last phase in a pulse program (i.e., when the instruction's return bit is set and the phase accumulator's accumulated value is equal to the specified pulse width), the pulse logic block 514 communicates a pulse complete ("PC") indication to the aggregate logic block 516. In the example shown this occurs at time t1.

In response to the receipt of the pulse complete indication from the pulse logic block 514, the aggregate logic block 516 increments its repeat accumulator value (from 0 to 1 at t1). The repeat accumulator value is initialized to zero prior to the execution of each new aggregate instruction and represents the number of times that a specified pulse has been executed for the current aggregate instruction. Aggregate logic block 516 then compares its repeat accumulator value (1) to the repeat setting (2) and determines that, because the repeat accumulator value is still less than the repeat setting, the pulse specified is to be repeated. Accordingly the aggregate logic block 516 provides the pulse memory address that is specified as the aggregate start address (X) to the pulse logic block 514 again. Because there hasn't been a change in the aggregate instruction as a result of the pulse completion (i.e., the repeat accumulator value has not reached the repeat setting), the steering address is unchanged and is therefore not provided to the steering logic block 512 again. In response to the receipt of the pulse memory address, the pulse logic block 514 sequentially executes the instructions from pulse memory address X to pulse memory address X+5 in the same manner as before. When the pulse logic block 514 completes the execution of the instruction at pulse memory address X+5 (which corresponds to the last phase in pulse program A), the pulse logic block 540 again issues a pulse complete signal to the aggregate logic block 516. In the example shown this occurs at time t2.

As before, the aggregate logic block 516 increments its repeat accumulator value (from 1 to 2 at t2) and compares the incremented value to the repeat setting. In this instance, the repeat accumulator value is equal to the repeat setting, which signifies the completion of the current aggregate instruction. As a result, the aggregate logic block 516 determines whether its current address is equal to the aggregate end address. If the current aggregate address is equal to the aggregate end address, the aggregate logic block 516 reverts to the aggregate start address, but if the current aggregate address is not equal to the aggregate end address, the aggregate logic block 516 increments the aggregate address. In either case, the aggregate logic block 516 additionally increments its aggregate accumulator value, which value represents the number of aggregate instructions that have been executed since the PDC 171 was enabled. Because, in this case, the current aggregate address (Y) is not equal to the aggregate end address (Y+1), the aggregate logic block 516 increments its address value and retrieves and decodes the instruction stored at the incremented address value (Y+1) of the aggregate memory 506.

As illustrated in FIG. 11, the instruction stored at aggregate memory location Y+1 links pulse program A (which begins at pulse address X) and steering program B for 5 repetitions. The aggregate logic block 516 stores the repeat setting (5) and provides the pulse memory address (X) to the pulse logic block 514 and the steering memory address (steering program B corresponds to address 10) to the steering logic block 512, which logic blocks retrieve the microcode from the respective addresses. While the aggregate instruction at address Y specifies the same pulse memory starting address (X) as does aggregate instruction at address Y+1, this will not always be the case. For example, the transition between aggregate instructions at addresses Y+1 and Y+2 results in the execution of a different pulse program. Thus, while the example illustrated in FIG. 13 depicts the execution of the same pulse program after a transition between aggregate instructions, such transition may commonly result in the provision of an entirely different pulse memory address to the pulse logic block 514.

As will be understood from the diagram in FIG. 13, aggregate instructions are executed by the aggregate logic block 516 as an outer loop program, which specifies the parameters of an inner loop program. The parameters of the inner loop program that are specified by the outer loop program include the pulse memory address and the steering memory address. The inner loop program is executed by the pulse logic block 514 in conjunction with the steering logic block 512. As will be understood, the sequencing provided by the outer loop and inner loop programs ensure that the active instructions are referenced by the respective logic blocks at any given time. As will be described below, this sequencing operation enables the control signals that are provided to the DAC circuitry 172 to be determined at a given time based upon the active instructions. It should also be appreciated that, as described above, the sequencing operations that are performed by the stimulation circuitry 170 do not rely on the microcontroller 150. Therefore, sequencing can be performed while the microcontroller 150 operates in the reduced-power mode, which saves power in the IPG.

Figure 14:
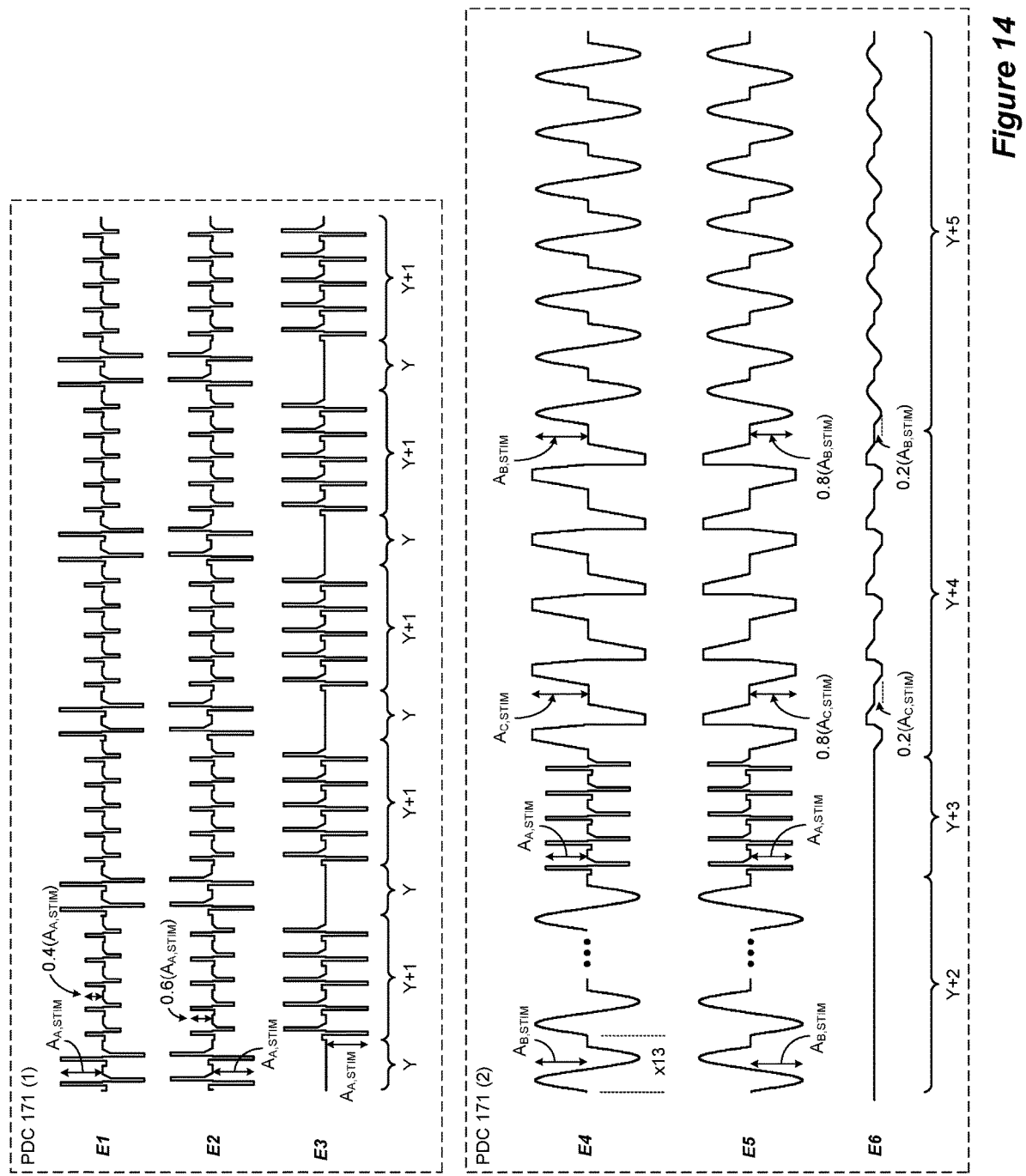
FIG. 14 illustrates the stimulation waveforms generated simultaneously by two different pulse definition circuits executing two different aggregate programs in accordance with an embodiment of the disclosure.

FIG. 14 shows the pulse pattern at electrodes E1, E2, and E3 as a result of the execution of the example aggregate program in FIG. 13. During execution of the aggregate instruction at memory location Y, pulse program A is repeated twice with 100% of the stimulation anodic current being delivered to electrode E1 and 100% of the stimulation cathodic current being delivered to electrode E2. During execution of the aggregate instruction at memory location Y+1, pulse program A is repeated five times with the stimulation anodic current being shared between electrodes E1 and E2 at 40% and 60%, respectively, and 100% of the stimulation cathodic current being delivered to electrode E3. As indicated, the aggregate logic block 516 repeatedly loops through the instructions between the aggregate start address (Y) and the aggregate end address (Y+1) as long as PDC 171(1) is enabled.

A beneficial aspect of the improved stimulation circuitry 170 is that each of multiple PDCs 171 can access the instructions in the aggregate memory 506, the pulse memory 504, and the steering memory 502. In the standard current mode, each of the different PDCs 171 can access the same library of aggregate instructions and generate different stimulation patterns simultaneously. In the example in FIG. 14, at the same time PDC 171(1) executes the aggregate instructions between addresses Y and Y+1, PDC 171(2) executes the aggregate instructions between addresses Y+2 and Y+5. During execution of the aggregate instruction at memory location Y+2, pulse program B is repeated 13 times with 100% of the stimulation anodic current being delivered to electrode E4 and 100% of the stimulation cathodic current being delivered to electrode E5. During execution of the aggregate instruction at memory location Y+3, pulse program A is repeated five times with 100% of the stimulation anodic current being delivered to electrode E4 and 100% of the stimulation cathodic current being delivered to electrode E5. During execution of aggregate instruction at memory location Y+4, pulse program C is repeated five times with 100% of the stimulation anodic current being delivered to electrode E4 and the stimulation cathodic current being shared between electrodes E5 and E6 at 80% and 20%, respectively. During execution of the aggregate instruction at memory location Y+5, pulse program B is repeated seven times with 100% of the stimulation anodic current being delivered to electrode E4 and the stimulation cathodic current being shared between electrodes E5 and E6 at 80% and 20%, respectively. While a single sequence of the execution of the aggregate instructions between memory locations Y+2 and Y+5 is shown in FIG. 14, PDC 171(2) would repeatedly execute this sequence as long as PDC 171(2) is enabled in the same manner as described above with respect to PDC 171(1).

While stimulation can be provided simultaneously by the PDCs 171, the allocation of current during an active phase to the same electrode by different PDCs 171 may be prevented (unless arbitration is enabled for the PDCs 171 as described below). This may be accomplished in different ways such as preventing the assignment of a steering program having an overlapping electrode to two different PDCs or by allowing the assignment of steering programs with overlapping electrodes to two different PDCs 171 if it can be determined that no current will be allocated to the overlapping electrodes simultaneously during an active phase (i.e., the frequency, etc. prevent any actual conflict). These preventions may be implemented in external software such as software in a clinician's programmer that causes the microcontroller 150 to write the instructions and configuration parameters to the memory circuitry. For example, if a user attempts to define a program that would result in the allocation of current to the same electrode during an active phase by two different PDCs 171, the external software may prevent communication of the program to the IPG or require the enablement of arbitration for the two PDCs 171.

A notable exception to the prevention of the allocation of current by two different PDCs 171 to a single electrode simultaneously is that the case electrode is allowed to receive such overlapping currents. The sharing of current delivered by multiple PDCs is described in U.S. Patent Publication 2016/0184591, which is incorporated herein by reference. The ability to allow the case electrode to receive current based on the operation of different PDCs 171 simultaneously requires a few configuration changes. First, a "shared case" bit in the configuration memory 508 causes status flags that are generated when two PDCs 171 allocate current to the same electrode simultaneously to be blocked for the case electrode to prevent the unnecessary status flags. Additionally, one of the PDAC/NDAC 172p/172n pairs is selected for supply of the reference voltage Vref to the case electrode's operational amplifier 180.

Figure 15:
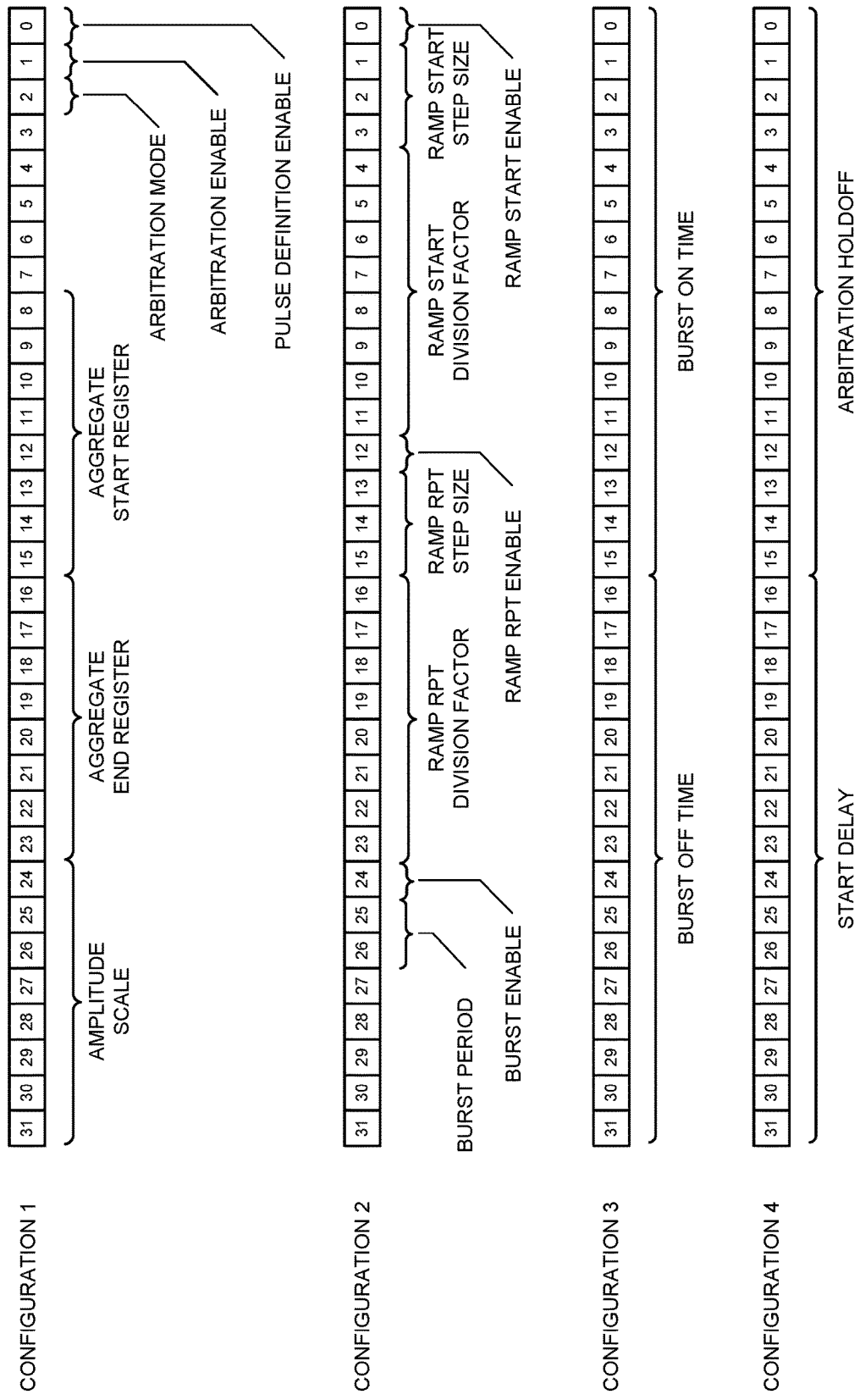
FIG. 15 illustrates an example arrangement of configuration parameters that are specific to a pulse definition circuit in accordance with an embodiment of the disclosure.

FIG. 13 described some of the basic parameters of the configuration memory 508 that are utilized by a PDC 171 during the execution of an aggregate program. An example arrangement of these parameters as well as other configuration parameters is illustrated in FIG. 15. These configuration parameters include adjustment parameters that adjust the timing or amplitude parameters defined by a pulse program. The enable, aggregate start address, and aggregate end address values discussed in reference to FIG. 13 are stored in a first configuration memory location as bit 0, bits 8-15, and bits 16-23, respectively. The first configuration memory location additionally stores an arbitration enable bit (bit 1) and an arbitration mode bit (bit 2). These arbitration parameters, when implemented, modify the timing of stimulation delivery between the various PDCs 171 as described in greater detail below. The first configuration memory location additionally stores an amplitude scale value in bits 24-31. The amplitude scale value is a multiplier between 0 and 1 (with 255 units of resolution) that modifies the amplitude of stimulation as compared to the value defined in a pulse instruction. This functionality is described below.

The second configuration memory location includes the parameters of a ramp start feature and a ramp repeat feature. These features, when implemented, cause the amplitude of the current generated by the DAC circuitry 172 to be increased to a desired maximum over a specified number of steps. The ramp start feature is applied to a sequence of pulses immediately following the enablement of the PDC 171. The ramp repeat feature is implemented for each execution of a new aggregate instruction following the last pulse in the ramp start group of pulses. In all other aspects, these ramp features operate in the same manner and have the same parameters, which include an enable bit (bits 0 and 12), a step size (bits 1-3 and 13-15), and a division factor (bits 4-11 and 16-23). The enable bit specifies whether the feature is implemented. The step size parameter is set to one of eight values that represent the number of steps over which the ramp scale value is increased. For example, the step size parameter may specify two, four, eight, 16, or 32 steps to full amplitude. The division factor parameter specifies the number of pulses at each step. The ramp features are described in detail below.

The second configuration memory location additionally includes a burst enable bit (bit 24) and a burst period value (bits 25 through 26). The burst enable bit determines whether a burst feature is implemented. The burst feature, when implemented, toggles the PDC 171's enable bit on and off at specified intervals. The burst period value specifies one of four period values (e.g., 6.25 ms, 50 ms, 100 ms, and 200 ms). The burst on and off values in the third configuration memory location specify the number of the burst periods during which the PDC 171's enable bit will be on (bits 0-15) and off (bits 16-31). The sixteen bits in each of the on and off values enable the specification of between 0 and 65535 burst periods.

The fourth configuration memory location includes an arbitration holdoff value (bits 0-15) that specifies the number of clock cycles associated with a PDC 171's arbitration feature, which is described below. The fourth configuration memory location additionally includes a start delay value (bits 16-31), which specifies the number of clock cycles after the PDC 171's enable bit is set that the execution of the specified aggregate instruction is initiated. The start delay value may be useful, for example, for staggering stimulation between PDCs 171 when the PDCs 171 are enabled at the same time. Note that the values in each of the four configuration memory location described with reference to FIG. 15 are specific to a particular PDC 171. Therefore, these parameters exist for each of the PDCs 171 at different memory location and can contain different values that are relevant only to the PDC 171 to which the parameters apply.

Figure 16:
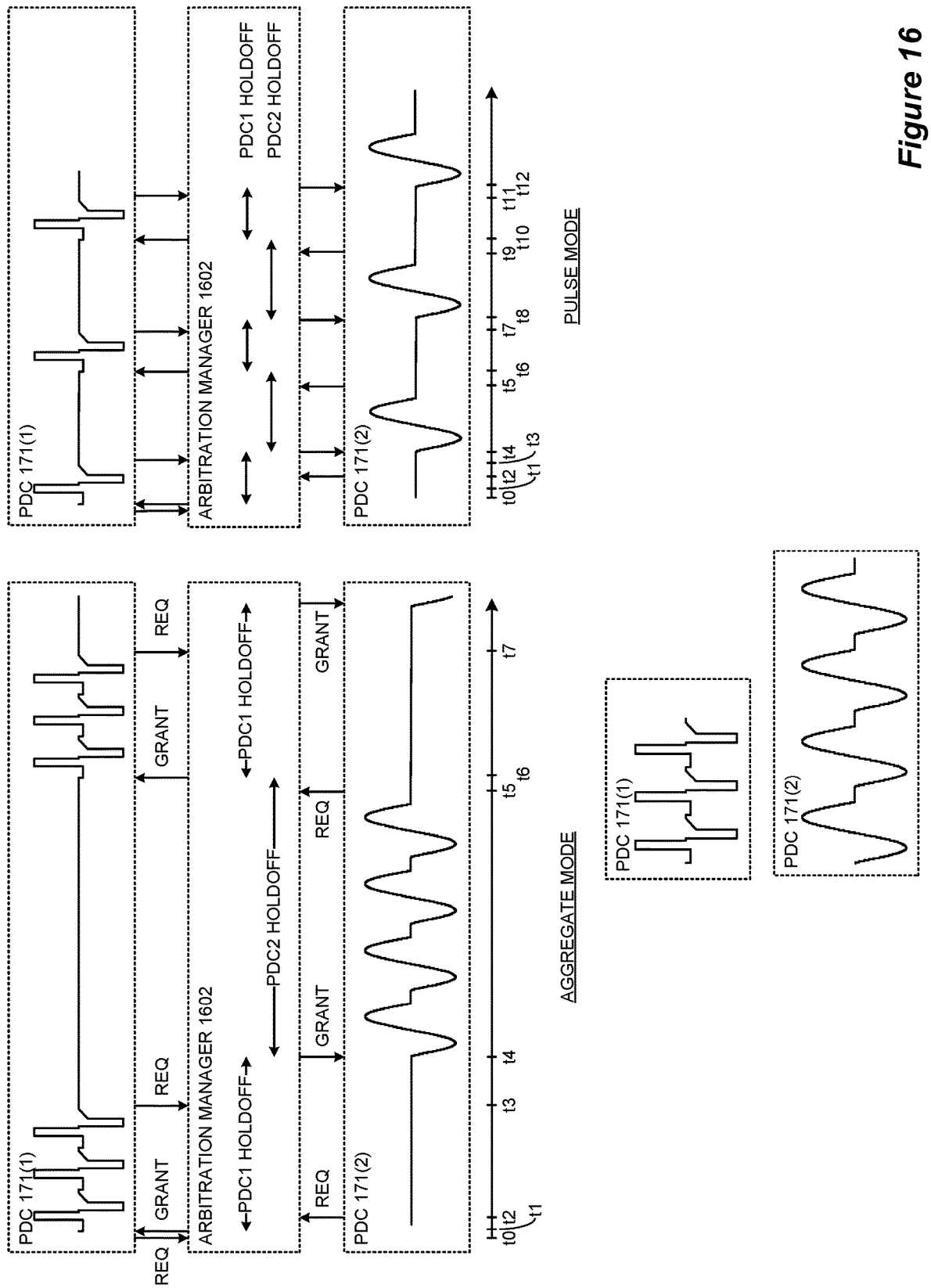
FIG. 16 illustrates the operation of an arbitration manager block in the stimulation circuitry to prevent the allocation of current by two or more different pulse definition circuits to a single electrode simultaneously in accordance with an embodiment of the disclosure.

FIG. 16 illustrates an example of the manner in which the arbitration feature modifies the timing of stimulation delivery for two PDCs 171 that have enabled arbitration. In the example shown, PDC 171(1) is configured to execute a single aggregate instruction that specifies three repetitions of pulse program A and PDC 171(2) is configured to execute a single aggregate instruction that specifies four repetitions of pulse program B. While these simple pulse patterns are selected for purposes of illustration, the arbitration feature is not so limited and can be enabled where a PDC 171 is configured to execute an aggregate program having multiple aggregate instructions and for more than two PDCs 171.

The arbitration feature can be utilized to prevent stimulation generated by a first PDC 171 from overlapping with stimulation generated by a second PDC 171 when the arbitration feature is enabled for both the first and second PDCs 171. Note that enablement of the arbitration feature does not prevent all other stimulation during the delivery of arbitrated stimulation but only the execution of other stimulation that is also arbitrated. The arbitration feature may be valuable for enabling the delivery of stimulation waveforms from two or more different PDCs 171 to overlapping sets of electrodes. By enabling arbitration for each of the PDCs 171 that are configured to deliver stimulation to one or more common electrodes, it can be ensured that there is no simultaneous delivery of stimulation to a single electrode from different PDCs 171.

When a PDC 171's arbitration feature is enabled, the PDC 171 requests approval from an arbitration manager block 1602 before it proceeds. The arbitration manager block 1602 is part of the stimulation circuitry 170 and is common to all of the PDCs 171. The timing of the stimulation request from the PDC 171 is dependent upon the selected arbitration mode. In the aggregate arbitration mode, the PDC 171 requests approval prior to executing an aggregate instruction. Upon the grant of approval, the PDC 171 executes the full aggregate instruction. This is illustrated in the aggregate mode portion of FIG. 16.

At time t0, PDC 171(1) communicates a request to the arbitration manager block 1602. Because there is no active holdoff timer, the arbitration manager block 1602 communicates the grant to PDC 171(1) at t1 and starts accumulating the holdoff timer. Upon receiving the grant at t1, PDC 171(1) executes an aggregate instruction. At t2, PDC 171(2) requests approval from the arbitration manager block 1602. However, because the holdoff timer associated with the grant to PDC 171(1) is active, the request from PDC 171(2) is queued. At t3, PDC 171(1) completes the execution of the aggregate instruction and communicates a request to execute the subsequent aggregate instruction (in this case the same aggregate instruction as the aggregate program is only one instruction in length) to the arbitration manager block 1602. Because the holdoff timer associated with PDC 171(1) is still active and the request from PDC 171(2) is already in the queue, PDC 171(1)'s request is queued behind the request from PDC 171(2). At t4, when the accumulated holdoff time is equal to the value specified in the PDC 171(1) configuration settings, the arbitration manager block 1602 communicates a grant to PDC 171(2) and begins accumulating the holdoff timer associated with the grant to PDC 171(2). Upon receiving the grant at t4, PDC 171(2) executes its aggregate instruction. This process repeats with each PDC 171 executing a full aggregate instruction at a time.

The pulse arbitration mode functions similarly to the aggregate arbitration mode except that each PDC 171 requests approval from the arbitration manager block 1602 prior to the execution of a single pulse. This is illustrated in the pulse mode portion of FIG. 16. Like the aggregate arbitration mode example, at t0, PDC 171(1) communicates a request to the arbitration manager block 1602, and, because there is no active holdoff timer, the arbitration manager block 1602 communicates the grant to PDC 171(1) at t1 and starts accumulating the holdoff timer. However, upon receiving the grant at t1, PDC 171(1) executes a single pulse rather than a full aggregate instruction. At t2, PDC 171(2) requests approval from the arbitration manager block 1602. However, because the holdoff timer associated with the grant to PDC 171(1) is active, the request from PDC 171(2) is queued. At t3, PDC 171(1) completes the execution of the pulse and communicates a request to execute the subsequent pulse to the arbitration manager block 1602. Because the holdoff timer associated with PDC 171(1) is still active and the request from PDC 171(2) is already in the queue, PDC 171(1)'s request is queued behind the request from PDC 171(2). At t4, when the accumulated holdoff time is equal to the value specified in the PDC 171(1) configuration settings, the arbitration manager block 1602 communicates a grant to PDC 171(2) and begins accumulating the holdoff timer associated with the grant to PDC 2. Upon receiving the grant at t4, PDC 171(2) executes a single pulse. This process repeats with each PDC executing a single pulse at a time. While the examples shown illustrate two PDCs 171 that each operate in the same arbitration mode, this is not necessary and arbitration can also be implemented with different PDCs operating in different arbitration modes.

In a preferred embodiment, arbitration processing is handled on the PDC side by the aggregate logic block 516. In such an embodiment, the aggregate logic block 516 communicates the arbitration request to the arbitration manager block 1602 when its repeat accumulator equals its repeat setting for aggregate mode arbitration and upon receipt of a pulse complete communication from the pulse logic block for pulse mode arbitration. In either case, the aggregate logic block 516 delays communication of the pulse and steering addresses to the pulse logic block 514 and steering logic block 512 until it receives the arbitration grant from the arbitration manager block 1602. It will be noted that a PDC 171's holdoff time setting should meet or exceed the time period of the longest pulse that it is configured to execute for pulse mode arbitration and the time period of the sequence of pulses associated with the longest aggregate instruction that it is configured to execute for aggregate mode arbitration in order to ensure that there is no overlap with any other arbitrated PDC 171. The arbitration manager block 1602 may be configured to resolve simultaneous arbitration requests. For example, the arbitration manager block 1602 may always give preference to the lowest numbered PDC 171.

Figure 17:
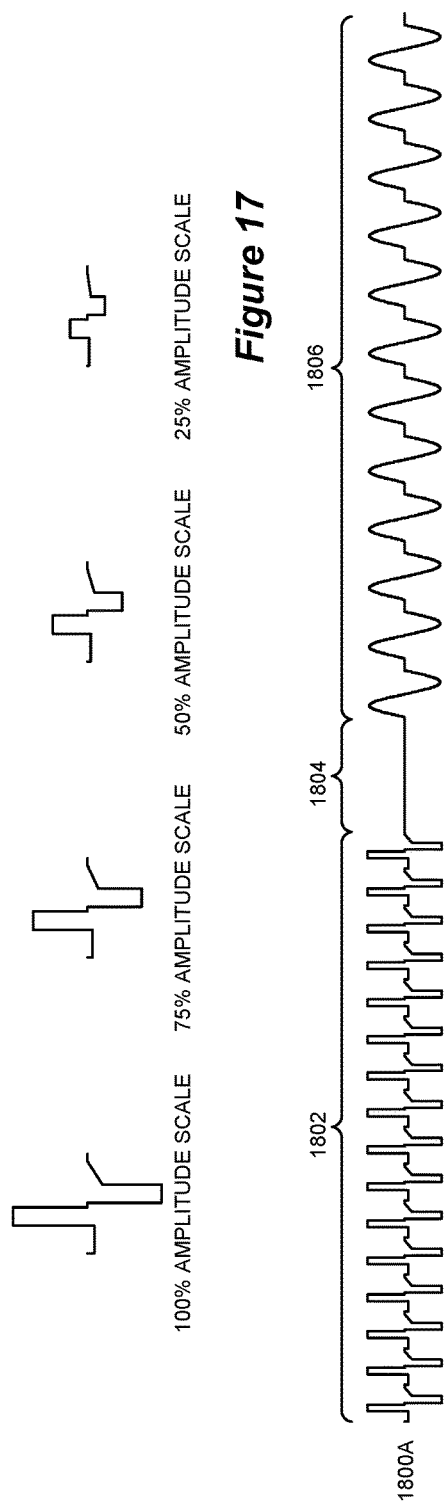
FIG. 17 illustrates the operation of an amplitude scale parameter in adjusting the amplitude of a pulse as defined by a pulse program in accordance with an embodiment of the disclosure.

FIG. 17 illustrates the operation of a PDC 171's amplitude scale value. As illustrated, the amplitude scale value is applied to each pulse phase of a pulse program. Thus, if the microcode for a particular pulse phase specifies an amplitude of 10 mA and the PDC 171 has a 50% amplitude scale value, the control signal output from the PDC 171 to the DAC circuitry 172 will represent a current value of 5 mA. The amplitude scale value enables a pulse program stored in the pulse memory 504 to be tailored to a particular need as opposed to creating a new pulse program. For example, assume that pulse program B is configured with a stimulation amplitude of 10 mA. Pulse program B can be utilized by PDC 171(1) at its full value (100% amplitude scale value) to deliver a sine wave pattern of stimulation that fluctuates between −10 mA and 10 mA and can also be utilized by PDC 171(2) at 25% of its full value (25% amplitude scale value) to deliver a sine wave pattern of stimulation that fluctuates between −2.5 mA and 2.5 mA. Without the amplitude scale value, a new pulse program would need to be created in order to enable the stimulation pattern provided by stimulation circuit 171(2), which additional pulse program would require 58 additional pulse instructions in the pulse memory 504.

Figure 18:
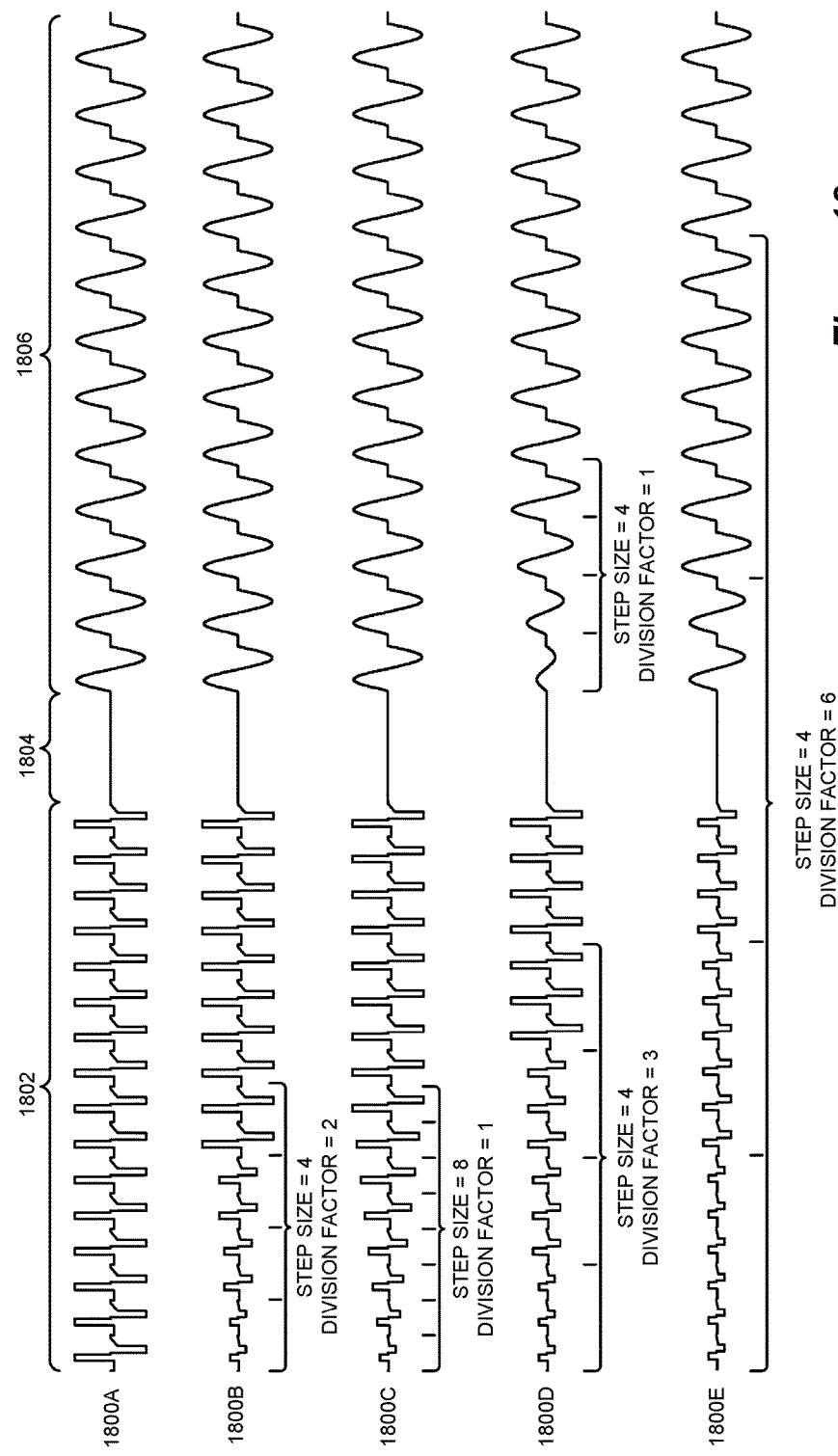
FIG. 18 illustrates the effects of a ramp start feature and a ramp repeat feature with differing parameters on a stimulation waveform generated by the stimulation circuitry in accordance with an embodiment of the disclosure.

FIG. 18 illustrates the effects of the ramp start and ramp repeat features. Each stimulation pattern 1800 includes a first portion 1802 that represents execution of an aggregate instruction that specifies 16 repetitions of pulse program A, a second portion 1804 that represents execution of an aggregate instruction that specifies a delay period, and a third portion 1806 that represents execution of an aggregate instruction that specifies 12 repetitions of pulse program B. Portion 1802 is executed immediately after the PDC 171 is enabled.

The ramp start and ramp repeat features each act to slowly increase the amplitude of pulses in a sequence of pulses defined by an aggregate program to the full normal value (as specified by the pulse instruction and any applied amplitude scale value). Both the ramp start and ramp repeat features include a step size parameter and a division factor parameter. The step size parameter specifies the number of steps over which the pulses in a series are increased to the full normal value. For example, for a step size of eight, the amplitude of the pulse or pulses in the first step would be scaled to 12.5%, the amplitude of the pulse or pulses in the second step would be scaled to 25%, and so on. The division factor value specifies the number of pulses in each step. Together, the step size parameter and the division factor parameter specify the number of pulses (the product of the step size parameter and the division factor parameter) in a group of pulses in a pulse sequence to which the scale factor is to be applied and the number of sub-groups (or step groups) within the group. For example, a step size parameter of two and a division factor parameter of five defines a group of 10 pulses to which the ramp scale factor is to be applied and two sub-groups within the group. Note that the ramp scale factor applied to the last sub-group is equal to one and therefore the amplitude of the pulses in that sub-group are not modified from the amplitude defined by the pulse program and any amplitude scale factor. Nonetheless, the pulses in the last sub-group are still considered to be in the group.

The ramp scale factor (which is a separate scale factor applied in addition to any amplitude scale) can be calculated as the step number divided by the step size parameter for any pulse within the group to which the ramp scale factor applies. The step number can be calculated based on a pulse's sequential position within the group (i.e., the first pulse in the group is pulse one, the second pulse in the group is pulse two, etc.) divided by the division factor with non-integer values rounded up to the next integer. For example, the seventh pulse in a group having a step size parameter of four and a division factor parameter of four would have a step number of two (i.e., 7/4=1.75 rounded up to 2), which would result in a ramp scale factor of 50% (i.e., step number/step size=2/4=50%). Similarly, the seventh pulse in a group having a step size parameter of four and a division factor parameter of three would have a step number of three (i.e., 7/3=2.33 rounded up to 3), which would result in a ramp scale factor of 75% (i.e., step number/step size=3/4=75%). While the ramp features are described and illustrated as being used to increase the amplitude at various steps over a group of pulses, the ramp features could also be utilized to decrease the amplitude at various steps over a group of pulses (e.g., from a full amplitude defined by a pulse program to zero). For example, while the ramp start feature may increase the amplitude at the beginning of a sequence of pulses, the ramp repeat feature may either increase the amplitude over a group of pulses corresponding to a new instruction or the ramp repeat may decrease the amplitude over a group of pulses (e.g., decrease sequentially at each sub-group).

In the stimulation pattern 1800A, neither the ramp start nor the ramp repeat feature is enabled. In the second stimulation pattern 1800B, the ramp start feature is enabled with a step size parameter of four and a division factor parameter of two, and the ramp repeat feature is disabled. In the third stimulation pattern 1800C, the ramp start feature is enabled with a step size parameter of eight and a division factor parameter of one, and the ramp repeat feature is disabled. In the fourth stimulation pattern 1800D, the ramp start feature is enabled with a step size parameter of four and a division factor of three, and the ramp repeat feature is enabled with a step size parameter of four and a division factor parameter of one. Although the ramp repeat feature is only illustrated as being applied to portion 1806, it would also be applied to any pulses defined by a new aggregate instruction following the last pulse in a group of pulses to which a ramp feature (either ramp start or ramp repeat). The fifth stimulation pattern 1800E shows that a ramp feature define a group of pulses that extends across aggregate instructions. In the fifth stimulation pattern 1800E, the ramp start feature is enabled with a step size parameter of four and a division factor parameter of six, and the ramp repeat feature is also enabled. Note that the group of pulses in the pulse sequence to which the ramp start scale factor applies extends into the portion 1806, which is defined by a different aggregate instruction than the portions 1802 and 1804. Specifically, the first sub-group in the ramp start group includes the first six pulses (all of which are in portion 1802 and which are applied with a ramp scale factor of 25%), the second sub-group in the ramp start group includes pulses 7-12 (all of which are in portion 1802 and which are applied with a ramp scale factor of 50%), the third sub-group of pulses in the ramp start group includes pulses 13-18 (four of which are in the portion 1802 and two of which are in the portion 1806 and which are all applied with a ramp scale factor of 75%), and the fourth sub-group of pulses in the ramp start group includes pulses 19-24 (all of which are in portion 1806 and which are applied with a ramp scale factor of 100%). Note that even though the ramp repeat feature is enabled, it is not applied to any of the pulses in the portion 1806 because the ramp repeat feature is applied only to a group of pulses defined by a new aggregate instruction following the last pulse in a particular ramp group. Thus, the ramp repeat feature would be applied in the example sequence 1800E to a first group of pulses defined by an aggregate instruction executed after the aggregate instruction corresponding to portion 1806 (which may be the aggregate instruction corresponding to the portion 1802 in a subsequent execution of the aggregate program, for example).

FIG. 19 illustrates the effects of the burst feature. When the burst feature is enabled, the PDC 171's enable bit is toggled on and off in accordance with the burst on and burst off time parameters. When the PDC 171's enable bit is toggled on, a burst timer in the PDC 171 begins counting. When the burst timer reaches the burst on setting, the enable bit is toggled off and the burst timer is reset and begins counting again. When the burst timer reaches the burst off setting, the enable bit is toggled back on. This pattern continues such that stimulation is delivered by the PDC 171 in bursts during the burst on periods.

Having described the microcode structure and configuration settings as well as their processing via the relevant logic blocks in the PDCs 171, we now discuss the generation of the control signals that are passed to the DAC circuitry 172. The primary function of the stimulation circuitry 170 is to deliver control signals to the DAC circuitry 172 at the appropriate times. As described above, the aggregate logic block 516, pulse logic block 514, and steering logic block 512 manage the sequencing of instructions such that the appropriate instruction is referenced at any given time. For example, the active pulse instruction is referenced by the address parameter of the pulse logic block 514 and the active steering program is referenced by the address parameter of the steering logic block 512. The control signals are a function of the instructions and can therefore be generated based on the parameters of the active instructions. Referring to FIG. 5A, the primary control signals generated by the PDCs 171 are the branch switch control signals <C> and the current amplitude control signals <J>. Each PDC 171 additionally asserts the passive recovery bit P during execution of a delay phase for which passive recovery is specified. The control signal K is issued globally by the stimulation circuitry 170 (i.e., it is not issued by any particular PDC 171), and its function is described below. Additional control signals issued by the stimulation circuitry include the signals to enable the operational amplifiers 168 and 180 as described above.

Figure 5B:
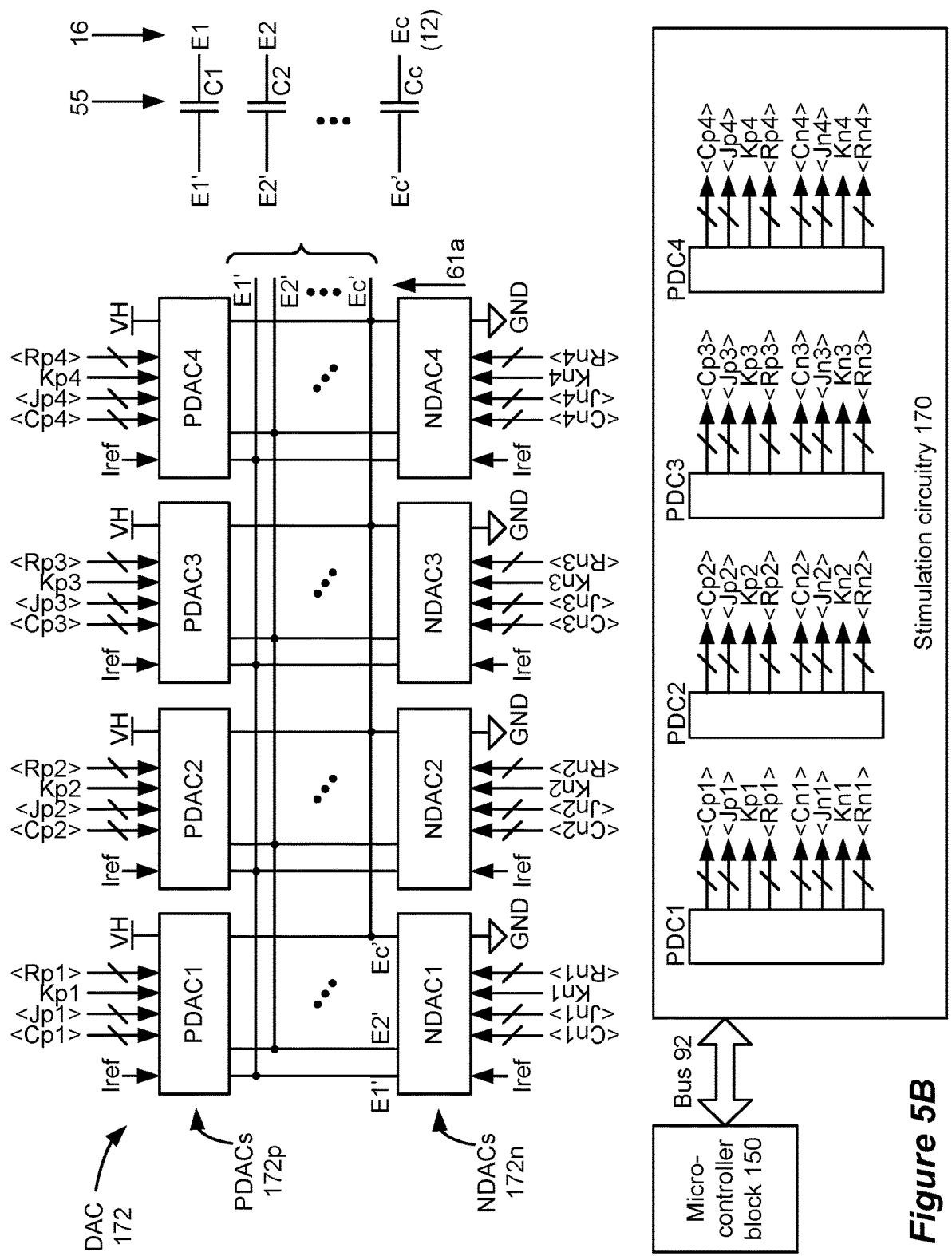
Figure 5C:
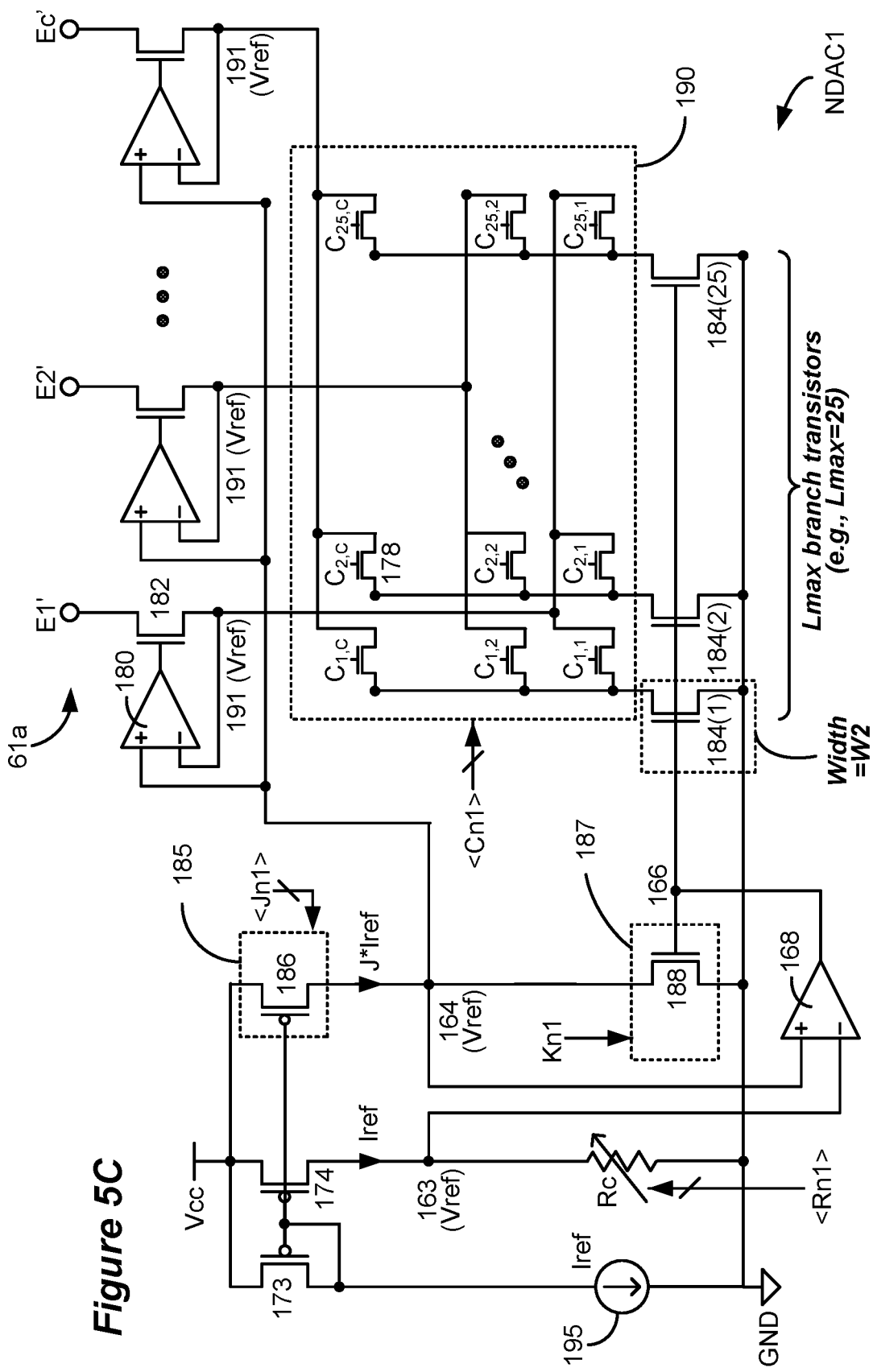

FIGS. 5B and 5C illustrate the structure of an example DAC circuit 172 that can be controlled by the stimulation circuit 170. The example DAC circuit 172 is described in detail in US Patent Application Publication 2018/0071520, which is incorporated herein by reference in its entirety. Because the DAC circuit 172 is described fully in that related application, its structure is only summarized here for the purpose of illustrating the utilization of the control signals issued by the stimulation circuitry 170. As shown in FIG. 5B, the DAC circuitry 172 includes four different stages, each stage including a PDAC 172p and an NDAC 172n. Each of these four stages is, in the standard current mode, linked to one of the PDCs 171 such that each PDC 171 controls a designated PDAC/NDAC pair 172p/172n. Note that control signal K described above is distributed to each of the PDACs 172p and NDACs 172n. In addition to the control signals illustrated in FIG. 5A, each of the PDACs 172p and NDACs 172n receives a control signal <R>, which signal is relevant to trimming a specific component of the DAC circuitry 172 and is not relevant to the function of the PDCs 171. The PDACs 172p and NDACs 172n may additionally receive passive recovery signals <Rec> (not shown), which are generated as a function of the signals <P> and a specified passive recovery mode. Generation of the passive recovery signals <Rec> is described in detail in US Patent Application Publication 2018/0071527, which is incorporated herein by reference in its entirety.

In the illustrated embodiment, the PDACs 172p1-4 are coupled to a compliance voltage VH, which is formed at the compliance voltage generator block 76 on the ASIC 160 (FIG. 4B). The NDACs 172n1-4 are coupled to ground (GND). Notice that corresponding electrode outputs of each of the PDACs 172p1-172p4 and corresponding electrode outputs of each of the NDACs 172n1-172n4 are connected together, and connected to its corresponding electrode node (E1'-Ec') 61a. This allows each of the PDACs to source a current to any of the electrode nodes (thus establishing an anode electrode) and each of the NDACs to sink a current from any of the electrode nodes (thus establishing a cathode electrode). More than one anode electrode and more than one cathode electrode can be established at a given time.

FIG. 5C shows the circuitry details for one of the NDACs 172n1 that is used to sink current from the electrode nodes, thus allowing electrodes coupled to those nodes to operate as cathodes. NDAC 172n1 receives control signals <Jn1> and <Cn1> from its associated PDC 171(1). NDACs 172n2-4 would be similar in construction, although they would receive different control signals from their PDCs 171(2)-(4). PDACs 172p1-4 would have a similar basic construction, although the circuitry would be "inverted." For example, current producing portions of the PDAC 172p1 are coupled to the compliance voltage VH instead of ground, thus allowing the PDAC 172p to source current to the electrode nodes 61a. Further, the polarity of many of the transistors is changed from N-channel devices to P-channel devices. Otherwise, and as one skilled in the art will understand, the PDAC functions similarly to the NDAC 172n1 of FIG. 5C.

Input to the NDAC 172n1 is a reference current Iref provided by a reference current source 195. Note in FIG. 5B that this reference current can be provided to each of the NDACs 172n1-4 and PDACs 172p1-4. The reference current Iref is mirrored by a well-known current mirror configuration into a transistor 174. The reference current Iref is further mirrored from transistor 173 into transistor(s) 186 in circuit 185 to produce an amplified current J*Iref at node 164. The value of the scalar J depends on the number of transistors 186 that are selectively included in the current mirror, which is adjustable in accordance with control signals <Jn1>. In this regard, because circuit 185 plays a significant role in setting the analog current in accordance with digital control signals <Jn1>, circuit 185 itself comprises a DAC within each of PDACs 172n and NDAC 172n and is referred to as a master DAC.

The amplified current J*Iref passes through a resistance block 187, formed in this example by M (e.g., four) paralleled transistors 188 (only one is shown). Included in series with each transistor 188 is a selection transistor, one of which is always on. A control signal Kn1 (which is generated from signal K) controls the other selection transistors. Kn1 is not asserted in the standard current mode, but is asserted in the high resolution current mode. When Kn1 is asserted in the high resolution mode, all transistors 188 are placed in parallel.

The gate of transistors 188 in the resistance block 187 are connected at node 166 to the gates of several branch transistors 184, each of which is connected to a column of switches 178 in switch matrix 190. Notice that transistors 188 and 184 are not coupled in a current mirror configuration (gate node 166 is not coupled to node 164 as would occur in a current mirror configuration; compare transistors 173 and 174). Rows of the switches 178 in the switch matrix 190 are connected to nodes 191 in each of the electrodes' output paths. In the example shown, there are 25 branch transistors 184, and 33 electrode nodes (E1' through E32' and Ec'), and thus switch matrix 190 comprises 25 times 33 switches and control signals <Cn1> to control each. Of course, differing numbers of branch transistors and electrode nodes could also be used.

Switch matrix 190 allows current to be provided to one or more selected electrodes with each branch transistor 184 providing a single "unit" of current. For example, assume it is desired to sink L (e.g., three) units of current from electrode E2. This can be accomplished by asserting any L of the control signals <Cn1> that service electrode node E2' (e.g., $C_{1,2}$, $C_{2,2}$, and $C_{3,2}$; again, any L control signals $C_{X,2}$ could be asserted). This would allow L branch transistors (e.g., 184(1), 184(2) and 184(3)) to each sink a unit of current from E2', and which in sum sinks three units of current from E2'. The 25 branch transistors enable the provision of 25 "units" of current, with each being directed to one selected electrode node 61a. Thus, the full amount of current provided by DAC 172n1 can be sunk from a single electrode by selecting all 25 of that electrode's control signals <Cn1> or from multiple electrodes by selecting other electrodes' control signals <Cn1>. In any event, each branch would sink 4% of the total current that is provided by the DAC 172n1. Current can be sourced to one or more electrode nodes 61a in a similar manner in a PDAC 172p.

The magnitude of the "unit" of current that is provided through each branch transistor 184 can be calculated as: Ibranch=Z*J*Iref, where Z is a ratio that is based on the properties of the transistors 188 and 184 and the number of transistors 188 that are asserted. The properties of the transistors 188 and 184 are fixed, and therefore the ratio Z only changes as a function of the number of transistors 188 that are asserted, which is determined based on the assertion of the control signal Kn1. In a preferred embodiment, Ibranch is four times greater in the standard current mode than in the high resolution current mode (i.e., $Z_{standard}=4*Z_{high}$), although other ratios could also be employed.

In high resolution current mode, each of the PDCs 171 executes the same aggregate instructions in unison. Thus, each of the PDCs 171 outputs the same current amplitude signals <J> (i.e., <Jp1>=<Jn1>=<Jp2>, etc.). Because Kn1 is asserted, the current, Ibranch, through each of the transistors 184 in each of the PDACs 172p and NDACs 172n is one-fourth of the value of Ibranch without Kn1 asserted. While each PDAC/NDAC pair 172p/172n can only deliver one-fourth of the current that it can provide in the standard current mode, the four pairs operating in unison can provide the same amount of current as can be provided from a single pair in the standard current mode. Moreover, this current is provided in "units" of Ibranch that are one-fourth the value of the standard current mode "unit," but with the ability to select up to four times the number of branch switches 178 (i.e., 100 source branch switches 178 across the four PDACs 172p and 100 sink branch switches 178 across the four NDACs 172n). This enables the delivery of current with a higher degree of resolution. For example, assume it is desired to split the anodic current between electrodes E1 and E2 with exactly 50% of the current delivered to each. This division cannot be accomplished in the standard current mode, because the PDAC 172p only enables allocation of current in 4% intervals. The closest allocation that could be accomplished in the standard current mode would deliver 48% of the current to one of the electrodes (12 branch switches 178 asserted) and 52% of the current to the other electrode (13 branch switches 178 asserted). In high resolution mode, however, the PDCs 171 could all process the same aggregate instructions in unison with 50 branch switches directing current to electrode E1 (e.g., all of the E1 switches in PDACs 172p1 and 172p2) and the remaining 50 branch switches directing current to E2 (e.g., all of the E2 switches in 172p3 and 172p4). Note that this requires the allocation of switches across multiple PDAC/NDAC pairs, where such pairs are dedicated to a single PDC 171 in the standard current mode. This allocation is accomplished by the electrode combiner 520 illustrated in FIG. 5A. The electrode combiner 520 is a logic block that determines which signals <C> to deliver to the DAC circuitry 172.

As described above, in the standard current mode, only the upper five bits in the current allocation portion of the steering program for each electrode are utilized. These five bits define the number of branch switches 178 (out of a maximum of 25) that are closed for each electrode. In the standard current mode, the electrode combiner 520 determines which of a PDC 171's corresponding PDAC 172p and NDAC 172n branch switches are to be closed. For example, the electrode combiner 520 may receive an E1 signal "010100" (80% anode) and an E2 signal "000100" (20% anode) from PDC 171(1), where the first bit indicates that each of E1 and E2 operate as anodes and the remaining five bits specify that 20 E1 branch switches 178 are to be closed and five E2 branch switches 178 are to be closed. In response, the electrode combiner 520 issues control signals <Cp1> to close the appropriate number of branch switches for each of E1 and E2 in the PDAC 172p1. The particular branch switches 178 that are to be closed can be determined in different ways. For example, the electrode combiner 520 may close the specified number of branch switches 178 for each electrode in electrode number and branch switch number order (e.g., close $C_{1,1}$ through $C_{20,1}$ and $C_{21,2}$ through $C_{25,2}$ in the above example).

In the high resolution current mode, all seven bits in the current allocation portion of the steering program for each electrode are utilized. These seven bits define the number of branch switches 178 (out of a maximum 100) that are closed for each electrode, which branch switches can span across different PDAC/NDAC pairs. In the high resolution current mode, the electrode combiner 520 allocates the branch switches 178 across multiple PDAC/NDAC pairs. For example, the electrode combiner 520 may receive an E1 signal "01010011" (83% anode) and an E2 signal "00010001" (17% anode) from PDC 171(1), where the first bit indicates that each of E1 and E2 operate as anodes and the remaining seven bits specify that 83 E1 branch switches 178 are to be closed and 17 E2 branch switches 178 are to be closed. Note that the electrode allocation signals may also be received from other PDCs 171 but will necessarily be redundant because the PDCs 171 operate in unison in high resolution current mode.

As the 83 and 17 branch switches 178 obviously span across multiple PDACs 172p (because each PDAC 172p includes just 25 switches 178), the electrode combiner 520 determines which switches are to be closed and sends the appropriate signals to the PDACs 172p. For example, the electrode combiner 520 may send the signals <Cp1>, <Cp2>, and <Cp3> instructing PDACs 172p1, 172p2, and 172p3 to close all 25 E1 branch switches 178 and signal <Cp4> instructing PDAC 172p4 to close 8 E1 branch switches 178 and 17 E2 branch switches. As in the standard current mode, the particular branch switches 178 that are to be closed can be determined in different ways. For example, the electrode combiner 520 may close the specified number of branch switches 178 for each electrode in electrode number, PDAC/NDAC number, and branch switch number order.

FIG. 20 summarizes the control signals <J> and <C> that are generated in different scenarios. In the standard current mode, the control signals <Cp> and <Cn> instruct the DAC circuitry 172 to open all branch switches 178 during any delay phase (i.e., when the pulse logic block 514 asserts the delay "D" signal). During a stimulation active phase instruction, the <Cp> signals are determined on the basis of the upper five bits of the steering program's allocation range for any electrode identified as a stimulation anode and the <Cn> signals are determined on the basis of the upper five bits of the steering program's allocation range for any electrode identified as a stimulation cathode. During an active recovery active phase instruction, the <Cp> signals are determined on the basis of the upper five bits of the steering program's allocation range for any electrode identified as a stimulation cathode and the <Cn> signals are determined on the basis of the upper five bits of the steering program's allocation range for any electrode identified as a stimulation anode. Note that the polarity reversal between the stimulation and active recovery scenarios is accomplished as a result of the assertion of the reverse polarity "RP" signal by the pulse logic block 514. The polarity reversal may be implemented in the steering logic block 512 such that the instructions provided to the electrode combiner 520 correctly identify the intended anode and cathode. Alternatively, the "RP" signal may be passed through to the electrode combiner 520 along with the original steering program microcode such that the electrode combiner 520 can itself implement the polarity reversal logic. For all phases other than a normal delay phase, the <Jp> and <Jn> control signals are determined by multiplying the amplitude value specified by the pulse instruction with the PDC 171's amplitude scale value and ramp scale value. The resulting value is the stimulation amplitude (i.e., the total amount of current that the PDAC 172$p$ sources and that the NDAC 172$n$ sinks). For example, if an active phase instruction specifies a 10 mA amplitude and the PDC 171 has an amplitude scale value of 50%, and the ramp scale value is calculated as 75%, the <Jp> and <Jn> signals are set to 10*0.5*0.75=3.75 mA, which causes the PDAC 172$p$ to source 3.75 mA and the NDAC 172$n$ to sink 3.75 mA through the selected electrodes. During a normal delay phase, the <Jp> and <Jn> signals are set to zero. In the high resolution current mode, the control signals differ only in that <Cp> and <Cn> are determined on the basis of all seven bits of the steering program's allocation range during any stimulation or recovery phase. As will be understood, the format of the control signals is dependent upon the structure of the DAC circuitry 172. While an example DAC circuit 172 was illustrated, the stimulation circuitry 170 is not limited to any particular DAC structure.

Figure 21:
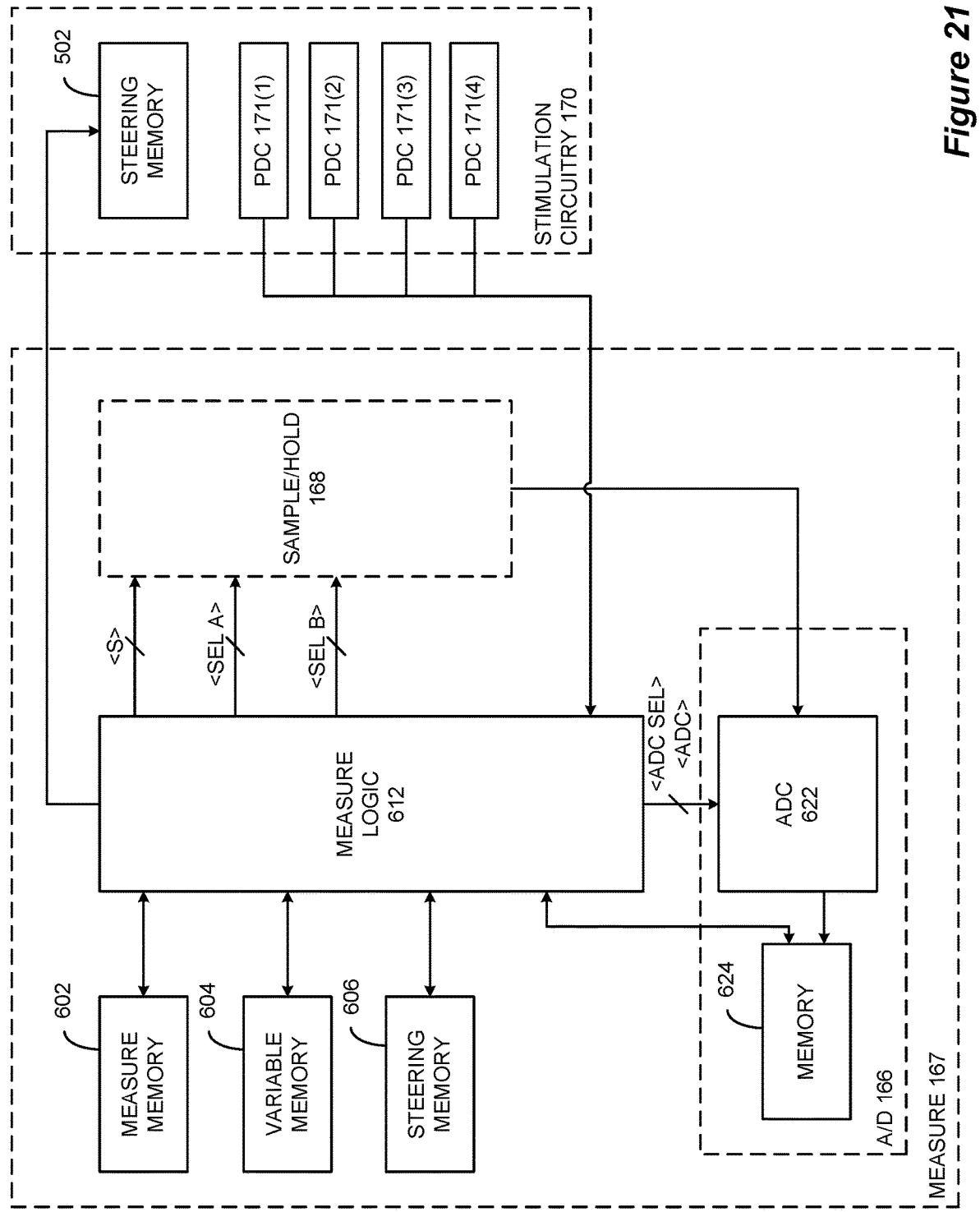
FIG. 21 illustrates the components of a measure circuitry block, which controls a sample and hold circuit block and an analog-to-digital (A/D) circuit block in accordance with an embodiment of the disclosure.

Having described the stimulation circuitry 170, we turn now to the measure circuitry 167 as depicted in FIG. 21, which controls the sample and hold circuitry 168 and the A/D circuitry 166 to measure analog signals and to store digitized values of the measured analog signals in the memory 624 (which may be a first in, first out (FIFO) memory), which values may be accessed, for example, by the microcontroller 150 to control various operations of the IPG. The memory 624 is part of the memory circuitry of the IPG. The sample and hold circuitry 168 selects from analog values on the analog bus 67 and is particularly useful in calculating the resistance between two electrodes as well as other voltages of interest during biphasic or monophasic pulsing. As will be understood, the desired measurements must be coordinated with the delivery of stimulation by the stimulation circuitry 170. Such coordination is complicated by the flexibility of the stimulation circuitry 170, which, as described above, enables non-arbitrated stimulation across multiple PDCs 171. In order to ensure that measurements are collected at the appropriate times, measure circuitry 167 includes a measure logic block 612 that processes measure microcode stored in measure memory 602 to generate control signals that are issued to the sample and hold circuitry 168 and the ADC 622. In its operation, the measure logic block 612 additionally retrieves and stores values in a variable memory 604 and a steering memory 606, which steering memory 606 is utilized to populate the steering memory 502 in the stimulation circuitry 170 as described below.

Figure 22:
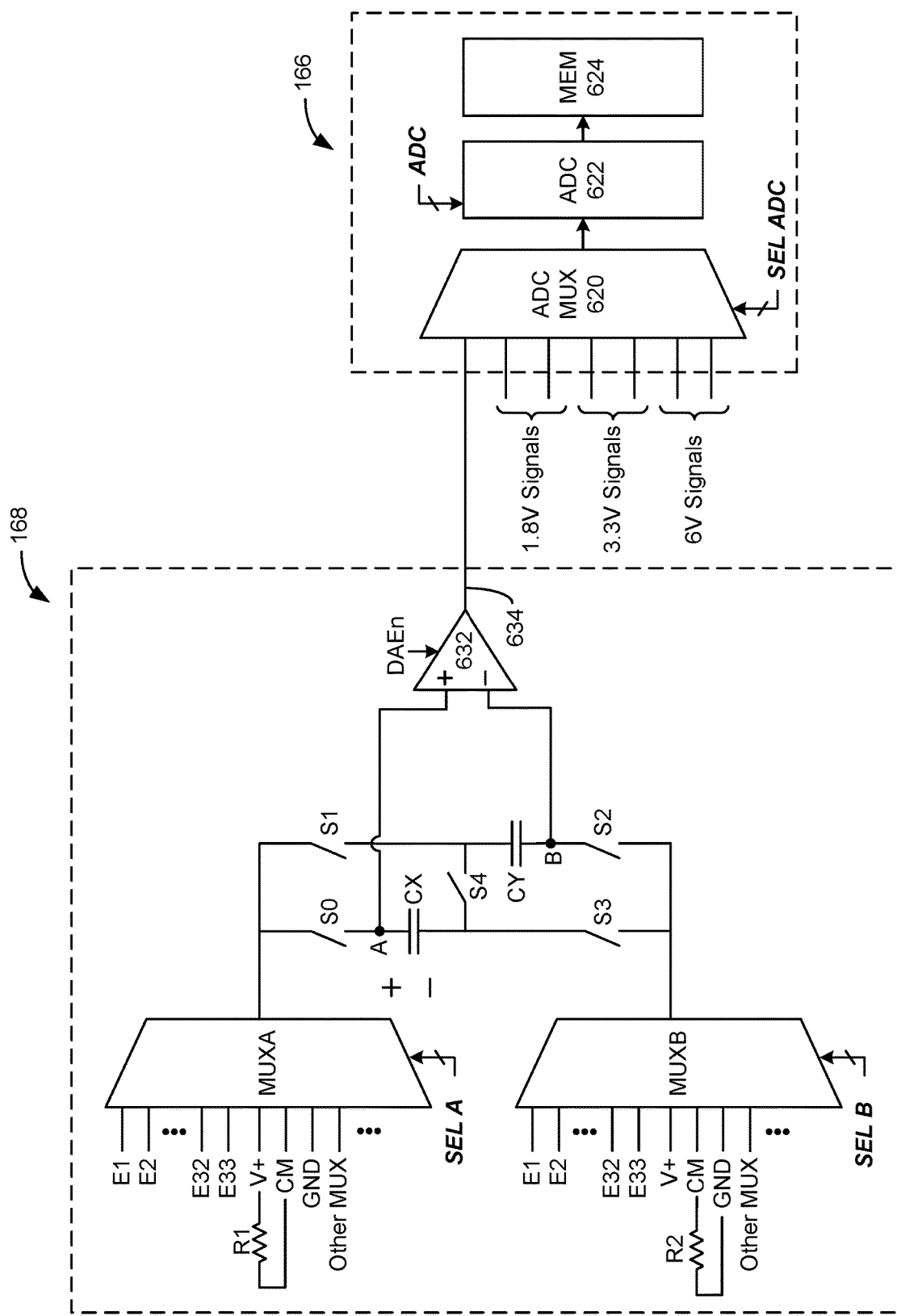
FIG. 22 illustrates components of the sample and hold circuitry and the A/D circuitry in accordance with an embodiment of the disclosure.

Before describing the structure of the measure instructions and the operation of the measure logic block 612 in processing such instructions, it is useful to describe the operation of the sample and hold circuitry 168 in providing an analog value to the ADC 622. FIG. 22 illustrates the components of the sample and hold circuitry 168 and A/D circuitry 166. In the disclosed embodiment, selection of analog signals from the analog bus 67 occurs using two multiplexers, MUXA and MUXB. The inputs to each MUX are essentially the same and comprise the electrode voltages (E1-E33); the compliance voltage used by the DAC circuitry 172 (VH); and ground (GND). As will be seen in the examples that follow, MUXA is generally used to select a higher voltage, such as an anode electrode or a supply voltage (e.g., VH), while MUXB is generally used to select a lower voltage, such as a cathode electrode or ground. An additional common mode input (CM) can be used during voltage monitoring, and the relevance of this input will be described later. Also, the output of each MUX is sent to the other MUX in case it is of interest to select such other output for a given measurement. Other analog signals of importance within the IPG may be included as inputs to the MUXes, and the inputs shown should not be understood as exhaustive. The input selected by MUXA and MUXB is dictated in accordance with control signals <SEL A> and <SEL B>, respectively. In one embodiment, the <SEL> signals may each comprise seven bits, which enables selection of up to 128 different inputs from a MUX.

Signals selected by the MUXes are held by circuitry that comprises two capacitors, CX and CY and a plurality of switches, S0-S4. Capacitors CX and CY are preferably identical, and may have a capacitance of 4.7 microfarads for example. As will be seen, monitored voltages are impressed or stored on these capacitors CX and CY, with a voltage selected by MUXA being presented to the top plates of CX and CY, and a voltage selected by MUXB being presented to the bottom plates of CX and CY. The switches S0 through S4 are controlled by the signals <S> from the measure logic block 612 as described below. Nodes A and B are input to a differential amplifier 632, which outputs their difference (i.e., VA−VB) as an analog signal 634. Additional details regarding the sample and hold circuitry 168 can be found in U.S. Pat. No. 9,061,140, which is incorporated herein by reference in its entirety.

The signal 634 is passed to the A/D circuitry 166, where it is input into ADC MUX 620. ADC MUX 620 selects between the signal 634 output from the sample and hold circuitry 168 and other analog signals at different voltage levels, such as Vbat, which additional signals are not impacted by operation of the stimulation circuitry 170 and which are therefore not discussed in detail. The input selected by the ADC MUX 620 is dictated in accordance with control signal <SEL ADC>, which may comprise four bits to enable selection of up to 16 different inputs. The output of the ADC MUX 620 is provided to the ADC 622, which digitizes the value at its input to store measurements in the memory 624 in accordance with the signal <ADC>, which specifies various parameters for a particular measurement.

Figure 23A:
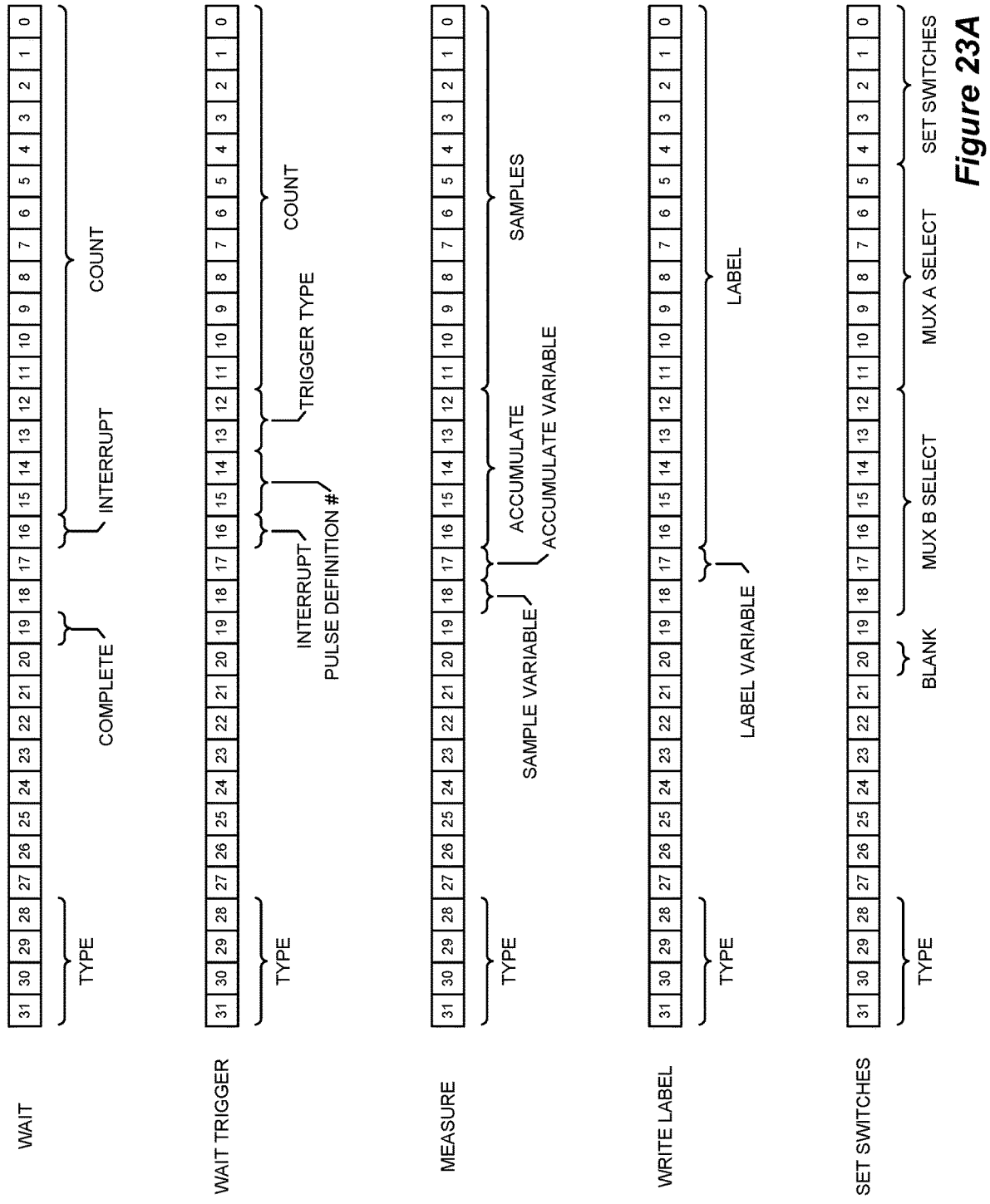
FIGS. 23A and 23B illustrate the arrangement of microcode to form instructions that cause a measure logic block in the measure circuitry to perform actions in accordance with an embodiment of the disclosure.
Figure 23B:
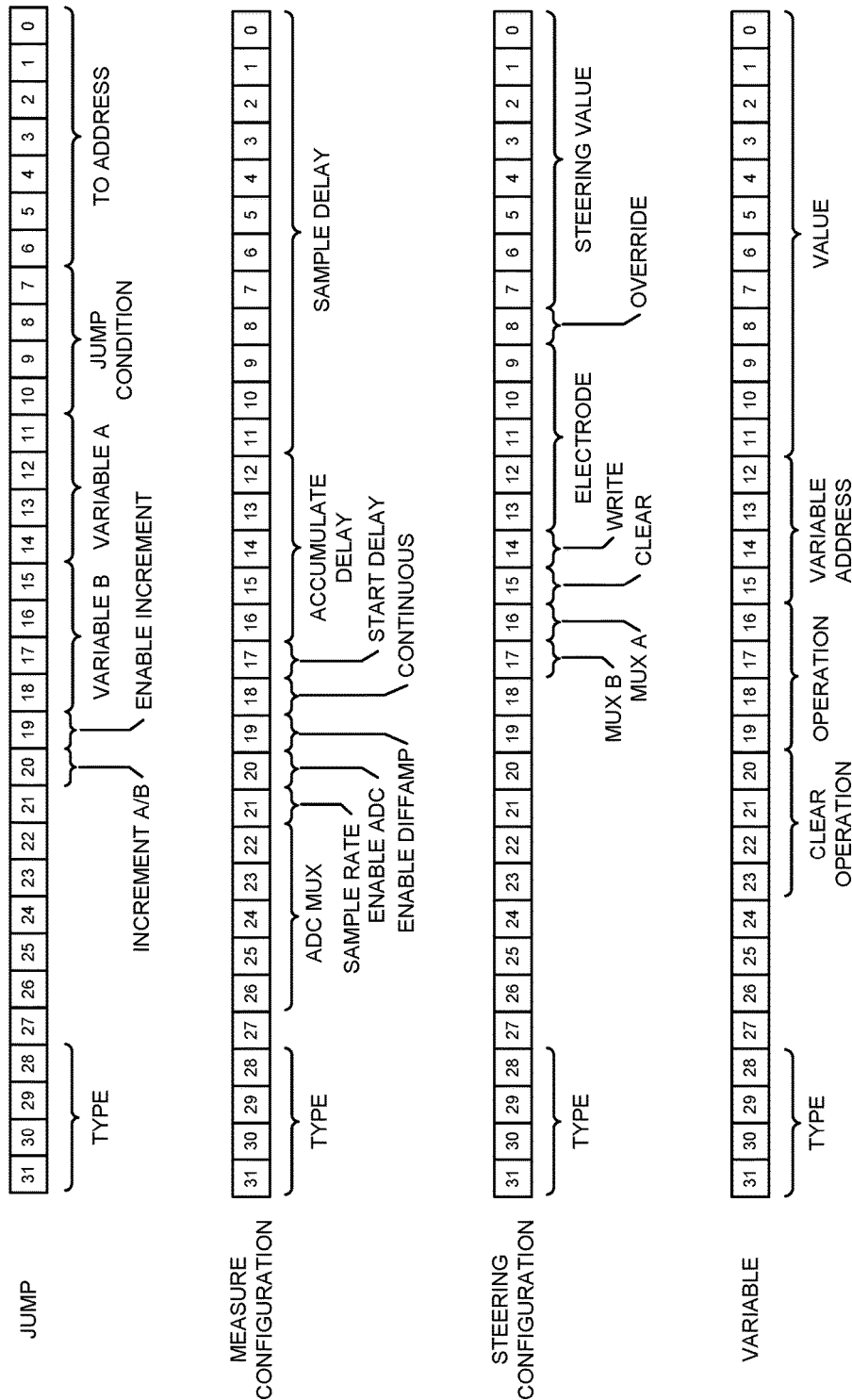

FIGS. 23A and 23B illustrate the structure of the measure microcode for different types of instructions that can be executed by the measure logic block 612. Each instruction is stored in a single memory location within the measure memory 602. The type of each measure instruction is represented by its upper four bits (bits 28-31). This four bit range enables the specification of up to 16 different types of instructions, and the bit range for the type identifier is common for each of the different types of instructions and is therefore not repeated in the description of each specific instruction. The wait instruction specifies a number of clock cycles for which the measure logic block 612 is to hold before proceeding to the next measure instruction in the memory 602. Bits 0-15 of the wait instruction specify the number of clock cycles, bit 16 of the wait instruction, when set, instructs the measure logic block 612 to issue an interrupt when the wait period is complete, and bit 19 of the wait instruction, when set, instructs the measure logic block 612 to halt execution.

Whereas the wait instruction causes the measure logic block 612 to wait for a specified time period before proceeding to the next instruction, the wait trigger instruction causes the measure logic block 612 to wait for a specified number of a specified trigger type from a specified PDC 171 before proceeding to the next measure instruction. Bits 0-11 specify the number of triggers that the measure logic block 612 should wait to receive before proceeding to the next measure instruction, bits 12-13 specify the type of trigger and bits 14-15 specify the PDC 171 that applies to the instruction. The four different types of triggers that can be specified by the two-bit trigger type range of the wait trigger instruction are generated by each PDC 171 upon the occurrence of different events during the execution of aggregate and pulse instructions, and the triggers can be communicated to the measure logic block 612 via the bus 92 or via an off-bus link between the stimulation circuitry 170 and the measure circuitry 167.

FIG. 24 illustrates the events that lead to the generation of each of the different types of triggers for the example execution of aggregate instructions by a particular PDC 171. In the example shown, the aggregate program includes a first aggregate instruction (Aggregate 1) that specifies a number of repetitions of pulse program B, a second aggregate instruction (Aggregate 2) that specifies a number of repetitions of pulse program C, and a third aggregate instruction (Aggregate 3) that specifies a number of repetitions of pulse program A. The assigned steering program is not relevant to the generation of the triggers. As illustrated, the aggregate program trigger (Trigger 00) is generated when the aggregate logic block 516 begins executing the aggregate instruction at the aggregate start address. In the illustrated example, this trigger is generated at the start of the execution of the first aggregate instruction (Aggregate 1). The aggregate trigger (Trigger 01) is generated when the aggregate logic block 516 begins executing a new aggregate instruction. In the illustrated example, this trigger is generated at the start of the execution of the first, second, and third aggregate instructions. The pulse trigger (Trigger 10) is generated when the pulse logic block 514 begins executing a pulse instruction at an address delivered to it by the aggregate logic block 516 (i.e., at the beginning of the execution of a pulse program). The phase trigger (Trigger 11) is generated when the pulse logic block 514 begins executing any pulse instruction (i.e. at the beginning of the execution of each phase of a pulse program). The wait trigger instruction enables an action to be performed at a particular point during stimulation. For example, if it is desired to take an action at the beginning of the $32^{nd}$ phase of the third pulse during the execution of the second aggregate instruction (i.e., the position denoted as 2400), a series of wait trigger instructions could be arranged to wait for one occurrence of the aggregate program trigger followed by one occurrence of the aggregate trigger followed by two occurrences of the pulse trigger followed by 31 occurrences of the phase trigger.

Returning to FIG. 23A, the measure instruction passes parameters to the ADC 622 (via signals <ADC>) to indicate a number of measurements to store in the memory 624. Bits 0-11 specify a number of samples to store in the memory 624. Bits 12-16 specify an accumulate value. The accumulate value specifies a number of measurements to add together to be stored as a single sample. This can be useful, for example, to compute an average value while only storing a single sample in the memory 624. While the sample and accumulate values can be entered directly in their respective ranges of the measure instruction, bits 17 and 18 enable the use of a variable to specify the accumulate and sample values, respectively. When the accumulate and/or sample variable bits are set, the lower four bits of the respective value field (i.e., bits 12-15 for accumulate and bits 0-3 for sample) provide an address, and the value at the specified address in the variable memory 604 is used as the sample or accumulate value for the measure instruction. The use of variables for the sample and accumulate values enables the same instruction to be repeated with different parameters by updating the values in the specified addresses of the variable memory 604. The use of the lower four bits of the sample and accumulate ranges of the measure instruction as the address assumes that the variable memory 604 contains 16 memory locations. The number of bits used to represent the address can be adjusted to accommodate a different size of variable memory 604.

The write label instruction causes the measure logic block 612 to write the 17-bit value in the label range of the instruction (i.e., bits 0-16) to the memory 624. This can be used for example, before or after a measure instruction to provide an indicator of what the data preceding or succeeding the label represents. When the label variable bit (i.e., bit 17) of the write label instruction is set, the lower four bits of the label range of the instruction are used as an address to retrieve a 12-bit value from the variable memory 604. The upper five bits of the label range of the instruction will be written with the 12-bit value retrieved from the memory 604 to the memory 624.

The set switches instruction is used to set the <S>, <SEL A>, and <SEL B> values that are passed to the sample and hold block 168. Bits 0-4 of the set switches instruction correspond directly to the state of the S0 through S4 switches. Bits 5-11 specify the <SEL A> value and bits 12-18 specify the <SEL B> value, which values determine which input of the respective MUX is selected. In one embodiment, a defined fixed value in these fields can be used to retrieve the value from a MUX address in the variable memory 604. For example, a decimal value of 126 in either the MUX A or MUX B select fields causes the measure logic block 612 to retrieve a value from a MUX A address (e.g., address 13) in the variable memory 604 and a decimal value of 127 causes the measure logic block 612 to retrieve a value from a MUX B address (e.g., address 14) in the variable memory 604. Bit 20 is a blanking bit that causes all of the switches in the sample and hold circuit 166 to open for a partial clock cycle before the MUX select and switch S0 through S4 signals go to the values specified in the instruction.

Referring to FIG. 23B, the jump instruction specifies an address in the measure memory 602 to which the measure logic block 612 should proceed (either unconditionally or if specified conditions are met). This differs from the processing of other instructions, after which the measure logic block 612 simply proceeds to the instruction in the next memory location. Bits 0-6 of the jump instruction specify the address in the measure memory 602 to which the measure logic block 612 is to proceed. Bits 7-9 specify one of a number of different jump conditions, which include an unconditional jump (jump to address immediately), a return jump (jump to address succeeding the address stored in the return field), jump to variable address (use lower four bits of address range of jump instruction as address to retrieve the jump to address value from the variable memory 604), different conditional jumps (jump to address if A>B, A<B, A≥B, A≤B, or A=B), and a branch jump (unconditional jump to a specified address that stores the address of the branch jump instruction in the return field such that a subsequent return jump returns to that point). Bits 11-14 and 15-18 specify the variable A address and the variable B address in the variable memory 604 for use with any of the conditional jump types. Bit 19 of the jump instruction enables the value in one of the variable ranges of the instruction to be incremented and bit 20 specifies whether the variable A value (bits 11-14) or the variable B value (bits 15-18) is to be incremented.

The measure configuration instruction sets the parameters of the ADC 622 according to which a measurement is to be taken. Bits 0-11 specify the number of clock cycles to delay before storing a sample in the memory 624 during execution of a measure instruction. Bits 12-16 specify the number of clock cycles to delay before accumulating a measured value. Bit 17 specifies whether the sample delay value should be implemented prior to the first sample being stored. If bit 17 is set, the sample delay will only be implemented between samples (i.e., not prior to the first sample), but, if it is not set, the sample delay will be implemented prior to storing each sample (even the first sample of a measure instruction). Bit 18, when set, implements continuous sampling mode, which causes the ADC 622 to continuously store measurements in the memory 624 until a measure instruction is halted. Bit 19 enables the differential amplifier 632 (signal DAEn) and bit enables the ADC 622. Bit 21 chooses between a normal clock (e.g., 100 kHz) and a fast clock (e.g., 8 MHz) to be used by the ADC 622. Bits 22-24 specify the <SEL ADC> value, which determines which input to the ADC MUX 620 is passed to the ADC 622.

Figure 25:
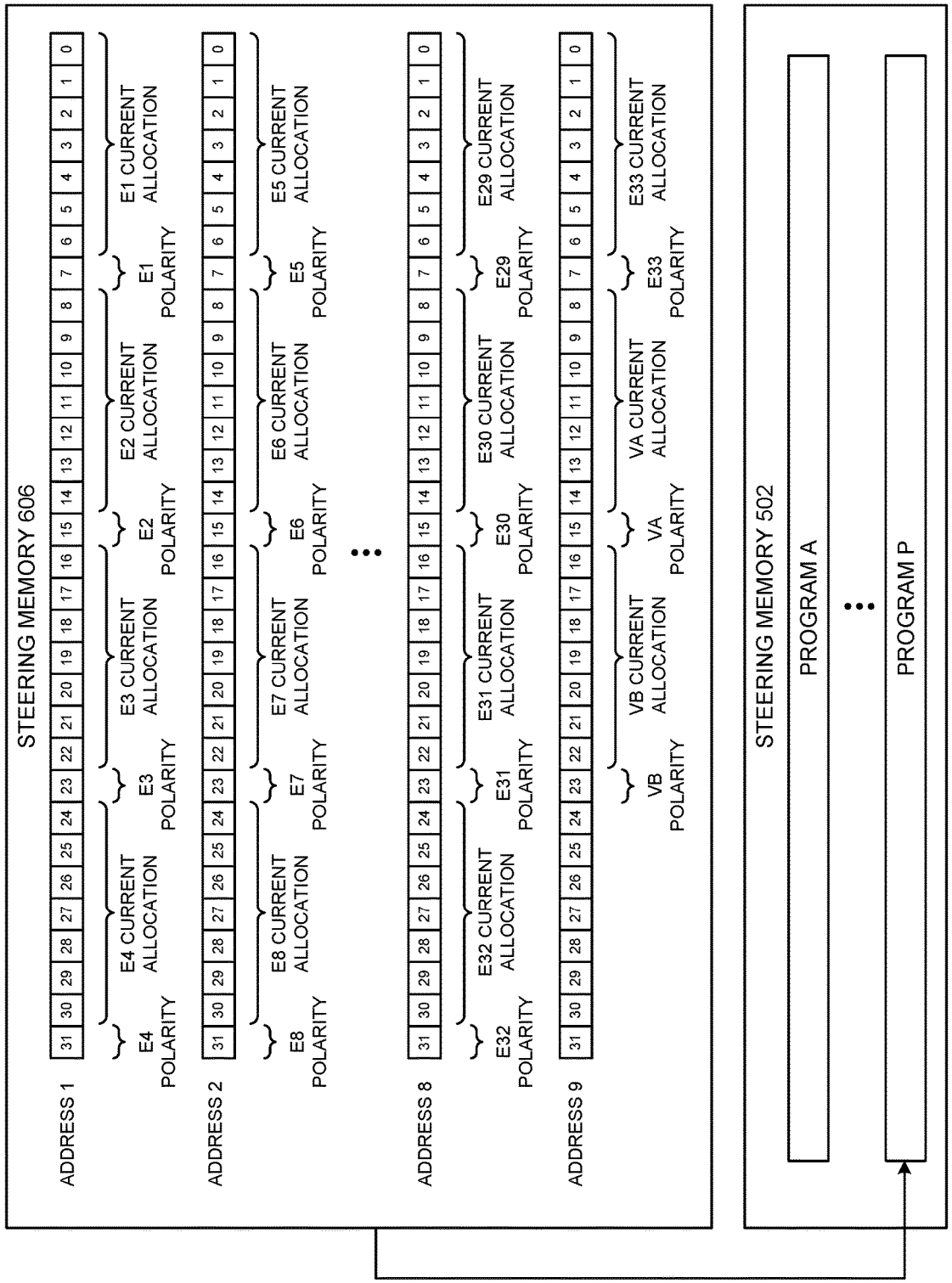
FIG. 25 illustrates a steering memory in the measure circuitry and its use in configuring a steering program in the stimulation circuitry in accordance with an embodiment of the disclosure.

The steering configuration instruction is used to populate the steering memory 606 and to define the way in which its values are populated into an associated steering program in the steering memory 502. Before describing the parameters of the steering configuration instruction, it is useful to understand the structure of the steering memory 606, which is illustrated in FIG. 25. The steering memory 606 includes nine memory locations, which are arranged in essentially the same manner as a single steering program in the steering memory 502. As shown, each 32-bit location in the steering memory 606 specifies the parameters of four electrodes, with each electrode defined by a single byte that specifies the electrode's stimulation polarity and allocation of current of the specified stimulation polarity. The parameters of the various electrodes are also arranged in the same manner in the steering memory 606 as in a steering program in the steering memory 502 (e.g., bits 0-7 of address 1 specify parameters of electrode E1, bits 8-15 of address 2 specify parameters of electrodes E2, etc.). The steering memory 606 differs from a steering program in steering memory 502 only in that it enables the assignment of parameters for two additional electrodes in address 9. These additional electrodes are a virtual electrode VA, which is associated with MUX A and has parameters that are defined by bits 8-15 of address 9, and a virtual electrode VB, which is associated with MUX B and has parameters that are defined by bits 16-23 of address 9. The specified parameters of these virtual electrodes can be written into the parameters of a "real" electrode in the steering memory 606 based upon the select signal of the associated MUX as described below.

Returning to FIG. 23B, bits 0-7 of the steering configuration instruction specify an individual electrode's steering value, which is arranged in the same manner as described above with respect to the steering memory 502 (i.e. the most significant bit defines the stimulation polarity and the remaining seven bits define the allocation of current of the specified polarity). Bit 8 of the steering configuration instruction, when set, prevents the specified steering value from being overwritten by the value from one of the virtual electrodes. Bits 9-13 specify the electrode number to which the steering value applies. Bit 14, when set, causes the measure logic block 612 to write the specified steering value to the location of the specified electrode in the steering memory 606. Bit 15, when set, clears all of the values in the steering memory 606. Bits 16 specifies whether the parameters in the steering memory 606 for virtual electrode VA are to be written to the location in the steering memory 606 that corresponds to the electrode specified by the value in the MUX A address in the variable memory 604, and bit 17 specifies the same properties with respect to virtual electrode VB and MUX B.

The variable instruction includes a value range (bits 0-11), a variable address range (bits 12-15), an operation range (bits 16-19), and a clear operation range (bits 20-23). The operation and clear operation bit ranges enable the specification of a particular type of operation such as write, copy, add, subtract, and various logical operations, which can be performed to manipulate the data in the variable memory 604 according to the specified variable address and value.

Figure 26A:
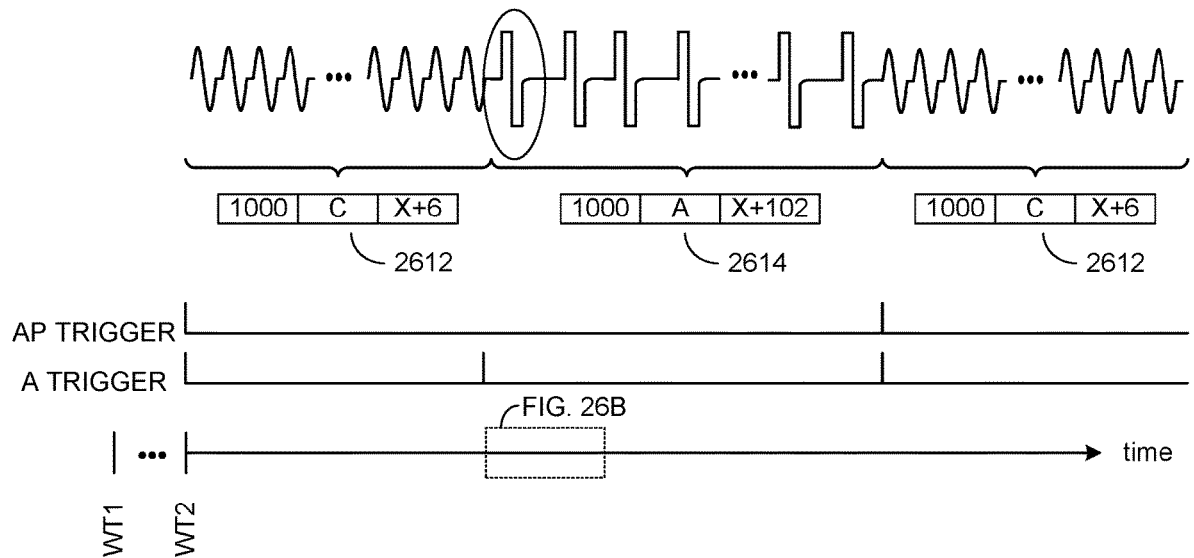
FIGS. 26A-26G illustrate an example set of measure instructions to measure a voltage between two electrode nodes in accordance with an embodiment of the disclosure.

FIGS. 26A-26G illustrate an example use of the measure instructions (any one or more measure instructions define a measure program) to measure the voltage between electrode nodes E1' and E2' during provision of a pulse, and more particularly to measure the resistance between those electrode nodes. Referring to FIG. 26A, PDC 171(1) generates a stimulation waveform that is formed through the execution of two aggregate instructions: a first aggregate instruction 2610 that specifies 1000 repetitions of pulse program B (which begins at pulse memory location X+6) according to the electrode configuration in steering program C and a second aggregate instruction 2612 that specifies 1000 repetitions of pulse program D (which begins at pulse memory location X+102) according to the electrode configuration in steering program A. Pulse program D, while not introduced to this point, is described below.

Determination of the resistance between electrodes E1 and E2 is accomplished by measuring the voltage between the corresponding nodes E1' and E2' while electrodes E1 and E2 are being used to deliver stimulation of a known current, I. In the example in FIG. 26A, the known stimulation current flows between E1 and E2 during stimulation and active recovery phases during the execution of the second aggregate instruction 2612. The example shown in FIG. 26A illustrates an example set of instructions 2616 in the measure memory 602 executed by the measure logic block 612 to control the sample and hold circuitry 166 and the A/D circuitry 168 to measure the voltage across E1' and E2' during the appropriate time periods (i.e., a portion of the stimulation phase and a portion of the active recovery phase) of the first execution of pulse program D during a specific execution of the aggregate instruction 2614 by PDC 171(1).

Figure 26B:
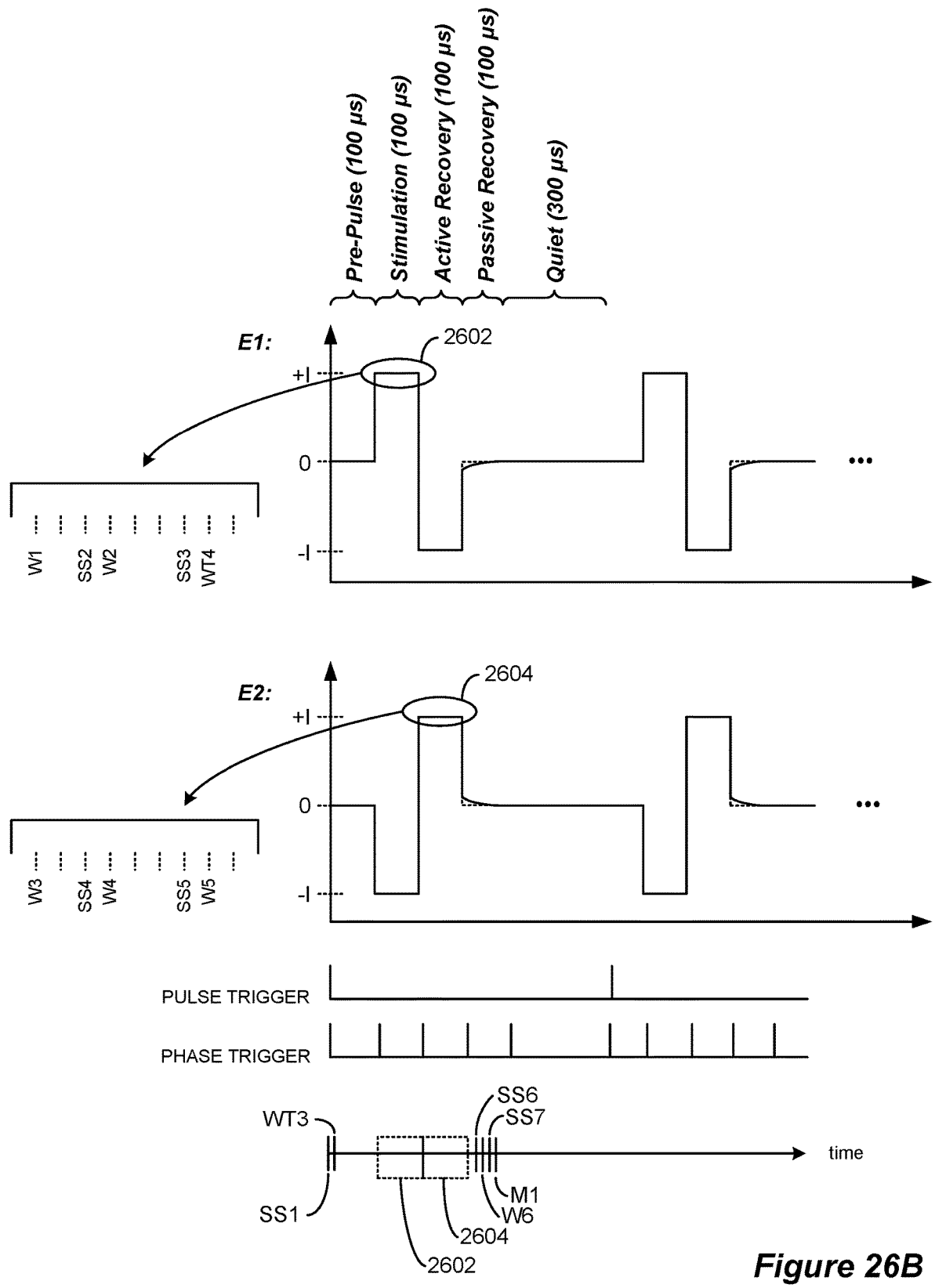

The first instruction (WT1) in the instruction set 2616 is a wait trigger instruction that causes the measure logic block 612 to wait for 2000 occurrences of the start of execution of an aggregate program (i.e., the start of execution of the aggregate instruction at the PDC's aggregate start address). During execution of the WT1 instruction, the measure logic block 612 maintains a count of the specified trigger received from PDC 171(1). When the count reaches the value specified in the WT1 instruction (2000), the measure logic block proceeds to the next instruction, which is stored in the next address in the measure memory 602. The next instruction (WT2) is also a wait trigger instruction. The WT2 instruction causes the measure logic block 612 to wait for a single occurrence of the aggregate trigger. As illustrated in the time line, the WT2 instruction is executed immediately following the receipt of the 2000$^{th}$ aggregate program trigger following execution of the WT1 instruction. An aggregate trigger is also received at the same time as the 2000$^{th}$ aggregate program trigger, but the WT2 instruction is executed on the next clock cycle. Thus, the next aggregate trigger represents the start of the execution of the aggregate instruction 2614 during which the E1'-E2' voltage measurement is to be taken. FIG. 26B illustrates the stimulation waveform generated during execution of aggregate instruction 2614. As illustrated, pulse program D includes a pre-pulse phase, a stimulation phase, an active recovery phase, a passive recovery phase, and a quiet phase. Each of the phases of pulse program D has a pulse width of 100 µs with the exception of the quiet phase, which has a pulse width of 300 µs. During the stimulation phase, a stimulation current of I is sourced to electrode E1 and a sunk from electrode E2. During the active recovery phase, current flows in the opposite direction, and I is sourced to E2 and sunk from E1.

Figure 26C:
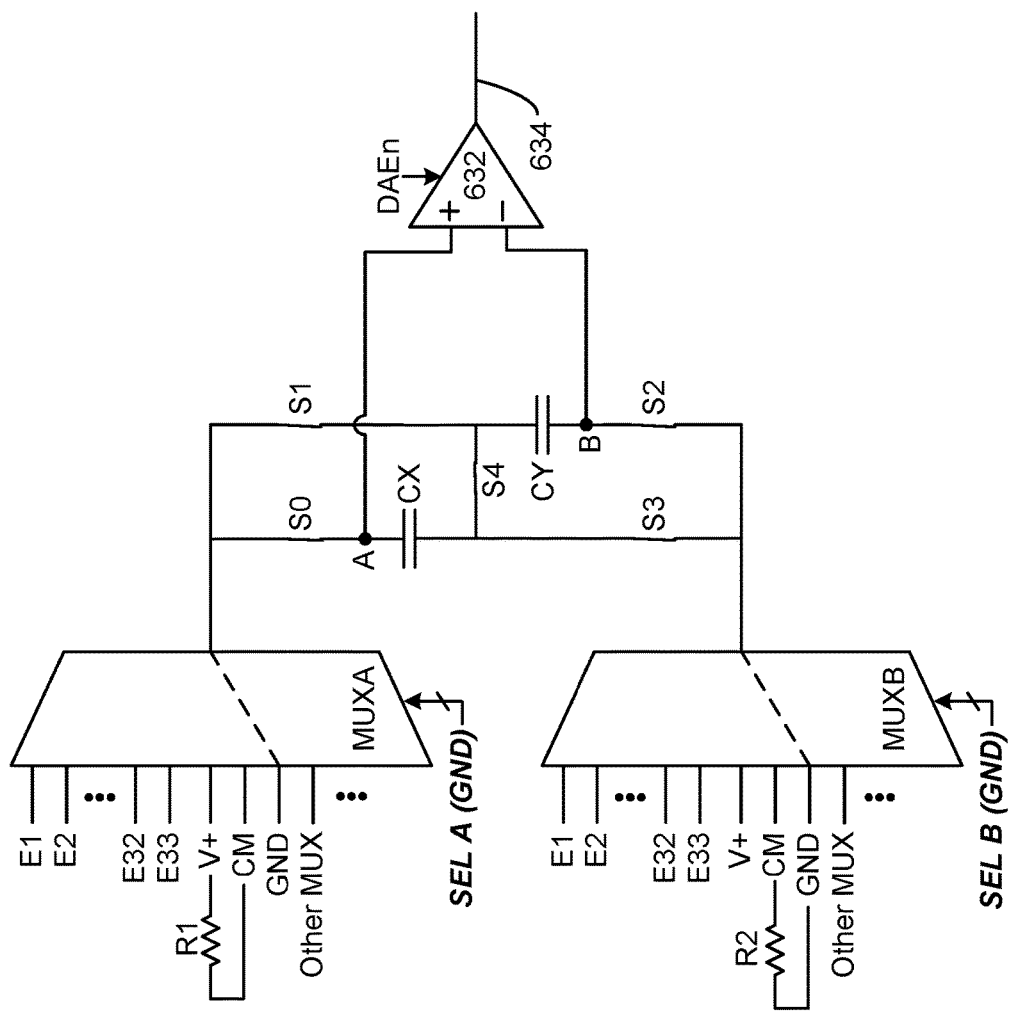

When the measure logic block 612 receives the single aggregate trigger specified by the WT2 instruction from PDC 171(1), it proceeds to the next instruction in the memory 602, which is a set switches instruction (SS1). As illustrated in the timeline in FIG. 26B, the SS1 instruction is executed at the beginning of the execution of the aggregate instruction 2614, during the pre-pulse phase of the first execution of pulse program D. The SS1 instruction causes the measure logic block to send the <SEL A>, <SEL B>, and <S> control signals to the sample and hold circuitry 166 to close all of the S0-S4 switches and to select the ground input from each of MUX A and MUX B. This preparation stage is illustrated in FIG. 26C, which shows that the ground inputs being passed by MUX A and MUX B are shorted together and both plates of the capacitors CX and CY are shorted to ground to ensure that there are no residual voltages across the capacitors prior to taking measurements. Note that the SS1 instruction is executed with the blanking bit set, which causes the switches S0 through S4 to open prior to going to the specified state.

After executing the SS1 instruction, the measure logic block 612 proceeds to the WT3 instruction, which causes the measure logic block 612 to wait for the next occurrence of a phase trigger, which phase trigger corresponds to the start of the execution of the stimulation pulse phase. In the expanded portions of the stimulation pulse and active recovery phases 2602 and 2604, each dashed tick represents a clock cycle (i.e., ten 100 kHz clock cycles during each 100 µs phase). When the measure logic block 612 receives the phase trigger corresponding to the WT3 instruction, it executes the W1 instruction at the next clock cycle. The W1 instruction causes the measure logic block 612 to delay for two clock cycles before executing the SS2 instruction. In the example shown, this delay is utilized to measure the E1'-E2' voltage during the central portion of the pulse phase (i.e., the central 40 µs), during which time the current I passing through the electrodes is most likely to be stable, but the instructions could also be configured to measure the voltage during other phase portions.

Figure 2A:
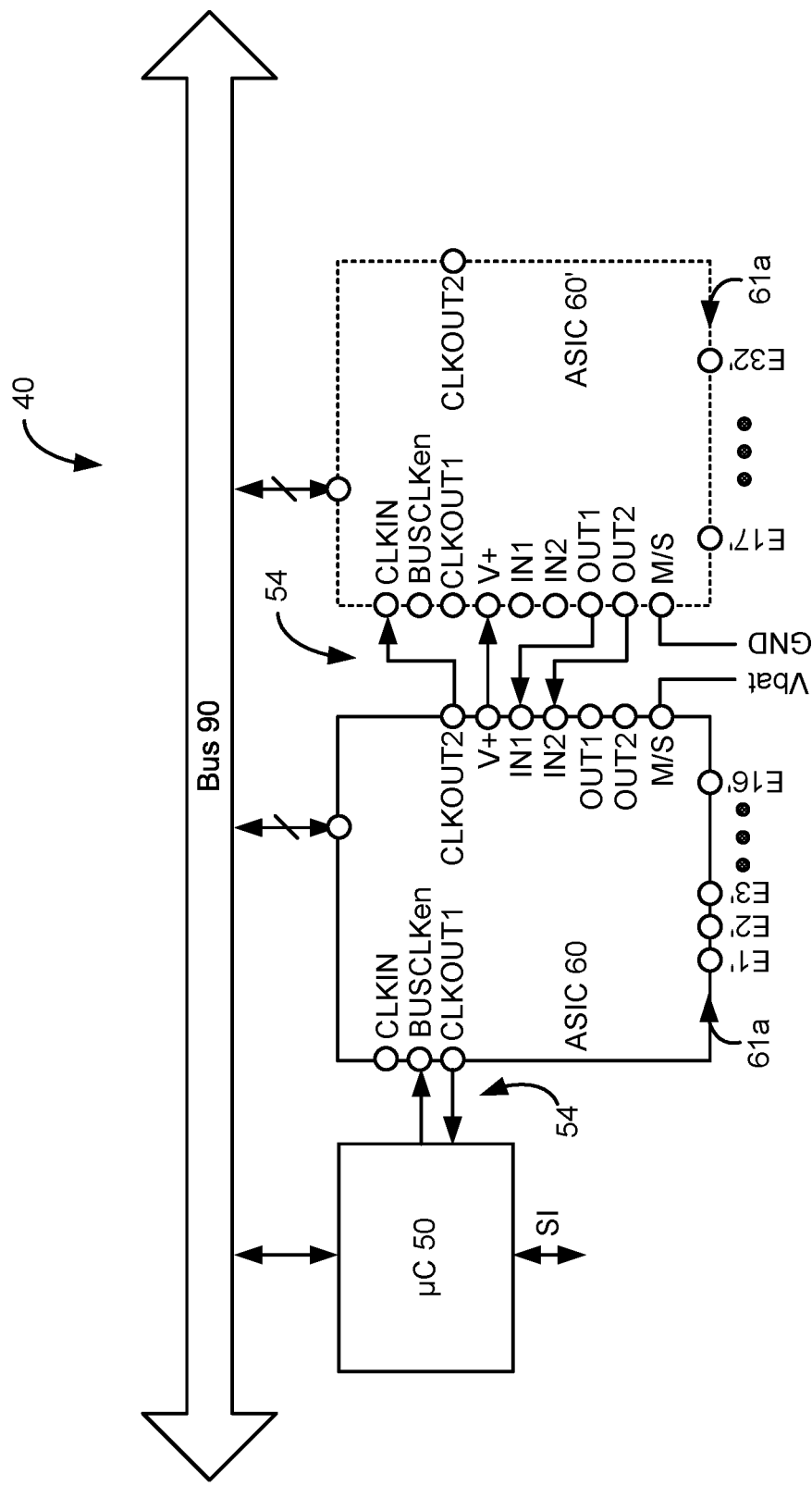
FIGS. 2A-2B show an architecture for the circuitry in the IPG in accordance with the prior art.
Figure 2B:
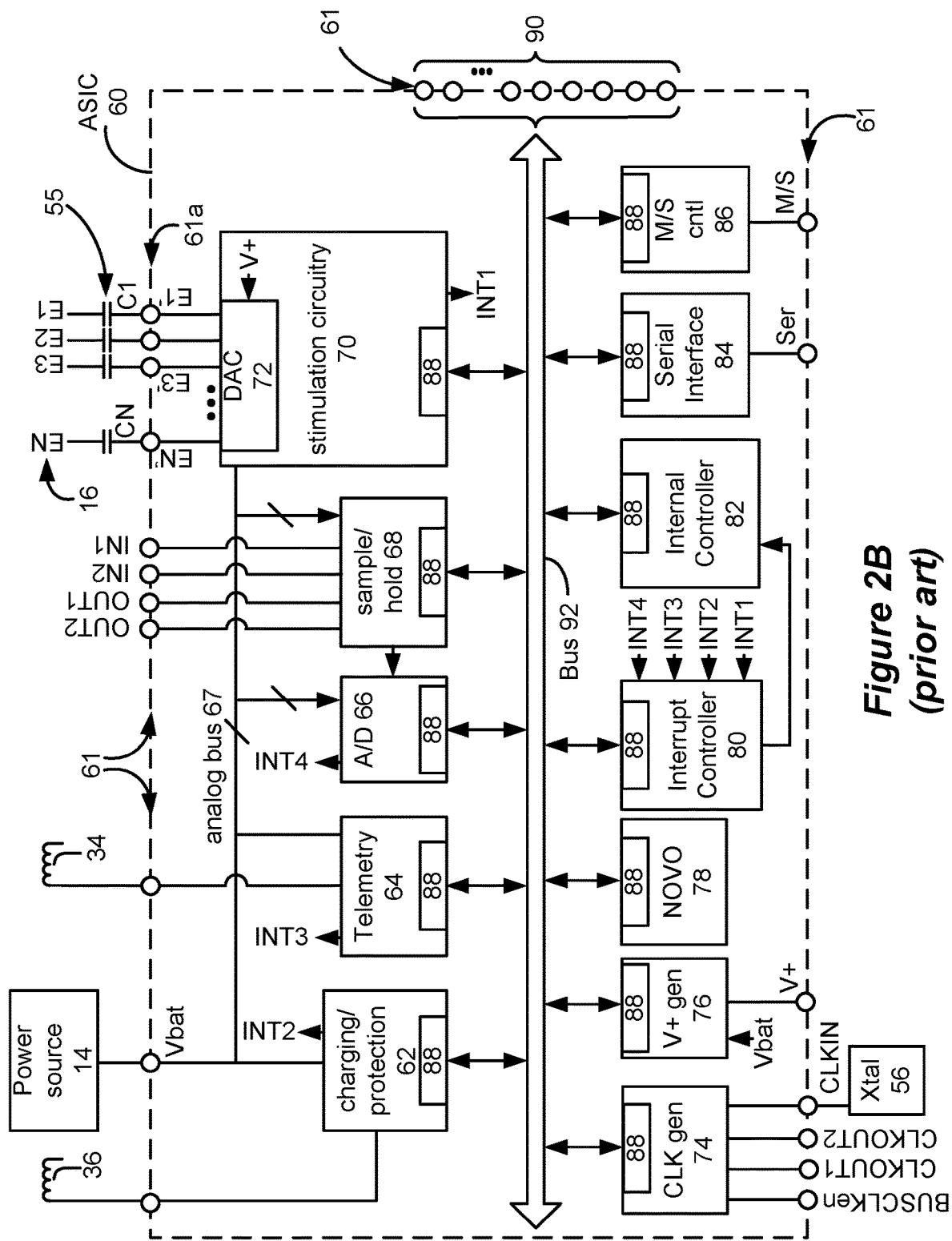
Figure 3A:
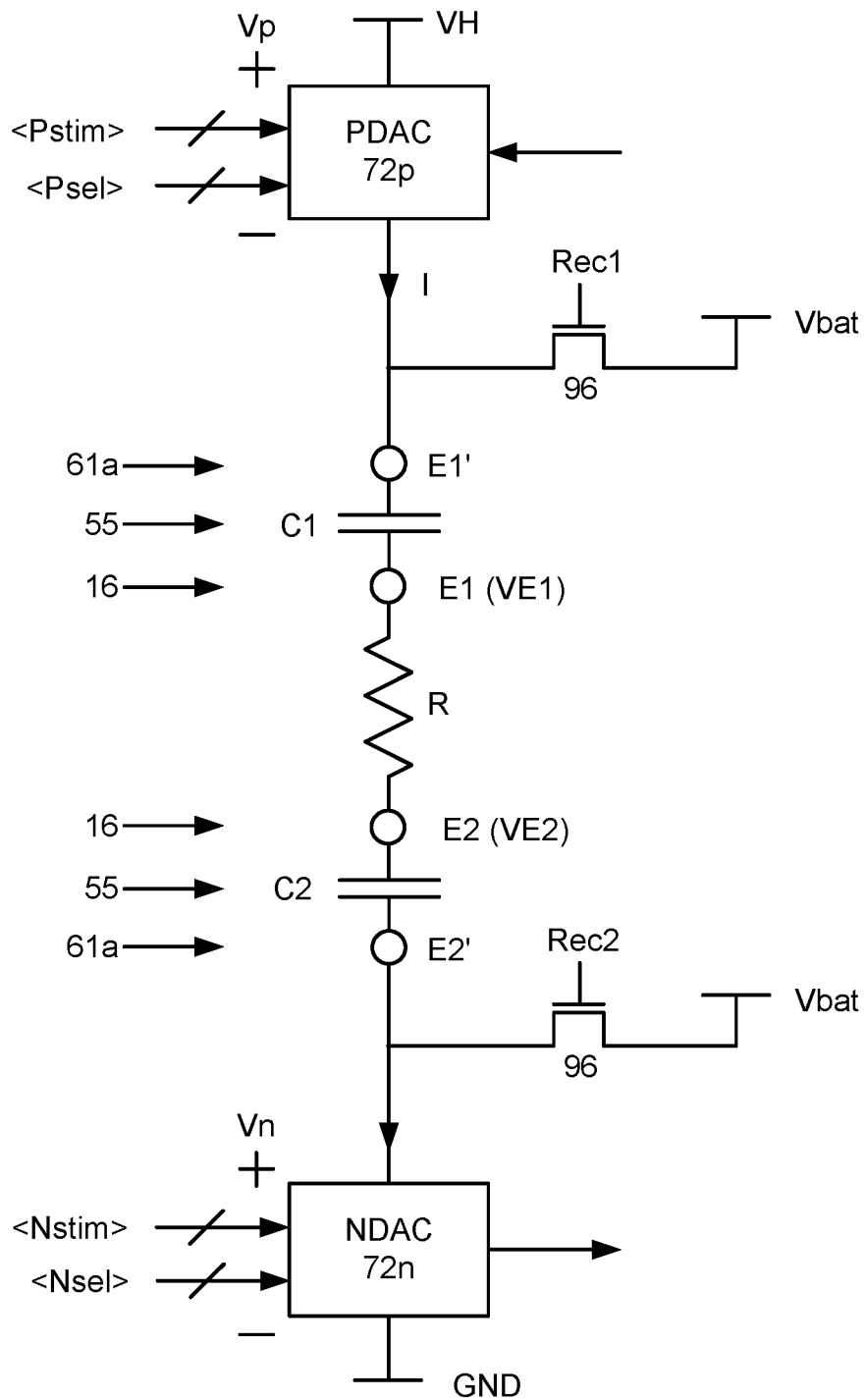
FIG. 3A shows the operation of a Digital-to-Analog Converter (DAC) circuit in delivering a stimulation pulse to electrodes in accordance with the prior art.
Figure 3B:
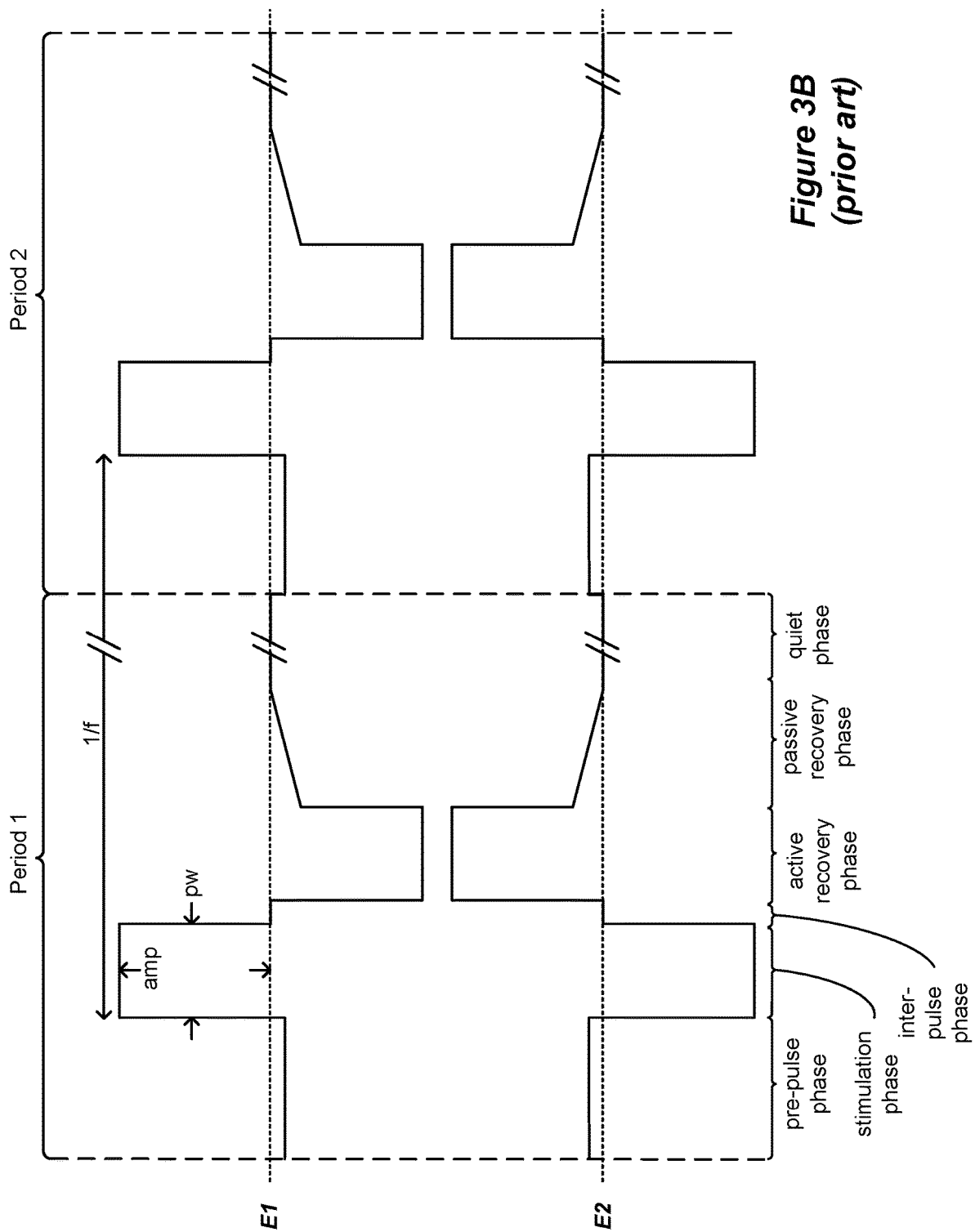
FIG. 3B shows an example stimulation waveform that can be produced by an IPG in accordance with the prior art.
Figure 3C:
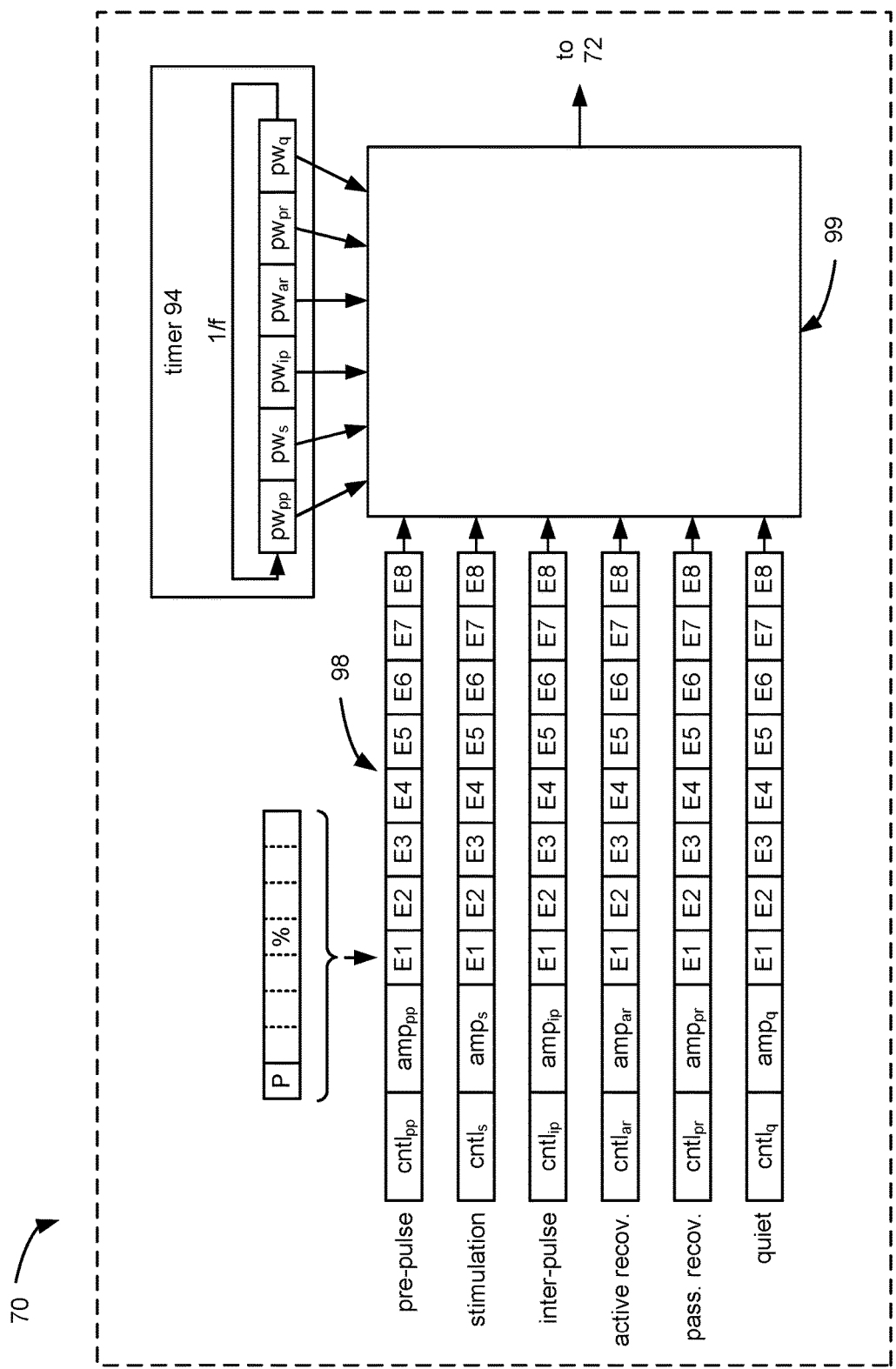
FIG. 3C shows the data arrangement to define the stimulation waveform in FIG. 3B and the stimulation circuitry that processes the control data in the data arrangement in accordance with the prior art.
Figure 26D:
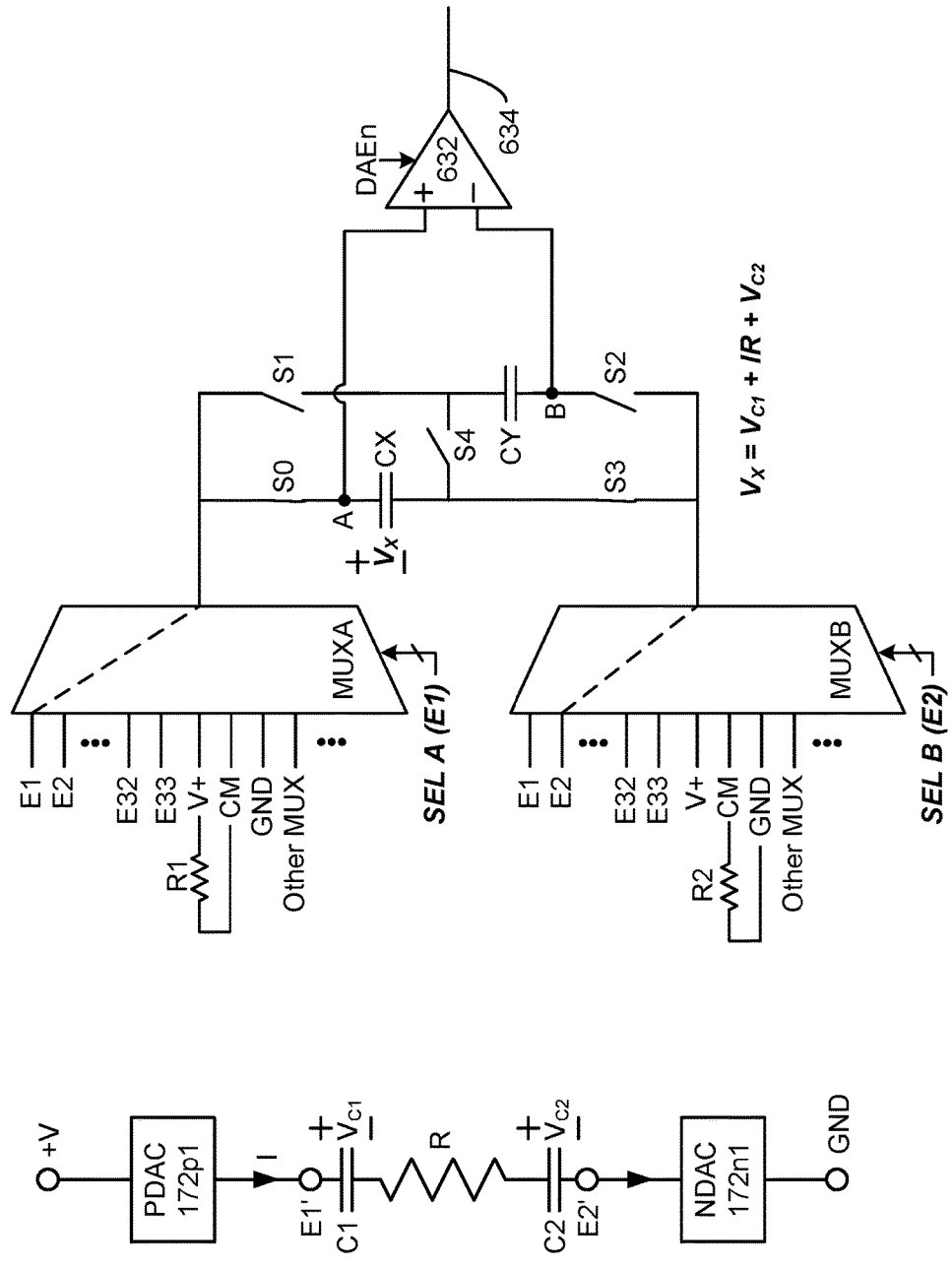

The SS2 instruction causes the measure logic block 612 to issue control signals to the sample and hold circuitry 168 to select the E1 input from MUX A and the E2 input from MUX B and to close the S0 and S3 switches and open the S1, S2, and S4 switches. As illustrated in FIG. 26D, the voltage $V_X$ between electrode nodes E1' and E2' is impressed or stored on capacitor CX, which voltage will equal the sum of the two parasitic voltages across the decoupling capacitors C1 and C2 ($V_{C1}+V_{C2}$) and the drop across the patient's tissue (IR), i.e., $V_X=V_{C1}+IR+V_{C2}$ (see, e.g., FIG. 3A). Note that leaving switches S1, S2, and S4 open isolates capacitor CY, whose voltage drop remains zero by virtue of being grounded during the preparation stage.

Figure 26E:
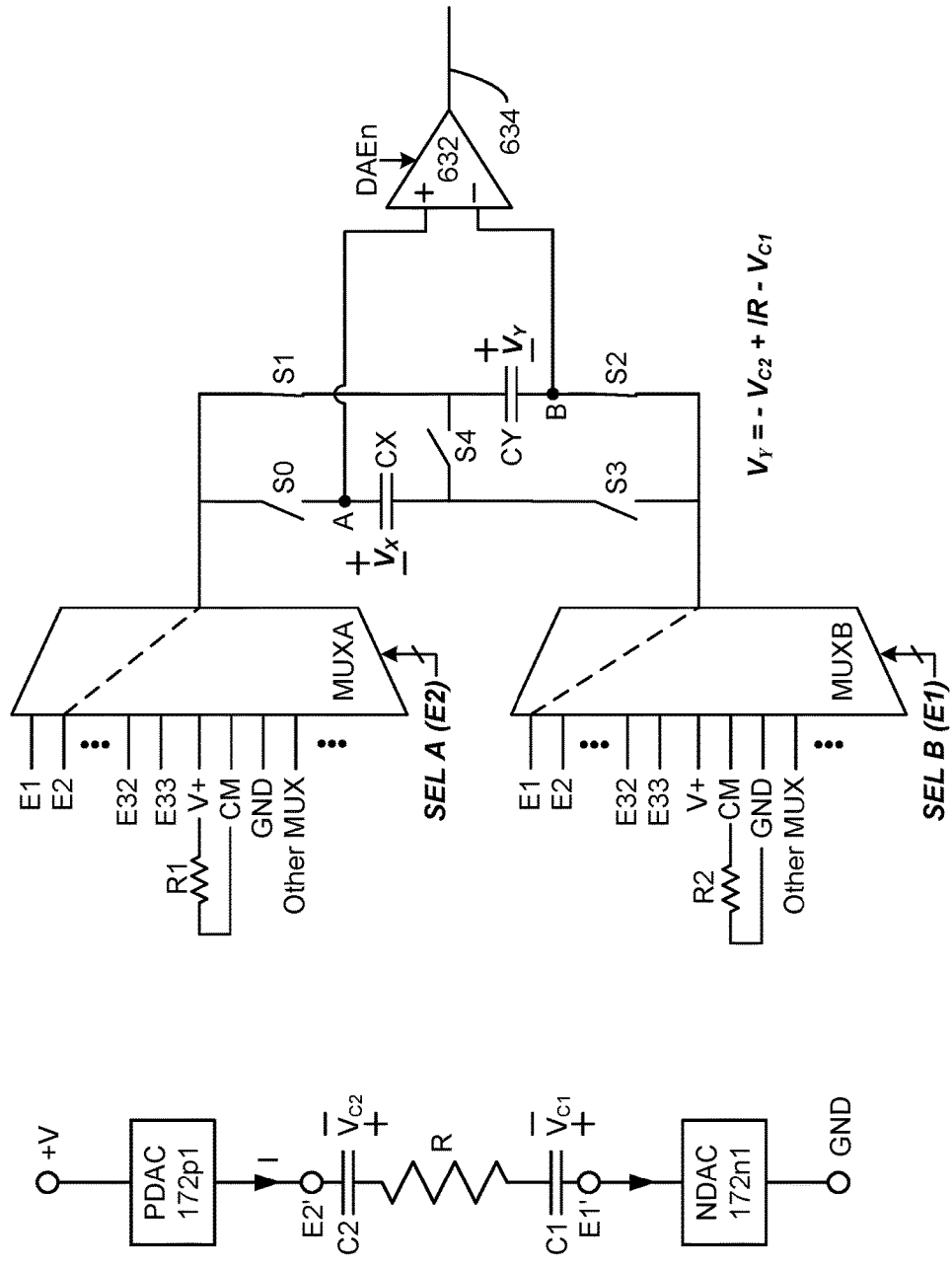

During the clock cycle following execution of the SS2 instruction, the measure logic block executes the W2 instruction, which causes the measure logic block 612 to wait for three clock cycles before executing the SS3 instruction. The SS3 instruction causes the measure logic block 612 to issue control signals to the sample and hold circuitry 168 to select no inputs from either MUX A or MUX B and to perform a blanking operation. After executing the SS3 instruction, the measure logic block 612 executes the WT4 instruction, which causes the measure logic block 612 to wait for the occurrence of the next phase trigger, which phase trigger corresponds to the beginning of the active recovery phase. Instructions W3 through SS5 essentially mirror instructions W1 through SS3, except that the SS4 instruction causes the measure logic block 612 to issue control signals to the sample and hold circuitry 168 to select the E2 input from MUX A and the E1 input from MUX B and to close the S1 and S2 switches and open the S0, S3, and S4 switches. As illustrated in FIG. 26E, the voltage $V_Y$ between electrode nodes E2' and E1' is impressed or stored on capacitor CY, which voltage will again equal the sum of the two parasitic voltages across the decoupling capacitors C1 and C2 and the drop across the patient's tissue (IR). However, because the polarity of stimulation is reversed in the active recovery phase, these parasitic voltages are now subtracted, such that $V_Y=-V_{C2}+IR-V_{C1}$. Note that leaving switches S0, S3, and S4 open isolates capacitor CX, whose voltage remains $V_X$ by virtue of the sample collected earlier during the stimulation phase. Note also that although the blocking capacitors C1 and C2 charge and discharge over the stimulation and active recovery phases, collecting the samples during corresponding time periods in the stimulation pulse phase and the active recovery pulse phase ensures that the values are essentially the same over the sample period and thus that these values can be cancelled out as described below.

Figure 26F:
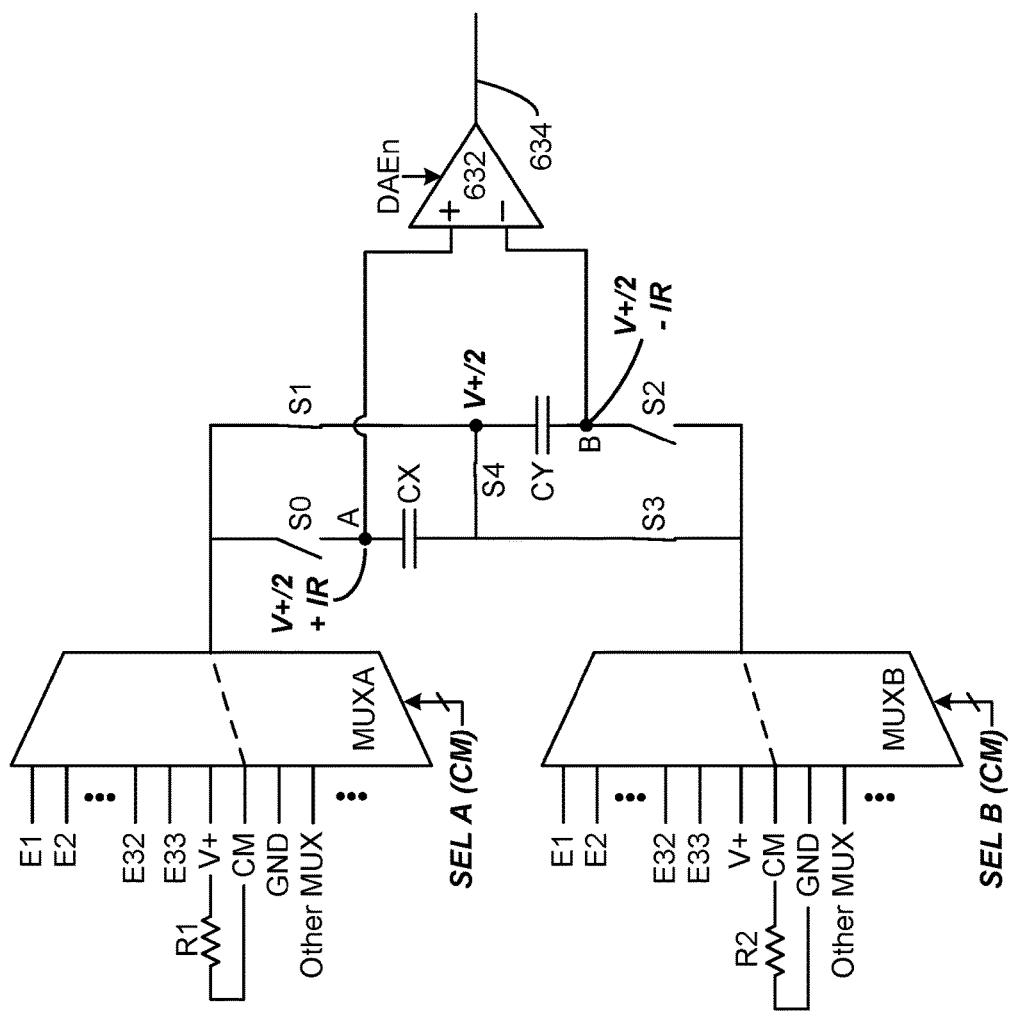

Following execution of the SS5 instruction, the measure logic block executes the W5 instruction, which causes the measure logic block 612 to wait for four clock cycles before executing the SS6 instruction. Due to the wait associated with the W5 instruction, the SS6 instruction is executed during the passive recovery phase. The SS6 instruction causes the measure logic block 612 to issue control signals to the sample and hold circuitry 166 to select the common mode (CM) inputs from both MUX A and MUX B and to close the S1, S3, and S4 switches and open the S0 and S2 switches. As illustrated in FIG. 26F, in this orientation, capacitors CX and CY are connected in series by closing switch S4 and are provided a reference voltage via the common mode inputs to the MUXes. The voltage across the series-connected capacitors CX and CY is equal to the sum of the previously-stored $V_X$ and $V_Y$ values, namely 2IR. Notice that the parasitic voltages across the decoupling capacitors, $V_{C1}$ and $V_{C2}$, are canceled by this series addition, thus removing them from the measurement, which enables a more accurate determination of the resistance R of the patient's tissue. Additionally, selecting the common mode input CM at each of the MUXes and closing switches S1 and S3 causes the common node between the capacitors CX and CY to be set to a reference voltage of V+/2. Notice that the common mode inputs are wired differently at the MUXes: the common mode input at MUX A is coupled to the compliance voltage V+ via a resistor R1, while the common mode input at MUX B is coupled to ground via a resistor R2. In the example shown, R1 and R2 are identical, and of a relatively high value on the order of 250 k-ohm each. When both common mode inputs are selected and shorted at the common node between the capacitors via switches S1 and S3, R1 and R2 form a voltage divider between V+ and ground, resulting in the common mode voltage of V+/2. Because the 2IR voltage across the series-connected capacitors is preserved, the effect is to present a voltage of (V+/2)+IR and a voltage of (V+/2)−IR to the differential amplifier 632.

Figure 26G:
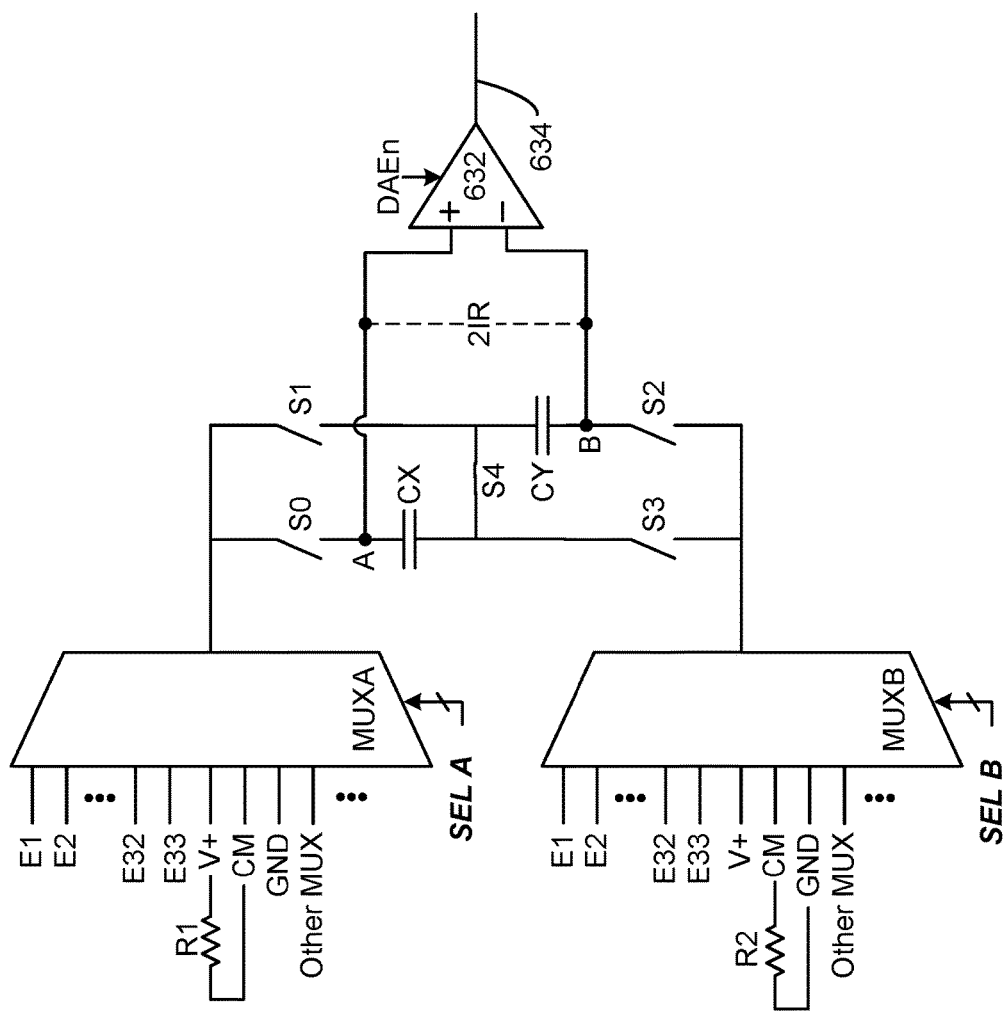

Following execution of the SS6 instruction, the measure logic block 612 executes the W6 instruction, which causes the measure logic block 612 to wait for four clock cycles before executing the SS7 instruction, which, as illustrated in FIG. 26G, causes the measure logic block 612 to issue control signals to the sample and hold circuitry 168 to de-select the common mode voltage at each of the MUXes and open switches S1 and S3 while keeping S4 closed to maintain the series connection of CX and CY and the corresponding presentation of the 2IR value to the differential amplifier 632. Immediately following the execution of the SS7 instruction, the measure logic block 612 executes the M1 measure command, which causes the measure logic block 612 to issue control signals to the ADC 622 to store a digitized value of the analog signal on line 634 in the memory block 624. Note that this M1 measure instruction assumes that the ADC MUX was previously configured to pass the signal from the sample and hold circuitry 168. In the illustrated example, the measure instruction specifies a single sample with no accumulate value, but this could obviously be tailored to desired settings.

The example set of instructions 2616 is shown in long form for purposes of illustration. It will be appreciated that a jump instruction could be utilized to re-use a set of instructions to perform a similar process. Note that the set of instructions 2616 is specific to a single PDC 171(1) (i.e., the wait trigger instructions look only for triggers from this circuit and the instructions are configured based on the known timing of the stimulation associated with this PDC). Other instruction sets may be configured to acquire measurements based on stimulation provided by other PDCs 171. The instruction sets may be configured to, upon obtaining the desired measurements associated with one PDC 171, jump to the instruction set associated with another PDC 171 such that all desired measurements can be obtained.

Figure 27A:
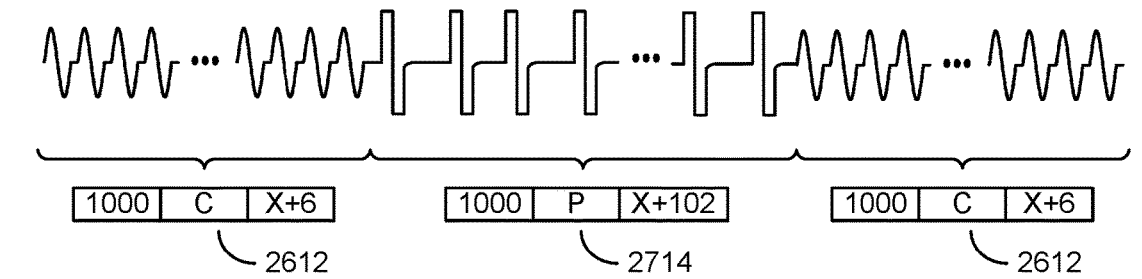
FIGS. 27A and 27B illustrate an example set of instructions to measure a voltage between different pairs of electrode nodes by updating the stimulation circuitry's steering program in accordance with an embodiment of the disclosure.
Figure 27B:
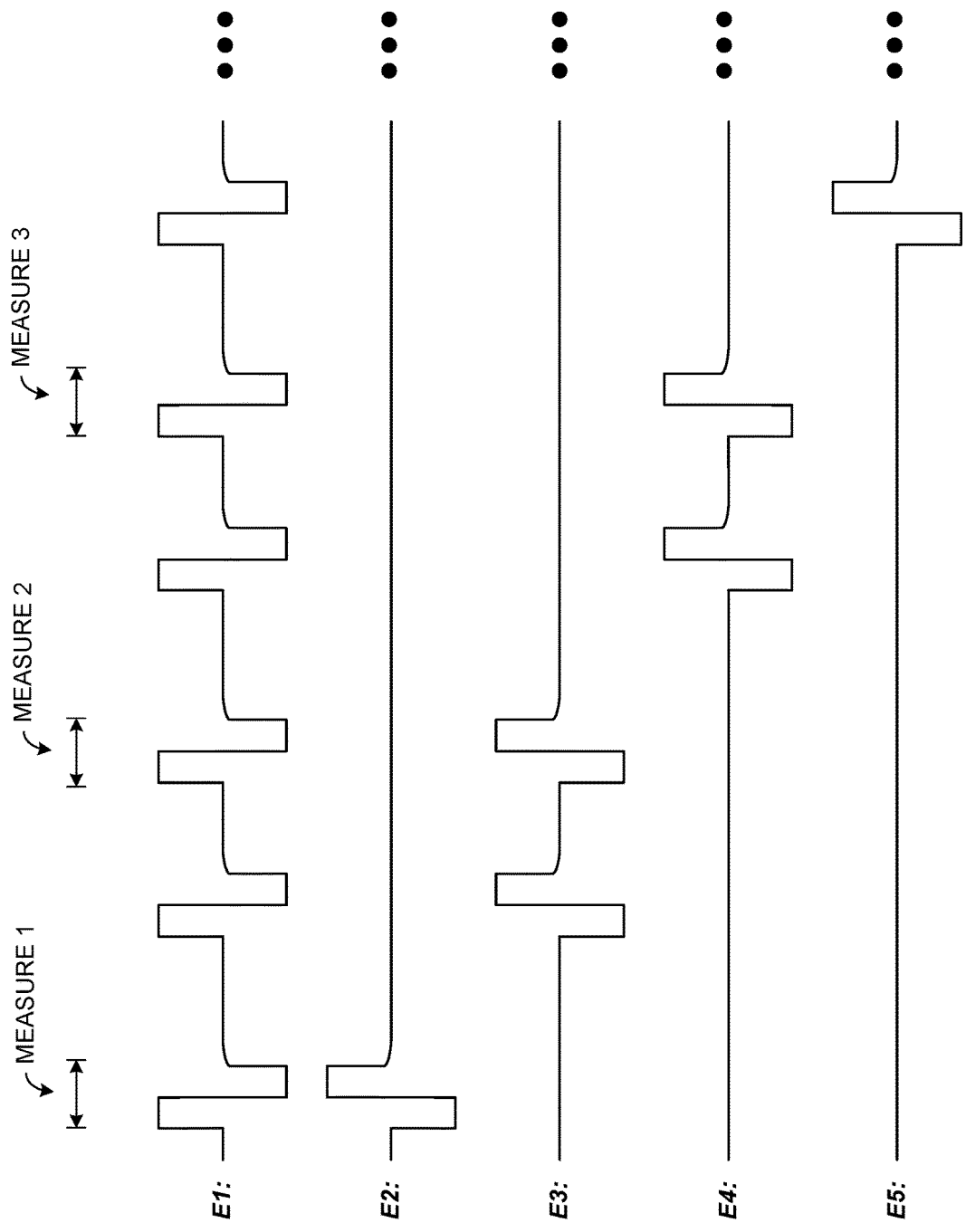

The example measurement sequence described with respect to FIGS. 26A-26G relies upon the electrode configuration in the steering program assigned by the stimulation circuitry 170. For example, during execution of the aggregate instruction 2614, the only electrode voltages that can be measured are those that are defined as active in the steering program A (i.e., electrodes E1 and E2). FIGS. 27A and 27B illustrate a similar type of measurement sequence in which the aggregate instruction specifies a steering program that can be adjusted by the measurement circuitry 167. As shown below, the ability of the measure circuitry 167 to alter the electrode configuration in a steering program enables the measure circuitry 167 to control the delivery of current to selected electrodes and to measure the voltages at the selected electrodes.

In the example shown in FIG. 27A, aggregate instruction 2714 replaces aggregate instruction 2614 in the aggregate program executed by PDC 171(1), which aggregate program otherwise mirrors the aggregate program described with respect to FIGS. 26A-26G. Aggregate instruction 2714 specifies 1000 repetitions of pulse program D in accordance with the electrode configuration specified by steering program P. Steering program P, as shown in FIG. 25, is capable of being adjusted based on the values in the steering memory 606 in the measure circuit 167. This type of aggregate instruction (i.e., using a steering program that is adjustable by the measure circuit 167) may be utilized for the sole purpose of enabling the measure circuitry 167 to perform desired measurements. In fact, the steering program P may only be populated during the time that the measurements are being performed. Therefore, while the aggregate instruction 2714 is executed during each execution of the aggregate program, all of the branch electrode switches 178 may be open, thus preventing current from flowing to any electrode, at all times other than when the measure circuitry 167 populates the steering program P to perform desired measurements. Even when current is delivered due to the execution of the aggregate program 2714, the amplitude may be at a "sub-threshold" level that is not recognizable by the patient.

The set of instructions 2716 is similar in most aspects to the set of instructions 2616 described above with respect to FIGS. 26A-26G. However, the set of instructions 2716 manipulates the steering program P to collect measurements across multiple pairs of electrodes as is now described. The first difference between the set of instructions 2716 and the set of instructions 2616 is the insertion of a set of configuration instructions 2710 between the WT1 and WT2 instructions. The first instruction in the set of configuration instructions 2710 is a steering configuration instruction SC1 that clears the values in the steering memory 606, which is followed by a steering instruction SC2 that writes a 100% stimulation anode configuration to the virtual electrode VA (i.e., electrode 34) and a steering instruction SC3 that writes a 100% stimulation cathode configuration to the virtual electrode VB (i.e., electrode 35) and specifies that the virtual electrode configurations are to be written to the electrodes in the steering memory 606 according to the values in the MUXA and MUXB addresses in the variable memory 604. The remaining instructions in the set of configuration instructions 2710 write values to these MUXA and MUXB addresses. Specifically, the V1 instruction writes the E1 selection value to the MUXA address in the variable memory 604 (address 13 in this example) and the V2 instruction writes the E2 selection value to the MUXB address in the variable memory 604 (address 14 in this example). The combination of SC3, V1, and V2 results in the electrode configuration for virtual electrode VA being written to the E1 portion of the steering memory 606 and the electrode configuration for virtual electrode VB being written to the E1 portion of the steering memory 606. Because the steering memory 606 is written to the steering program P (which can be done continuously or upon any change in the memory 606), this causes electrode E1 to be configured to receive 100% of the stimulation anodic current and electrode E2 to be configured to receive 100% of the stimulation cathodic current.

The WT2 through W1 instructions mirror those described above. The SS2 instruction differs from that described above in that rather than specifying the MUXA and MUXB inputs, the MUXA address and the MUX B address are specified for the MUXA and MUXB select signals. This is accomplished by selecting pre-defined values 126 (for the MUXA address) and 127 (for the MUXB address) in the MUXA and MUXB fields of the set switch instruction in the example shown. Based on the values written to the MUXA and MUXB memory locations (i.e., addresses 13 and 14) in the variable memory 604 by the V1 and V2 instructions, this results in the measure logic block 612 generating control signals <SEL A> and <SEL B> that cause the selection of E1 (which is the anode during the stimulation phase) by MUXA and E2 (which is the cathode during the stimulation phase) by MUXB. In the same manner as described above, the voltage $V_X$ between electrode nodes E1' and E2', which is equal to the sum of the two parasitic voltages across the decoupling capacitors C1 and C2 ($V_{C0}+V_{C1}$) and the drop across the patient's tissue (IR), i.e., $V_X=V_{C1}+IR+V_{C2}$, is impressed or stored on capacitor CX.

The W2 through W3 instructions mirror those described above. The SS4 instruction is similar to the SS2 instruction in that it utilizes the MUX addresses in the memory 604 to retrieve the MUX select values. However, the MUXA portion of the SS4 instruction points to the MUXB address (which stores the value for E2) and the MUXB portion of the SS4 instruction points to the MUX A address (which stores the value for E1). Thus, in the same way as described above, the voltage $V_Y$ between electrode nodes E2' and E1' is impressed or stored on capacitor CY, which voltage will again equal the sum of the two parasitic voltages across the decoupling capacitors C1 and C2 and the drop across the patient's tissue (IR). The W4 through M1 instructions mirror those described above, and thus the same measurement of the voltage between E1 and E2 (which is equal to 2IR) is obtained.

After the M1 instruction, the measurement logic block 612 executes the V3 instruction, which is a variable instruction that increments the value in the MUXB address of the variable memory 604 such that the value corresponds to E3. Because the SC3 instruction specifies that the electrode configurations of virtual electrodes VA and VB are to be written to the electrodes in the steering memory 606 according to the values in the MUXA and MUXB addresses in the variable memory 604, the steering memory 606 is updated to reflect that E1 (which is still identified in the MUXA address) is to receive 100% of the stimulation anodic current and E3 (which is now identified in the MUXB address) is to receive 100% of the stimulation cathodic current. Once again, the steering memory 606 is written to steering program P of the steering memory 502, which changes the electrode configuration utilized in conjunction with the execution of the aggregate instruction 2714.

The WT5 instruction, which is executed after the V3 instruction, causes the measure logic block 612 to wait for two occurrences of a pulse trigger. After receipt of the two pulses specified by the WT5 instruction, the measure logic block 612 executes the J1 jump instruction. The J1 instruction is a conditional jump instruction that causes the measure logic block 612 to loop back to the address of the SS1 instruction if the value in the MUXB address of the variable memory 604 (i.e., address 14) is less than the value in address 1 of the variable memory 604. This example assumes that the value in address 1 of the variable memory 604 has been previously set to a desired value.

FIG. 27B illustrates the stimulation waveform generated as a result of execution of the set of instructions 2716. The voltage between electrode nodes E1' and E2' is sampled and measured during the measure 1 period, the voltage between electrode nodes E1' and E3' is sampled and measured during the measure 2 period, and the voltage between electrode nodes E1' and E4' is sampled and measured during the measure 3 period. Between the measure 1 and measure 2 periods, the V3 instruction causes the electrode associated with the MUXB address to be incremented from E2 to E3, which, in turn, causes the steering program P to be updated such that stimulation is configured between E1 and E3. The WT5 instruction causes measurements to be taken every other pulse and is included only as an example. The process of measuring the voltage between E1' and the next electrode node 61*a* in sequence continues until the incremented electrode number matches the value in address 1 in the variable memory 604. As can be appreciated, the ability of the measure circuit 167 to track the stimulation sequence of each of the PDCs 171 and to update the steering program enables great flexibility in the measurement of desired analog values.

While voltage measurements between electrode nodes have been described, it will be appreciated that other valuable measurements can also be made by configuring an appropriate set of instructions in the measure memory 602. For example, as discussed in U.S. Pat. No. 7,444,181, it can be particularly useful to know the voltage drop appearing across the current sources and sinks, i.e., the PDACs 172*p* and NDACs 172*n*, which voltage drops can only be known in part by monitoring the electrode voltages used during stimulation. By monitoring these voltage drops, the compliance voltage V+ can be set at a magnitude that is sufficient to deliver the required therapeutic current without loading, but not excessively high so as to waste power in the IPG. Such measurements can be taken by sampling the appropriate voltages (i.e., between an active electrode node and VH for PDAC 172*p* and between an active electrode node and ground for NDAC 172*n*) during a single phase of a pulse using the sample and hold circuitry 168 as described in U.S. Pat. No. 9,061,140. A beneficial aspect of the measure circuit 167 is that it enables measurements to be taken without intervention by the microcontroller 150, which allows the microcontroller 150 to remain in the reduced-power state. Thus, the microcontroller 150 can intermittently "wake up" and retrieve values from the memory 624 without having to manage the collection of such measurements, which results in power savings in the IPG.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A pulse generator, comprising:
   a plurality of electrodes;
   memory circuitry configured to store a measurement program comprising a plurality of measure instructions, and an aggregate program comprising a plurality of aggregate instructions;
   stimulation circuitry configured to execute the aggregate program to provide a stimulation waveform at one or more of the electrodes, wherein the stimulation circuitry is configured to issue a plurality of triggers at various points during the execution of the aggregate program; and
   measure circuitry configured to execute the measurement program to cause the measurement of an analog value during the execution of the aggregate program, wherein at least one of the measure instructions in the measurement program is responsive to one of the plurality of triggers to control when the measure circuitry makes the measurement.

2. The pulse generator of claim 1, further comprising sample and hold circuitry, wherein the measure circuitry is configured to issue control signals to the sample and hold circuitry to determine the analog value.

3. The pulse generator of claim 2, wherein at least one of the measure instructions in the measurement program comprises a configuration instruction configured to issue the control signals to the sample and hold circuitry.

4. The pulse generator of claim 2, further comprising digital-to-analog circuitry configured to receive the determined analog value from the sample and hold circuitry.

5. The pulse generator of claim 3, wherein the sample and hold circuitry comprises a plurality of switches, wherein the control signals control the plurality of switches.

6. The pulse generator of claim 2, wherein the sample and hold circuitry comprises a first multiplexer having a first plurality of inputs and a first output and a second multiplexer having a second plurality of inputs and a second output.

7. The pulse generator of claim 6, wherein the first plurality of inputs and the second plurality of inputs each comprise inputs coupled to the plurality of electrodes.

8. The pulse generator of claim 7, wherein the sample and hold circuitry further comprises a first capacitor and a second capacitor, wherein the first output is coupleable to first plates of the first and second capacitors, and wherein the second output is coupleable to second plates of the first and second capacitors.

9. The pulse generator of claim 1, wherein the analog value comprises a voltage between two of the electrodes.

10. The pulse generator of claim 9, wherein the analog value comprises the voltage between two of the electrodes used to provide the stimulation waveform.

11. The pulse generator of claim 1, wherein at least one of the measure instructions in the measurement program comprises a configuration instruction configured to assist in measuring the analog value.

12. The pulse generator of claim 1, wherein one or more of the aggregate instructions specifies a number of applications of a pulse program to a first group of the electrodes.

13. The pulse generator of claim 12, wherein the first group of electrodes is specified in a steering program.

14. The pulse generator of claim 1, wherein the stimulation circuitry is configured to issue at least one of the plurality of triggers at the start of execution of the aggregate program.

15. The pulse generator of claim 1, wherein the stimulation circuitry is configured to issue at least one of the plurality of triggers at the start of each aggregate instruction in the aggregate program.

16. The pulse generator of claim 1, wherein one or more of the aggregate instructions specifies a number of applications of a pulse program to provide a number of pulses at the one or more electrodes.

17. The pulse generator of claim 16, wherein the stimulation circuitry is configured to issue at least one of the plurality of triggers at the start of each pulse program.

18. The pulse generator of claim 16, wherein each pulse specified by the pulse program comprises a number of pulse phases in each pulse.

19. The pulse generator of claim 18, wherein the stimulation circuitry is configured to issue at least one of the plurality of triggers at the start of each pulse phase.

20. The pulse generator of claim 1, wherein the at least one of the measure instructions in the measurement program comprises a wait instruction that is responsive to the one of the plurality of triggers to control when the measure circuitry executes a next of the measure instructions in the measurement program.

* * * * *